US012559722B2

(12) United States Patent
Kukekov et al.

(10) Patent No.: US 12,559,722 B2
(45) Date of Patent: Feb. 24, 2026

(54) HUMAN DISC TISSUE

(71) Applicant: DISCGENICS, INC., Salt Lake City, UT (US)

(72) Inventors: Valery Kukekov, Memphis, TN (US); Umar Akbar, Arlington, TX (US); Christopher D. Duntsch, Huntsville, TX (US)

(73) Assignee: DiscGenics, Inc., Salt Lake City, UT (US)

( * ) Notice: Subject to any disclaimer, the term of this patent is extended or adjusted under 35 U.S.C. 154(b) by 128 days.

(21) Appl. No.: 16/860,652

(22) Filed: Apr. 28, 2020

(65) Prior Publication Data

US 2020/0255806 A1 Aug. 13, 2020

Related U.S. Application Data

(63) Continuation of application No. 15/601,119, filed on May 22, 2017, now Pat. No. 10,633,632, which is a continuation of application No. 13/985,204, filed on Mar. 21, 2014, now Pat. No. 9,657,270.

(51) Int. Cl.
| | |
|---|---|
| *C12N 5/0775* | (2010.01) |
| *A61K 35/32* | (2015.01) |
| *C12N 5/077* | (2010.01) |

(52) U.S. Cl.
CPC ............ *C12N 5/0662* (2013.01); *A61K 35/32* (2013.01); *C12N 5/0655* (2013.01); *C12N 5/0656* (2013.01); *C12N 2500/25* (2013.01); *C12N 2500/46* (2013.01); *C12N 2500/84* (2013.01); *C12N 2500/90* (2013.01); *C12N 2501/11* (2013.01); *C12N 2501/115* (2013.01); *C12N 2501/392* (2013.01); *C12N 2501/603* (2013.01); *C12N 2510/00* (2013.01); *C12N 2513/00* (2013.01); *C12N 2533/54* (2013.01); *C12N 2533/78* (2013.01)

(58) Field of Classification Search
CPC .............. C12N 5/0662; C12N 2533/54; C12N 2501/115; C12N 2501/11; C12N 2533/78
See application file for complete search history.

(56) References Cited

U.S. PATENT DOCUMENTS

| | | | |
|---|---|---|---|
| 9,657,270 | B2 | 5/2017 | Kukekov et al. |
| 2003/0220692 | A1 | 11/2003 | Shapiro et al. |
| 2004/0034427 | A1 | 2/2004 | Goel et al. |
| 2004/0241839 | A1 | 12/2004 | Svetlov et al. |
| 2009/0074835 | A1 | 3/2009 | Kukekeov et al. |
| 2009/0304643 | A1* | 12/2009 | Khurgel ............... C12N 5/0667 |
| | | | 435/395 |
| 2012/0100607 | A1 | 4/2012 | Duntsch et al. |
| 2014/0287501 | A1 | 9/2014 | Kukekov et al. |
| 2017/0253859 | A1 | 9/2017 | Kukekov et al. |

FOREIGN PATENT DOCUMENTS

WO          2012112564 A2          8/2012

OTHER PUBLICATIONS

Ellman, et al., "Biological Impact of the Fibrolast Growth Factor Family on Articular Cartilage and Intervertebral Disc Homeostasis," Gene, Aug. 15, 2008, retrieved from internet: <URL: http://www.ncbi.nlm.nih.gov/pmc/articles/PMC2525607/pdf/nlhms60439.p df>.
Erwin, et al., "Notochord Cells Regulate Intervertebral Disc Chondrocyte Proteoglycan Production and Cell Proliferation", Spine, 2006, vol. 31, No. 10, pp. 1094-1099.
Freshney, R. I., "Culture of Animal Cells: A Manual of Basic Technique and Specialized Applications 6th Edition", Chapters 2 & 16, Hoboken, NJ, John Wiley & Sons, Inc., QH585.2.F74 2010, 2010, pp. 11-23, 269-278.
Gan, et al., "Intervertebral Disc Tissue Engineering II: Cultures of Nucleus Pulposus Cells", Clinical Orthopaedics and Related Research, 2003, No. 411, pp. 315-324.
Okuma, et al., "Reinsertion of Stimulated Nucleus Pulposus Cells Retards Intervertebral Disc Degeneration: an In Vitro and In Vivo Experimental Study," Journal of Orthopaedic Research, 2000, pp. 988-997, vol. 18.
"International Preliminary Report on Patentability", Application No. PCT/US2012/025066, Jun. 20, 2012, 6 pages.
"International Search Report", Application No. PCT/US2012/025066, Jun. 20, 2012, 8 pages.
Thompson, et al., "Stimulation of Mature Canine Intervertebral Disc by Growth Factors", Spine, 1991, vol. 16, No. 3, pp. 253-260.

* cited by examiner

*Primary Examiner* — Kara D Johnson

(74) *Attorney, Agent, or Firm* — Dorsey & Whitney LLP

(57) ABSTRACT

This invention provides disc stem cells, processes for obtaining and culturing disc stem cells, and methods for repairing damaged or diseased disc tissue comprising the use of the disc stem cells of the invention.

28 Claims, 27 Drawing Sheets

48 Hrs

72 Hrs

96 Hrs

120 Hrs

96 Hrs                             120 Hrs

HUMAN DISC TISSUE

CROSS REFERENCE TO RELATED APPLICATIONS

This application is a continuation of U.S. patent application Ser. No. 15/601,119 filed May 22, 2017, now U.S. Pat. No. 10,633,632, which is a continuation of U.S. patent application Ser. No. 13/985,204, filed Mar. 21, 2014 now U.S. Pat. No. 9,657,270, which is a national stage application of PCT Patent Application No. PCT/US2012/025066, filed Feb. 14, 2012, which claims priority to U.S. Provisional Patent Application No. 61/442,315, filed Feb. 14, 2011 and U.S. patent application Ser. No. 13/113,599, filed May 23, 2011, which is a continuation-in-part of U.S. patent application Ser. No. 12/216,544 now U.S. Pat. No. 8,227,246, which claims priority to U.S. Provisional Patent Application No. 60/929,792; all of which are incorporated by reference herein in their entirety.

FIELD OF THE INVENTION

This invention provides disc stem cells, processes for obtaining and culturing disc stem cells, and methods for repairing damaged or diseased disc tissue comprising the use of the disc stem cells of the invention.

BACKGROUND OF THE INVENTION

Neck and lower back pain from degeneration of the spinal disc joint constitutes a common and significant health and economic burden. Indeed, roughly 80% of adults will experience neck and lower back pain at some point in their lives due to intervertebral degeneration. Intervertebral disc degeneration is a product of lifelong, slow, and chronic degeneration that is synchronized with remodeling of the disc and neighboring bony structures. Musculoskeletal disorders of the spine and neck and lower back pain are the leading sources of disability in people less than 45 years of age, and lead to losses of over 90 billion dollars a year in the U.S. They are the $2^{nd}$ most frequent reason to visit a physician, the $5^{th}$ ranking cause of admission to the hospital, and the $3^{rd}$ most common reason for surgical procedures.

Intervertebral degenerative disc disease contributes to structural weakness of the outer capsule known as the annulus, which leads to herniation or protrusion of the disc into the spinal canal or neuroforamina where it impinges on traversing and exiting nerve roots. Intervertebral degenerative disc disease is characterized by a progressive loss of proteoglycans and extracellular matrix in the nucleus pulposus, which causes loss of hydration and decreased joint mobility. The medical conditions associated with intervertebral degenerative disc disease include disc herniation, radiculopathy, myelopathy, spinal stenosis, and all of these are closely associated with neck and lower back pain and extremity pain from affected nerve roots.

If a patient with neck and lower back pain fails to improve with conservative management, he is often referred for a surgical intervention, of which the most common is a discectomy, with or without fusion. One alternative to discectomy is intervertebral artificial disc insertion, which is meant to provide a means of pain relief through a stable motion-sparing reconstruction of the intervertebral segment. The drawbacks of this approach is the permanent disruption of the joint, and a high risk of chronic low grade arthritis in that joint secondary to the natural biologic response of healthy or normal tissue to tissue damage.

Another approach is a biological approach, in which non-disc cells, nucleus pulposus cells, or tissue engineered disc material is inserted into the damaged NP to regenerate the matrix and restore the disc's biomechanical function. However, non-disc cells do not have the appropriate gene program required to survive in the harsh metabolic environment of the disc space, or produce the appropriate proteoglycan products, or have the intracellular biomechanical cytoskeleton and protein machinery to withstand the constant and significant compressive forces of the disc. Additionally, nucleus pulposus cells lack the ability to divide more than a few times, and thus are not a sustainable cell source for long term regeneration. Finally, to date, a viable source of tissue engineered disc material does not exist.

Tissue engineering approaches have not been successful to date, in part due to limitations in knowledge and tissue biology relative to needs of disc tissue engineering and in part, to the harsh biomechanical and biologic environment of the disc, which is inhospitable to most cell types. Finally, in the absence of a disc tissue stem cell for tissue engineering, the use of other stem cell types such as mesenchymal stem cells and embryonic stem cells has been attempted, but they do not naturally reprogram to functional disc cells successfully.

One branch of biologics uses stem cells such as mesenchymal stem cells, embryonic stem cells, and adipose stein cells in tissue engineering. One of the major obstacles in disc repair using stem cell therapy is the ability to differentiate primary stem cell explants into the appropriate cell type and/or expand them in sufficient amounts for in vivo therapeutics. Very often, the process of reprogramming or "pushing" a stern cell towards a given fate produces cells that may have some of the properties of the targeted cell type, hut are not adequately functional, or a cell population extremely limited in its ability to proliferate further once they are manipulated in vitro. The stem cells thus obtained are not a viable product, because (a) they are too few; and (b) they lack the proper phenotype and/or function. Therefore, there is an urgent need in the art for a technique that provides stem cells that may be further expanded even after in vitro manipulation and maintain the proper phenotype and function. The present application answers this need.

SUMMARY OF THE INVENTION

In one embodiment, the present invention provides a method of amplifying and enriching a disc stem cell population comprising the steps of: (a) culturing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) culturing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) culturing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of .disc stem cells from said third medium, thereby amplifying and enriching a disc stem cell population.

In another embodiment, the present invention provides a method of amplifying a population of nucleus pulposus cells comprising the steps of: (a) suspending isolated nucleus pulposus cells in a medium comprising approximately 14-15% serum, basic fibroblast growth factor (bFGF), epidermal growth factor (EGF), and 30-40% human neonatal foreskin fibroblast (NFF) cell supernatant; and (b) plating the suspension onto gelatin-coated tissue culture plates for 5-14 days, wherein said cells grow as an attached monolayer, thereby amplifying a nucleus pulposus cell population.

In another embodiment, the present invention provides a method of amplifying and enriching a disc stem cell population from nucleus pulposus cells comprising the steps of: (a) suspending a nucleus pulposus cell population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) culturing the single cell suspension for 10-20 days, wherein an individual disc stem cell grows into a sphere-like cell cluster in a clonal manner, thereby amplifying and enriching a disc stem cell population.

In another embodiment, the present invention provides a method of amplifying and enriching a disc stem cell population comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (IMF) and lacking methylcellulose; (b) distributing the suspension onto ultra-low binding culture plates; (c) culturing said suspension for 8-16 days, wherein said cluster or cell grows into a large aggregate cluster of heterogeneous morphology, thereby amplifying and enriching a disc stem cell population.

In another embodiment, the present invention provides an amplified nucleus pulposus cell population obtained using a method comprising the steps of: (a) suspending isolated nucleus pulposus cells in a medium comprising approximately 14-15% serum, basic fibroblast growth factor (bFGF), epidermal growth factor (EGF), and 30-40% human neonatal foreskin fibroblast (NFF) cell supernatant; and (b) plating the suspension onto gelatin-coated tissue culture plates for 5-14 days, wherein said cells grow as an attached monolayer, thereby producing an amplified nucleus pulposus cell population.

In another embodiment, the present invention provides a disc tissue derived clonal stem cell population obtained using a method comprising the steps of: (a) suspending a nucleus pulposus cell population in a medium comprising 50% methylcellulose, 5% serum, basic fibroblast growth factor (bFGF), and epidermal growth factor (EGF); (b) distributing the suspension onto ultra-low binding culture plates; and (c) culturing said suspension for 10-20 days, wherein an individual disc stem cell grows into a sphere-like cell cluster in a clonal manner, thereby producing a disc tissue derived clonal stem cell population.

In another embodiment, the present invention provides a disc tissue derived :heterogeneous stem cell population obtained using a method comprising the steps of: (a) suspending a sphere-like cluster of disc stem cells or an isolated disc stein cell from said sphere-like cell cluster in a medium comprising 10% serum, basic fibroblast growth factor (bFGF), and epidermal growth factor (EGF) and lacking methylcellulose; (b) distributing the suspension onto ultra-low binding culture plates; (c) culturing said suspension for 8-16 days, wherein said cluster or cell grows into a large aggregate cluster of heterogeneous morphology, thereby producing a disc tissue derived heterogeneous stem cell population.

In another embodiment, the present invention provides an amplified and enriched disc stem cell population obtained using a method comprising the steps of: (a) culturing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) culturing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) culturing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, thereby producing an amplified and enriched disc stem cell population.

In another embodiment, the present invention provides a method of treating a subject having a herniated disc, comprising the step of administering to said subject an amplified disc stem cell population obtained using a method comprising the steps of: (a) culturing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) culturing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) culturing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, thereby producing said amplified and enriched disc stem cell population, and thereby treating said subject having a herniated disc.

In another embodiment, the present invention provides a method of treating damage to or disease of the spinal joint of a subject, comprising the step of administering to said subject an amplified disc stem cell population obtained using a method comprising the steps of: (a) culturing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (h) isolating a single cell population of nucleus pulposus cells from said first medium; (c) culturing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e)

culturing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, thereby producing said amplified and enriched disc stem cell population, and thereby treating damage to or disease of the spinal joint of said subject.

In another embodiment, the present invention provides a method of treating damage to or disease of a joint of a subject, comprising the step of administering to said subject an amplified disc stem cell population obtained using a method comprising the steps of: (a) culturing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) culturing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) culturing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, thereby producing said amplified and enriched disc stem cell population, and— thereby repairing said damaged or diseased disc tissue.

In another embodiment, the present invention provides a method of preventing, inhibiting, or decreasing the likelihood of damage to or disease of the spinal joint of a subject, comprising the step of administering to said subject an amplified disc stem cell population obtained using a method comprising the steps of: (a) culturing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) culturing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) culturing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, thereby producing said amplified and enriched disc stem cell population, and thereby preventing, inhibiting, or decreasing the likelihood of damage to or disease of the spinal joint of said subject.

In another embodiment, the present invention provides a method of preventing, inhibiting, or decreasing the likelihood of damage to or disease of a cartilage-containing joint of a subject, comprising the step of administering to said subject an amplified disc stem cell population obtained using a method comprising the steps of: (a) culturing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) culturing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) culturing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, thereby producing said amplified and enriched disc stem cell population, and thereby preventing, inhibiting, or decreasing the likelihood of damage to or disease of the cartilage-containing joint of said subject.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE INVENTION

Figure 1:
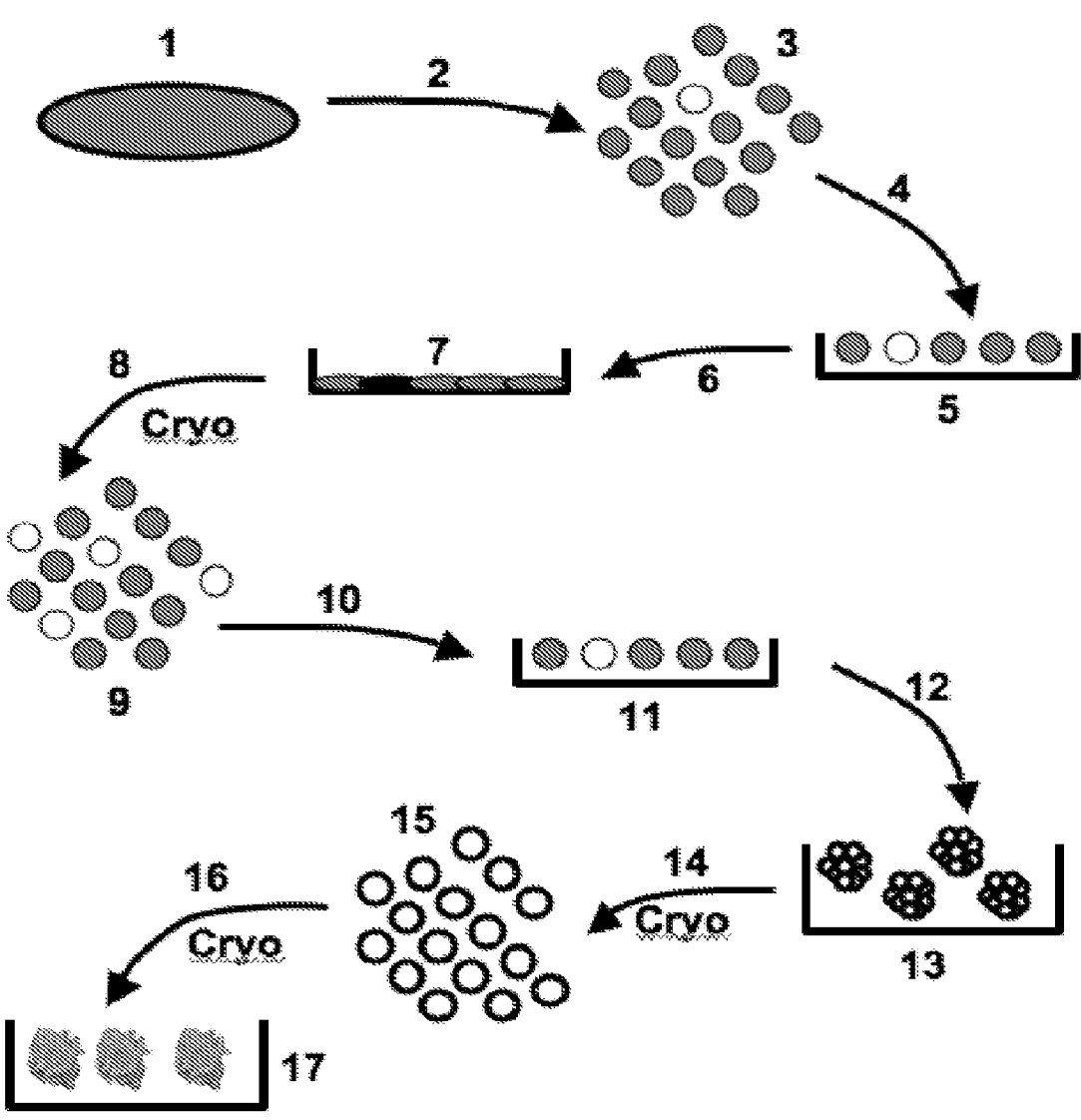
FIG. 1. Schematic diagram of the Discotek Culture Platform. Preparation of a single cell suspension from a disc tissue specimen (reference numerals 1-3); the Attachment Culture Method (reference numerals 4-7); the Discosphere Culture Method (reference numerals 8-13); and the Cluster Culture Method (reference numerals 14-17). "Cryo" indicates the timing of an optional cell cryopreservation step for each method.

The intervertebral disc consists of three main anatomic structures: the cartilaginous vertebral end plates, the annulus fibrosus (outer layer), and the nucleus pulposus (interior structure). In addition, the vertebral endplates are lined with a thin layer of hyaline cartilage. The annulus fibrosus (AF) consists of concentric lamellae of primarily collagen I, and small amounts of several other collagens. The lamellae are loosely bound to each other and contain fibroblast-like cells. The inner portion of the annulus fibrosus comprises cells that resemble chondrocytes and merges with the nucleus pulposus at a transitional zone between the two types of tissues. The gelatinous interior nucleus pulposus (NP) is largely acellular and indeed is the largest avascular structure in the body. It is a cartilage-like tissue with a molecular framework abundant in extracellular matrix that is made up of 50% proteoglycans (mainly aggrecan), 20% collagen H fibrils, and small amounts of other collagens.

The spinal disc of all mammals originates from the notochord which organizes notochordal tissue and paraxial mesoderm into the fetal spine.

The inventors of the present application have discovered and developed a disc stem cell culture platform that enables isolation, culture, and expansion of disc stem cells from adult disc tissue. Disc stem cells prepared in this manner can be subsequently introduced into the disc space as a regenerative therapy after partial discectomy or discoplasty for the treatment of severe degenerative disc disease and/or to reconstruct and regenerate defects in the joint that occur as sequalae to discectomy.

The present invention provides compositions and methods of producing and using said compositions that replace tissue degeneration or iatrogenic disc defects due to surgery with tissue regeneration by combining tissue engineering with the proliferative and functional potential at the cellular level of adult disc stem cells. In particular, the inventors of the present application have developed a process to culture disc stem cells capable of forming discospheres and disc clusters, which may be used for in vitro and ex vivo research and development, and in vivo therapy of diseased or damaged disc tissue.

The present invention provides a method of isolating and culturing disc stem cells, such that the disc stem cells maintain their functionality and/or experience a gain in functionality and their ability to expand. The disc stem cells obtained by the methods of the present invention are multipotent, as they can differentiate into different types of cells, each type expressing different biomarkers as described hereinbelow, having different morphologies, and giving rise to different phenotypes. Thus, in one embodiment, the disc stem cells of the present invention, when grown under the described conditions, mature into disc progenitor cells, which in turn develop into nucleus pulposus cells, which form disc tissue upon maturation.

In one embodiment, the terms "differentiate" or "differentiation" refer to the development of mature lineage specific cells with specialized structure and function from immature unspecialized or less specialized precursor cells, and includes the development of cells that possess the function of nucleus pulposus cells from precursor cells, disc stem cells, or disc progenitor cells.

In one embodiment, an isolated disc stem cell of the present invention is derived from the nucleus pulposus tissue of a subject. The nucleus pulposus is a jelly-like substance at the center of the spinal disc which comprises chondrocytes, collagen fibrils, and proteoglycans such as hyaluronic acid and aggrecan which attract water.

In another embodiment, the present invention provides a population of disc stem cells that can form discospheres comprising disc stem cells and early disc progenitor cells, which, in another embodiment may be used to produce nucleus pulposus cells.

In an additional embodiment, the present invention provides disc stem cells combined with biologically active factors useful for the treatment in situ of degenerative disc disease, structural disc pathology, joint destruction and annulus disruption, and regeneration of disc tissue.

In one embodiment, the isolated disc stem cell population of the present invention is a human disc stem cell population. In another embodiment, the isolated disc stem cell population of the present invention is a non-human disc stem cell population. In another embodiment, the isolated disc stem cell population of the present invention is a mammalian disc stem cell population. In another embodiment, the isolated disc stem cell population of the present invention is a primate, feline, canine, bovine, ovine, porcine, equine, murine, or lapin (rabbit) disc stem cell population.

In another embodiment, the present invention provides a method of capturing, salvaging, stabilizing, and enriching rare stem cell fractions. In one embodiment, the methods of the present invention are particularly useful when stem cells are present in small numbers, which in one embodiment, is due to the nature of the tissue or species from which the tissue is derived (e.g., human adult degenerative tissue and adult porcine tissue which are atypically acellular, etc.). In another embodiment, stem cells are present in small numbers, because the starting tissue sample is small in weight, volume, or a combination thereof.

In another embodiment, the present invention provides a method to enhance the stem cell potential of a stem cell population by driving stem cells toward increased plasticity, immaturity, or a combination thereof. In one embodiment, markers of immaturity include, inter alia, expression of embryonic transcription regulation factors such as OCT-4.

In one embodiment, disc stem cells of the present invention are able to both proliferate under certain conditions that are described herein and to differentiate under certain conditions that are described herein and known in the art.

In one embodiment, cells of the present invention are cultured in a culture vessel to purify or amplify a cell population. In one embodiment, "culturing" is intended to refer to laboratory procedures that involve placing cells in culture medium for an appropriate amount of time to allow stasis of the cells, or to allow the cells to proliferate, differentiate and/or secrete extracellular matrix.

In one embodiment, the present invention provides a method of producing an amplified disc stem cell population. In another embodiment, the present invention provides a method of producing an enriched disc stem cell population. In another embodiment, the present invention provides a method of producing an amplified and enriched disc stem cell population. In one embodiment, the present invention provides a method of amplifying a disc stem cell population. In another embodiment, the present invention provides a method of enriching a disc stem cell population. In another embodiment, the present invention provides a method of amplifying and enriching a disc stem cell population.

In one embodiment, a disc stem cell population is amplified, enriched, or a combination thereof from nucleus pulposus cells, which in one embodiment, are cells isolated from the nucleus pulposus. In one embodiment, nucleus pulposus cells, as referred to herein, comprise mature nucleus pulposus cells, fibroblasts, nucleus pulposus stem cells, notochordal precursors, notochordal cells, or a combination thereof. In another embodiment, nucleus pulposus cells, as referred to herein, comprise mature nucleus pulposus cells, nucleus pulposus stem cells, notochordal precursors, and notochordal cells. In one embodiment, mature nucleus pulposus cells comprise differentiated nucleus pulposus cells, which, in one embodiment, express markers of differentiated nucleus pulposus-cells as described and exemplified herein.

In one embodiment, "amplifying" a cell population refers to increasing the number of cells in the population, regardless of cell type. In another embodiment, amplifying refers to equally increasing the number of each cell type present in the population such that the percentage of each cell type in the population remains constant while the total number of cells increases. In another embodiment, amplifying refers to increasing the number of each cell type present in the population, wherein some cell types multiply at greater rates than others such that the percentage of each cell type in the population changes. In one embodiment, amplifying refers to at least doubling the number of cells in a population. In another embodiment, amplifying refers to at least tripling the number of cells in a population. In another embodiment, amplifying refers to increasing the number of cells in a population by at least 50%. In another embodiment, amplifying refers to increasing the number of cells in a population by at least 75%. In another embodiment, amplifying refers to multiplying the number of cells in a population by at least 36. In another embodiment, amplifying refers to multiplying the number of cells in a population by at least 25. In another embodiment, amplifying refers to multiplying the number of cells in a population by at least 10. In another embodiment, amplifying refers to multiplying the number of cells in a population by at least 50. Thus, in one embodiment, an attachment culture amplifies stem cells. In another embodiment, sphere culture amplifies stem cells. In another embodiment, cluster culture amplifies stem cells.

In one embodiment, "enriching" a cell population refers to increasing the percentage of a particular cell type in a population. In one embodiment, enriching refers to increasing the percentage of a cell type in a population to 25%. In another embodiment, enriching refers to increasing the percentage of a cell type in a population to 50%. In another embodiment, enriching refers to increasing the percentage of a cell type in a population to 75%. In another embodiment, enriching refers to increasing the percentage of a cell type in a population to 80%. In another embodiment, enriching refers to increasing the percentage of a cell type in a population to 85%. In another embodiment, enriching refers to increasing the percentage of a cell type in a population to 90%. In another embodiment, enriching refers to increasing the percentage of a cell type in a population to 95%. In another embodiment, enriching refers to increasing the percentage of a cell type in a population to 99%. Thus, in one embodiment, an attachment culture does not enrich for stem cells. In another embodiment, sphere culture enriches for stem cells. In another embodiment, cluster culture enriches for stem cells.

In one embodiment, "culture vessel" refers to any container in which cells may be cultured. Culture vessels include, but are not limited to, tissue culture flasks, 96 well plates, culture dishes, culture slides, and rotating wall vessels.

In another embodiment, the present invention provides a method to gently and safely derive single disc stem cells from disc tissue at higher yields than those produced with typical methods of tissue preparation currently available.

Accordingly, the present invention provides a method of isolating disc stem cells from disc tissue obtained from a subject. In one embodiment, the subject is a mammal. In another embodiment, the subject is a human. In one embodiment, the method comprises mechanical disruption and enzymatic digestion for 24 hours of the tissue, washing to remove debris and obtaining a cell suspension that comprises all disc tissue cells, including mature nucleus pulposus cells, disc stem cells, fibroblasts, notochordal cells, and several other cell types. The cell suspension contains all cell types in a manner which is roughly equivalent to that of disc tissue, with disc stem cells representing less than 1% of the cell population, and nucleus pulposus cells representing 90% of the cell population. The cells are then plated on gelatin-coated culture plates at 50,000 cells per $cm^2$ in a medium that contains modified human neonatal foreskin fibroblast (NH') conditioned media containing approximately 15% serum, EGF, and basic fibroblast growth factor (bFGF).

In one embodiment, the disc stem cell population is 0.001 to 20% of the nucleus pulposus cell population. In one embodiment, the percentage of disc stem cells in a nucleus pulposus sample depends on the starting disc tissue age, stage of development, disease status, species of origin, or combination thereof. In one embodiment, all cell populations typically present in the disc are represented in this culture, and all are increased in proportion during the culture. Thus, while the proportions of stem cells may remain the same after the culture method, the absolute numbers of each type of disc cell (most importantly disc stem cells) are increased.

In one embodiment, disc tissue is procured from a human patient during a surgical procedure. In another embodiment, disc tissue is procured from an experimental animal model. In one embodiment, the tissue is processed by dissection and then enzymatically digested in media supplemented with Collagenase II, in one embodiment, at 200 units/ml, in one embodiment, for 24 hours, in one embodiment, at 37° C. for 24 hours. In another embodiment, tissue is enzymatically digested using hyaluronidase. In some embodiments of the invention, non-nucleus pulposus or non-precursor cells are removed after hyaluronidase treatment using methods familiar to the skilled artisan, such as, for example, elutration, which involves differential centrifugation based upon the buoyant density of the cells, or centrifugation over a Percoll gradient. In one embodiment, cells from the digested tissue are put into a single cell suspension.

In another embodiment, a heterogeneous population of nucleus pulposus cells is obtained from a biopsy specimen of nucleus-pulposi minced in pieces. In another embodiment, the pieces are 0.5-10 mm in size. In another embodiment, the pieces are 0.5-20 mm in size. In another embodiment, the pieces are 0.5-3 mm in size. In another embodiment, the pieces are 3-6 mm in size. In another embodiment, the pieces are 6-12 mm in size. In another embodiment, the pieces are 12-20 mm in size. In another embodiment, the pieces are 1-6 mm in size. In another embodiment, the pieces are 3-5 mm in size. In another embodiment, the pieces are 1-4 mm in size. In another embodiment, the pieces are 2-3 mm in size. In another embodiment, neonatal foreskin fibroblast tissue for making neonatal foreskin fibroblast cell supernatant is minced in pieces. In one embodiment, neonatal foreskin fibroblast tissue is minced into pieces the size of which is described hereinabove.

In another embodiment, a heterogeneous population of nucleus pulposus cells is obtained from a biopsy specimen of nucleus pulposus by treating nucleus pulposus tissue with a Collagenase solution (Example 1). In another embodiment, a heterogeneous population of nucleus pulposus cells is obtained from a biopsy specimen of nucleus pulposus by treating nucleus pulposus with a 0.1%-1% clostridial Collagenase (Worthington CLS II, 140 u/mg).

In another embodiment, a heterogeneous population of nucleus pulposus cells is obtained from a biopsy specimen of nucleus pulposus by aspiration of a disc of a subject. In another embodiment, a heterogeneous population of nucleus pulposus cells is obtained from a biopsy specimen of nucleus pulposus cells by aspiration through a cannula, which in one embodiment, is part of a surgery, and in another embodiment, is percutaneous. In another embodiment, a heterogeneous population of nucleus pulposus cells is obtained from a biopsy specimen of the nucleus pulposus tissue obtained from surgical resection, which in one embodiment comprises surgery to gain exposure to the disc and then resection of tissue.

In one embodiment, said subject is a patient. In another embodiment, said subject is a human. In another embodiment, said subject is an animal. In one embodiment, said nucleus pulposus cells are from healthy tissue. In another embodiment, said nucleus pulposus cells are from degenerated tissue.

In another embodiment, a heterogeneous population of nucleus pulposus cells is obtained from a biopsy specimen of nucleus pulposus by aspiration of a disc of a donor animal. In another embodiment, a heterogeneous population of nucleus pulposus cells is obtained from a biopsy specimen of nucleus pulposus by aspiration of a nucleus pulposus of a donor mammal. In another embodiment, a heterogeneous population of nucleus pulposus cells is obtained from a biopsy specimen of nucleus pulposus by aspiration of a healthy disc of a patient.

In one embodiment, the nucleus pulposus cells are human nucleus pulposus cells. In another embodiment, the nucleus pulposus cells are mammalian nucleus pulposus cells. In another embodiment, the nucleus pulposus cells are isolated from degenerated disc tissue. In another embodiment, the nucleus pulposus cells are isolated from healthy disc tissue. In one embodiment, the nucleus pulposus cells are isolated from fetal, neonatal, or young adult tissue.

Therefore, in one embodiment, the present invention provides a method of amplifying a population of nucleus pulposus cells comprising the steps of: (a) suspending isolated nucleus pulposus cells in a medium comprising serum, basic fibroblast growth factor (bFGF), epidermal growth factor (EGF), human neonatal foreskin fibroblast (NFF) cell supernatant, or a combination thereof; and (b) plating the suspension onto adherent tissue culture plates, thereby amplifying a population of nucleus pulposus cells. In one embodiment, the adherent tissue culture plate is a gelatin-coated tissue culture plate.

In another embodiment, the present invention provides a method of amplifying a population of nucleus pulposus cells comprising the steps of: (a) suspending isolated nucleus pulposus cells in a medium comprising approximately 14-15% serum, basic fibroblast growth factor (bFGF), epidermal growth factor (EGF), and 30-40% human neonatal foreskin fibroblast (NFF) cell supernatant; and (b) plating the suspension onto gelatin-coated tissue culture plates for 5-14 days, thereby amplifying a nucleus pulposus cell population. In one embodiment, said cells grow as an attached monolayer on said gelatin-coated tissue culture plates.

In one embodiment, said tissue culture plates are coated with 0.1% gelatin.

In one embodiment, the media comprising serum and NFF cell supernatant is referred to herein as "Discotek" medium. In another embodiment, Discotek medium comprises EGF and FGF2.

In one embodiment, a medium for use in the methods of the present invention comprises Dulbecco's Modified Eagles Medium (DMEM). In another embodiment, a medium for use in the methods of the present invention comprises DMEM/F12. In another embodiment, a medium for use in the methods of the present invention comprises DF10. In another embodiment, a medium for use in the methods of the present invention comprises Hamm's culture media. In another embodiment, a medium for use in the methods of the present invention comprises Hamm's/F12 culture media.

In another embodiment, a medium for the methods of the present invention is supplemented with serum which in one embodiment is fetal bovine serum (FBS). In another embodiment, the serum is fetal calf serum (FCS). In one embodiment, the concentration of serum is 8-20%. In another embodiment, the concentration of serum is 15%. In another embodiment, the concentration of serum is 5%. In another embodiment, the concentration of serum is 6%. In another embodiment, the concentration of serum is 10%. In another embodiment, the concentration of serum is 14%. In another embodiment, the concentration of serum is 6-10%. In another embodiment, the concentration of serum is 5-10%. In another embodiment, the concentration of serum is 14.5%. In another embodiment, the concentration of serum is 13-16%. In another embodiment, the concentration of serum is 11-20%. In another embodiment, the concentration of serum is 14-15%. In another embodiment, the concentration of serum is greater than 10%. In another embodiment, the concentration is approximately the percentages described hereinabove. In one embodiment, fetal bovine serum, NFF, fetal calf serum, DF10, or a combination thereof is a source of serum.

In another embodiment, the medium comprises NIT conditioned media. In one embodiment, NIP are cultured in DF10 medium, and supernatant is collected every 2 days, and frozen or used in a medium of the present invention as described herein. In one embodiment, the medium comprises 33% media derived from cultures of primary NFFs. In another embodiment, the medium comprises 30-70% media derived from cultures of primary NFFs. In another embodiment, the medium comprises 30-35% media derived from cultures of primary NFFs. In another embodiment, the medium comprises 30-40% media derived from cultures of primary NFFs. In another embodiment, the medium comprises 25-50% media derived from cultures of primary NFFs.

In one embodiment, the nucleus pulposus cells demonstrate a notochordal cell morphology, a notochordal-like phenotype, or a combination thereof. In one embodiment, notochord cells with the distinctive morphology described herein and in the literature is observed during the culture, but not when isolating cells from the culture. In one embodiment, the morphology of notochordal cells changes (becoming, in one embodiment, indistinct, difficult to identify, and similar to nucleus pulposus cells) under the conditions to which the cells are exposed. However, notochordal cells are still present, as is known in the art.

In one embodiment, said nucleus pulposus cells comprise chondrocyte-like cells. In another embodiment, said nucleus pulposus cells comprise notochordal-like cells, which in one embodiment are larger than chondrocyte-like cells, contain large vacuoles, and express proteins and other macromolecules important for disc cellular and structural biology. In another embodiment, said nucleus pulposus cells comprise notochordal-like cells, which in one embodiment, have heterogeneous morphology that vary according to culture conditions and can be identified using molecular probes. In another embodiment, said nucleus pulposus cells comprise disc stem cells or nucleus pulposus stem cells. In one embodiment, depletion of notochordal cells correlates with the onset of disc degeneration. In one embodiment, a prolonged loss of notochord cells in the disc tissue correlates with an increased degree of disc degeneration. In one embodiment, notochordal cells comprise disc stem cells. In one embodiment, said nucleus pulposus cells comprise disc stem cells, disc progenitor cells, mature disc cells, terminally differentiated disc cells, notochordal cells, or a combination thereof.

In one embodiment, nucleus pulposus cells derived directly from tissue preparations are grown until confluent, at which time they are passaged into the sphere culture. In one embodiment, cells are passaged when they are 90% confluent. In another embodiment, cells are passaged when they are 70% confluent. In another embodiment, cells are passaged when they are 75% confluent. In another embodiment, cells are passaged when they are 80% confluent. In another embodiment, cells are passaged when they are 100% confluent.

In one embodiment, cells reach confluency in 3-5 days. In one embodiment, cells reach confluency in 5-7 days. In one embodiment; cells reach confluency in 4-7 days. In another embodiment, cells reach confluency in 3-10 days. In another embodiment, cells reach confluency in 10-12 days. In another embodiment, cells reach confluency in 7-14 days. In another embodiment, cells reach confluency in 10-20 days. In another embodiment, cells reach confluency after 20 days. In another embodiment, cells reach confluency in 10-20 days. In another embodiment, cells reach confluency in 8-16 days.

In one embodiment, the nucleus pulposus cells reach 70% confluency after a 3-5 day incubation. In another embodiment, nucleus pulposus cells reach 100% confluency after a 5-7 day incubation. In another embodiment, nucleus pulposus cells reach 100% confluency after 7-14 days.

In one embodiment, cells are passaged by incubating them with Collagenase, which in one embodiment is Collagenase II. In one embodiment, cells are incubated with Collagenase II overnight. In another embodiment, cells are incubated with Collagenase II for 1 hour. In another embodiment, cells are incubated with Collagenase II for 2 hours. In another embodiment, cells are incubated with Collagenase II for 4 hours. In another embodiment, cells are incubated with Collagenase II for 8 hours. In another embodiment, cells are incubated with Collagenase II for 12 hours. In another embodiment, cells are incubated with Collagenase II for 16 hours. In another embodiment, cells are incubated with Collagenase II for 24 hours. In one embodiment, the Collagenase is nucleolysin. In another embodiment, cells are incubated with chymopapain.

In one embodiment, methods of the present invention may comprise an incubation step wherein cells are incubated at 37° C. In another embodiment, cells are incubated at 35° C.-37° C. In another embodiment, cells are incubated at 33° C.-39° C. In another embodiment, cells are incubated at 37° C. In another embodiment, cells are incubated at 35° C. In another embodiment, cells are incubated at 36° C. In another embodiment, cells are incubated at 38° C. In another embodiment, cells are incubated at 39° C. In another embodiment, cells are incubated at 40° C. In another embodiment, cells are incubated at 41° C. In another embodiment, cells are incubated at 42° C.

In one embodiment, cells are incubated in an incubator maintaining 3-8% $CO_2$. In another embodiment, cells are incubated in an incubator maintaining 4% $CO_2$. In another embodiment, cells are incubated in an incubator maintaining 5% $CO_2$. In another embodiment, cells are incubated in an incubator maintaining 6% $CO_2$.

In one embodiment, cells are incubated under hypoxic conditions, which in one embodiment comprises maintaining 2% $O_2$ in the incubator. In another embodiment, cells are incubated under normoxic conditions, which in one embodiment comprises maintaining 20% $O_2$ in the incubator.

In one embodiment, cells are incubated in an incubator maintaining 60% humidity. In another embodiment, cells are incubated in an incubator maintaining 70% humidity. In another embodiment, cells are incubated in an incubator maintaining 80% humidity. In another embodiment, cells are incubated in an incubator maintaining 90% humidity. In another embodiment, cells are incubated in an incubator maintaining 95% humidity.

In one embodiment, said nucleus pulposus cells are plated at high density for, in one embodiment, attachment culture. In one embodiment, said nucleus pulposus cells are plated at a cell surface density of 50,000 cells/cm$^2$. In another embodiment, said nucleus pulposus cells are plated at a cell surface density of 40,000 cells/cm$^2$. In another embodiment, said nucleus pulposus cells are plated at a cell surface density of 60,000 cells/cm$^2$. In another embodiment, said nucleus pulposus cells are plated at a cell surface density of 30,000 cells/cm$^2$. In another embodiment, said nucleus pulposus cells are plated at a cell surface density of 70,000 cells/cm$^2$. In another embodiment, said nucleus pulposus cells are plated at a cell surface density of between 30,00070,000 cells/cm$^2$. In another embodiment, said nucleus pulposus cells are plated at a cell surface density of between 40,000-60,000 cells/cm$^2$. In another embodiment, said nucleus pulposus cells are plated at a cell surface density of between 45,000-55,000 cells/cm$^2$. In another embodiment, said nucleus pulposus cells are plated at a cell surface density of between 49,000-51,000 cells/cm$^2$.

In one embodiment, cells of the present invention are suspended at low density for, in one embodiment, sphere culture and, in another embodiment, for cluster culture. In one embodiment, cells are suspended at a final density of approximately $1 \times 10^4$ cells/ml. In another embodiment, cells are suspended at a final density of approximately $5 \times 10^4$ cells/ml. In another embodiment, cells are suspended at a final density of approximately $2 \times 10^4$ cells/ml. In another embodiment, cells are suspended at a final density of approximately $2 \times 10^5$ cells/ml. In another embodiment, cells are suspended at a final density of approximately $1 \times 10^5$ cells/ml. In another embodiment, cells are suspended at a final density of approximately $1 \times 10^3$ cells/ml. In another embodiment, cells are suspended at a final density of approximately $5 \times 10^3$ cells/ml. In another embodiment, cells are suspended at a final density of approximately $5 \times 10^5$ cells/ml. In another embodiment, cells are suspended at a final density of approximately $1 \times 10^6$ cells/ml. In another embodiment, cells are suspended at a final density of approximately $5 \times 10^5$ cells/ml. In another embodiment, cells are suspended at a final density of approximately $8 \times 10^4$ cells/ml. In another embodiment, cells are suspended at a final density of approximately $6 \times 10^4$ cells/ml.

In another embodiment, the present invention further provides that disc stem cells are grown in a medium comprising a compound that maintains cell juvenility or immaturity. In another embodiment, the present invention further provides that disc stem cells are grown in a medium comprising a compound which inhibits cell maturation. In another embodiment, the present invention further provides that disc stem cells are grown in a medium comprising FOP which inhibits cell maturation. In another embodiment, the present invention further provides that disc stem cells are grown in a medium comprising a compound that inhibits cell differentiation.

In one embodiment, any medium of the present invention is supplemented with Fibroblast growth factor (FGF), which in one embodiment is fibroblast growth factor-2 (FGF-2), which in one embodiment, is also known as basic Fibroblast Growth Factor (bFGF) or FGF-β. In another embodiment, the medium comprises 1-100 ng/ml FGF2. In another embodiment, the medium comprises 20-50 ng/ml FGF2. In another embodiment, the medium comprises 50-100 ng/ml FGF2. In another embodiment, the medium comprises 5-15 ng/ml FGF2. In another embodiment, the medium comprises 8-12 ng/ml FGF2. In another embodiment, the medium comprises 10 ng/ml FGF2.

In another embodiment, the present invention further provides that disc stem cells are grown in a medium comprising a compound that promotes stem cell or precursor cell proliferation.

In one embodiment, a medium of the present invention is supplemented with epidermal growth factor (EGF). In another embodiment, a medium of the present invention comprises 1-10 ng/ml EGF. In another embodiment, the medium comprises 1-100 ng/ml EGF. In another embodiment, the medium comprises 20-50 ng/ml EGF. In another embodiment, the medium comprises 50-100 ng/ml EGF. In another embodiment, the medium comprises 5-15 ng/ml EGF. In another embodiment, the medium comprises 8-12 ng/ml EGF. In another embodiment, the medium comprises 10 ng/ml EGF.

In one embodiment, disc stem cells are grown in a medium of the present invention lacking heparin.

In another embodiment, the present invention further provides that disc stem cells are grown in a medium comprising interleukin-2 (IL-2). In another embodiment, the present invention further provides that disc stem cells are grown in a medium comprising interleukin-6 (IL-6). In another embodiment, the present invention further provides that disc stem cells are grown in a medium comprising a stem cell factor (SCF).

In another embodiment, the present invention further provides that disc stern cells are grown in a medium comprising transforming growth factor-β (TGF-β), which in one embodiment is TGFβ1 or TGFβ3. In another embodiment, the present invention further provides that disc stern cells are grown in a medium comprising a TGF-β superfamily member. In another embodiment, the present invention further provides that disc stem cells are grown in a medium comprising a BMP, which in one embodiment is BMP2, BMP4, or BMP7. In another embodiment, the present invention further provides that disc stem cells are grown in a medium comprising a BMP superfamily member. In another embodiment, the present invention further provides that disc stem cells are grown in a medium comprising an IL6 cytokine family member, which in one embodiment, is leukemia inhibitory factor (LIF).

In some embodiments of the invention, a medium is supplemented with fibronectin at about 0.0001 to about 1 mg/ml. In some embodiments of the invention, the medium is supplemented with TGF-β at about 10 picograms/ml to about 10,000 picograms/ml, and more preferably at about 100 picograms/ml to about 1000 picograms/ml; with PDGF at about 1.0 ng/ml to about 10,000 ng/ml, and more preferably at about 10 ng/ml to about 1000 ng/ml.

In some embodiments, biologically active molecules are included in a medium of the present invention. In one embodiment, the biologically active molecules comprise growth factors, cytokines, antibiotics, proteins, anti-inflammatory agents, or a combination thereof. In one embodiment, the biologically active molecules comprise TFG-beta, PDGF, EGF, FGF, IL-1 and IL-6.

In one embodiment, the medium is replenished every two days. In another embodiment, the medium is replenished every day. In another embodiment, the medium is replenished every three days. In another embodiment, the medium is replenished every four days. In another embodiment, the medium is replenished 2-3 times per week.

In one embodiment, the growth and development of the cells are monitored by the removal of an aliquot of the culture approximately every two days and determining the DNA content of the cells. In one embodiment, the degree of active proliferation by cells in culture is determined by determining DNA content. In one embodiment, the DNA content is determined by PI staining, FACS analysis, or a combination thereof. In one embodiment, DNA content is reflective of the S phase (1-2×DNA complement) or G2 phase (2× complement) of cell cycling, or one of the other phases (1×DNA complement). In another embodiment, the growth and development of the cells are monitored by the removal of an aliquot of the culture and performing a cell count.

In one embodiment, any method of the present invention further comprises the step of cryopreserving the cells produced by one of the methods described herein. In one embodiment, two thirds of the total cell population is cryopreserved. In one embodiment, cells are cryopreserved at 3M cells/ml, in one embodiment, in 1 ml aliquots. In one embodiment, cells are cryopreserved in Discotek media. In one embodiment, cryopreserved cells are used to generate stem cells, and, in another embodiment, cryopreserved cells are used at a later time for experiments. In one embodiment, cells are cryopreserved at −20° C. In another embodiment, cells are cryopreserved at −70° C.-80° C. In one embodiment, the cells may be cooled or frozen during storage to a temperature about or below 4° C. to about −196° C. In one embodiment, ultrarefined arabinogalactan is provided in the cryopreservation medium, optionally in combination with a second cryopreservation agent, such as dimethyl sulfoxide, in one embodiment, to protect the viability of cells in the medium during the process of freezing, storage and thawing.

In one embodiment, the step of cryopreserving comprises suspending cells in 10% DMSO plus 90% serum. In one embodiment, the step of cryopreserving comprises aliquoting the mixture and placing the mixture into a cryopreservation vessel, which, in one embodiment is a structure to hold the vials, set within another vessel filled with isopropanol. In one embodiment, the step of cryopreserving comprises slowly freezing the cells to a temperature of −80° C. In one embodiment, the step of cryopreserving comprises transferring the cells to liquid nitrogen the day following the step of freezing the cells.

In one embodiment, any method of the present invention further comprises the step of preparing a single-cell suspension from the tissue or cell monolayer or cellular aggregates produced by the method. In one embodiment, cells are passaged by preparing a single cell suspension. In one embodiment, enzymatic digestion is used to prepare the single cell suspension.

In one embodiment, enzymatic digestion is used to create a single cell suspension between each culturing step in the methods of the present invention. In one embodiment, tissue is procured, digested with Collagenase II for 24 hours, then the single cell preparation is plated in the attachment culture. Then, at confluency, the attachment culture is prepared as a single cell suspension with Trypsin, and plated in the sphere culture. Then, at maturity, the sphere culture is digested with Trypsin, and plated as a single cell suspension into the cluster culture. In another embodiment, an alternative path is to transfer the sphere culture stem cell spheres directly to the cluster culture. In another embodiment, the sphere culture and the cluster culture can be cycled within themselves up to three times, by creating a single cell suspension with Trypsin, and replating in the same culture system. In one embodiment, cells are expanded by around 1:3 ratios.

In one embodiment, the attachment culture method is only used once for expansion of the cell populations. In one embodiment, if the cells are cycled repeatedly through the attachment culture method, the differentiation-driving aspects of the culture system (which, in one embodiment, comprise attachment and serum) overwhelm the pro-stem aspects of the culture system, leading, in one embodiment, to differentiation of the rare stem cell populations into other cell types.

The present inventors have made the unexpected discovery that disc stem cells may be successfully isolated from disc tissue and maintained in culture as disc stem cells when, in one embodiment, the cells are plated in low density in non-attachment culture plates in the presence of methylcellulose to prevent or minimize contact with other cells (e.g. stem cells, other cell types) and/or contact with any surface of the culture vessel. In one embodiment, these contacts may lead to or induce differentiation.

In one embodiment, cells are then suspended in media mixed 1:1 with methylcellulose and culture media/supplemental reagents at low density ($1\times10^4$ cells/ml on tissue culture plates with ultra-low binding surfaces) such that the cells float and have no attachment to any surface. This procedure, when combined with low density plating, allows disc stem cells to grow in isolation into monoclonally derived stem cell and progenitor cell clusters. In fact, only stem cells can grow in these conditions, whereas mature disc cells (nucleus pulposus cells) or late stage progenitors do not survive without attachment. The cells are then cultured from 12-16 days, while the media is changed every 2-3 days.

The method of the present invention allows disc stem cells to grow symmetrically or clonally to produce other disc stem cells. Specifically, the plated disc stem cells floating in media clonally divide and replicate themselves at a rate of division that is much higher than the rate of symmetric division of stem cells in vivo in the natural tissue environment. As the disc stem cells divide, they slowly grow in size as a cluster of cells tightly attached to each other through cell to cell contact, which, in one embodiment, occurs through the secondary secretion of extracellular matrix molecules (ECMs) (e.g. collagen, aggrecan, proteoglycans, etc.) that intercalate between the cells and around the aggregated cell body. ECMs typically have a cement-like effect when secreted and remodeled in between two cells already in contact, or at least in close proximity.

These cell clusters are roughly spherical in shape, and, typically, the outer layers are more differentiated. In one embodiment, these spherical cell clusters are referred to herein as "discospheres". In one embodiment, cells in a single discosphere that is in culture are derived from the first isolated disc stem cell that was plated initially. This clonal growth, also known as symmetric growth, is, in one embodiment, a characteristic feature of disc stem cells, and, in another embodiment, is one of the criteria that define a disc stem cell. In another embodiment, a discosphere of the present invention is the result of stem cell proliferation which gives rise to additional stem cells and progenitor cells. In another embodiment, a discosphere is formed as a result of disc stem cell proliferation.

In another embodiment, disc stem cells of the present invention proliferate thus forming a discosphere. In another embodiment, a discosphere of the present invention comprises nucleus pulposus stem cells and nucleus pulposus progenitor cells arranged in a circular-spherical structure. In another embodiment, a discosphere is a ball of cells in which a single disc stem cell gives rise to clones of itself (symmetric division) and to progenitor cells. In another embodiment, a discosphere of the present invention comprises free floating nucleus pulposus stem cells and nucleus pulposus progenitor cells arranged in a circular-spherical structure. In another embodiment, a discosphere comprises nucleus pulposus cells that are attached to one another.

In one embodiment, the term "progenitor cells" refer to immature stem-like cells with plastic potential and high proliferation rates, which can give rise to most if not all terminally differentiated tissue cells, but is not a disc stem cell.

In another embodiment, the present invention provides a method of producing an enriched disc stem cell population from nucleus pulposus cells comprising the steps of (a) suspending a nucleus pulposus cell population in a medium comprising methylcellulose, fetal calf serum (FCS), basic fibroblast growth factor (bFGF), epidermal growth factor (EGF), or a combination thereof; and (b) distributing the suspension onto ultra-low binding culture plates, thereby producing an enriched disc stem cell population.

In another embodiment, the present invention provides a method of producing an enriched disc stem cell population from nucleus pulposus cells comprising the steps of (a) suspending a nucleus pulposus cell population in a medium comprising >10% methylcellulose, fetal calf serum (FCS), basic fibroblast growth factor (bFGF), and epidermal growth factor (EGF); and (b) distributing the suspension onto ultra-low binding culture plates, wherein an individual disc stem cell grows into a sphere-like cell cluster in a clonal manner, thereby producing an enriched disc stem cell population.

In another embodiment, the present invention provides a method of producing an enriched disc stem cell population from nucleus pulposus cells comprising the steps of: (a) suspending nucleus pulposus cell population in a medium comprising >10% methylcellulose, 5-10% serum, basic fibroblast growth factor (bFGF), and epidermal growth factor (EGF); (b) distributing the suspension onto ultra-low binding culture plates; and (c) growing said suspension for 10-20 days, wherein an individual disc stem cell grows into a sphere-like cell cluster in a clonal manner, thereby producing an enriched disc stem cell population.

In another embodiment, the present invention provides a method of producing an enriched disc stem cell population from nucleus pulposus cells comprising the steps of: (a) suspending a nucleus pulposus cell population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) growing said single cell suspension for 10-20 days, wherein an individual disc stem cell grows into a sphere-like cell cluster in a clonal manner, thereby producing an enriched disc stem cell population.

In another embodiment, the method described directly hereinabove is a method of producing a disc tissue-derived clonal stem cell population.

In one embodiment, a cell population comprises a multiplicity of cells of heterogeneous cell types. In another embodiment, a cell population comprises a multiplicity of cells of a single cell type. In one embodiment, a nucleus pulposus cell population comprises one or more disc stem cell types.µ

In one embodiment, the step of suspending a cell population comprises suspending individual cells in a liquid medium of varying degrees of viscosity. In another embodiment, the step of suspending a cell population comprises suspending single cells in a liquid medium of varying degrees of viscosity.

In one embodiment, the media comprises DMEM/F12 media. In another embodiment, the media comprises N2 Media. In another embodiment, the media comprises DMEM/F12 and N2 Media.

In another embodiment, the present invention provides a media for differentiation of disc stem cells, which in one embodiment, comprises one or more differentiation or pro-chondrogenic agents, which in one embodiment, are BMP2, BMP7, TGFB1, TGFB3, dexamethasone, or a combination thereof.

In another embodiment, the present invention provides a composition comprising a discosphere. In another embodiment, a composition of the present invention comprises a single discosphere. In another embodiment, a composition of the present invention comprises at least $1 \times 10^2$ discospheres. In another embodiment, a composition of the present invention comprises at least $1 \times 10^3$ discospheres. In another embodiment, a composition of the present invention comprises at least $1 \times 10^4$ discospheres. In another embodiment, a composition of the present invention comprises at least $1 \times 10^5$ discospheres. In another embodiment, a composition of the present invention comprises at least $1 \times 10^6$ discospheres.

In another embodiment, the present invention provides that discospheres obtained by the methods of the present invention are further expanded. In another embodiment, the present invention provides that discospheres are dissociated by incubation at 37° C. in Trypsin. In another embodiment, the present invention provides that the dissociated cells are expanded by replating the same into methylcellulose-based stem cell medium and culture vessel as described hereinabove.

In one embodiment, the media for growing disc stem cells comprises methylcellulose. In one embodiment, the media for growing disc stem cells comprises >5% methylcellulose. In one embodiment, the media for growing disc stem cells comprises >3% methylcellulose. In one embodiment, the media for growing disc stem cells comprises >2% methylcellulose. In another embodiment, the media for growing disc stem cells comprises 50% methylcellulose. In another embodiment, the media for growing disc stem cells comprises >10% methylcellulose. In another embodiment, the media for growing disc stem cells comprises >25% methylcellulose. In another embodiment, the media for growing disc stem cells comprises >40% methylcellulose. In another embodiment, the media for growing disc stem cells comprises 45-55% methylcellulose. In another embodiment, the media for growing disc stem cells comprises 40-60% methylcellulose. In another embodiment, the media for growing disc stem cells comprises 30-70% methylcellulose.

In another embodiment, the method described hereinabove provides two distinct sphere-shaped cellular products. In one embodiment, one sphere-shaped cellular product is a nucleus pulposus sphere, and in one embodiment, a second sphere-shaped cellular product is a notochordal stem cell sphere.

In one embodiment, clonal refers to a group of cells that are derived from a single cell and share many or all of its characteristics.

In one embodiment, the number of cells within a stem cell sphere and the size of a stem cell sphere vary. In one embodiment, the number of cells of a mature sphere is approximately 250 cells. In another embodiment, the number of cells of a mature sphere is approximately 100 cells. In another embodiment, the number of cells of a mature sphere is approximately 500 cells. In another embodiment, the number of cells of a mature sphere is approximately 100-500 cells. In another embodiment, the number of cells of a mature sphere is approximately 200-300 cells.

In one embodiment, the outer or peripheral layer of the sphere tends to be somewhat more differentiated than the inner or core portion of the sphere, as is described herein (Example 4).

In another embodiment, the disc stem cells are plated on ultra low attachment plates in the methods of the present invention. In another embodiment, the disc stem cells are plated on ultra low attachment precoated with an anti-adhesive substance plates in the methods of the present invention. In another embodiment, the anti-adhesive substance is poly 2-hydroxyethyl methacrylate.

In one embodiment, disc stem cells produced by a method of the present invention express cytokeratin-8 (CK-8), CD-133, Nestin, and OCT-4.

In one embodiment, MMPs, ADAMTSs, and TIMPs are differentially expressed by chondrocytes and NP cells. In one embodiment, NP cells express higher levels of MMP-2, MMP-14, ADAMTS-1,-2,-17 and TIMP-1 than chondrocytes. In another embodiment, NP cells express lower levels of MMP-1,-3,-7,-8,-10,-11,-13,-16,-19,-20,-21,-23,-24,-28, ADAMTS-4,-5,-6,-14,-18,-19, and TIMP-3 than chondrocytes. In another embodiment, chondrocytes but not NP cells express MMP12 and MMP27.

In one embodiment, the method further comprises the step of cryopreserving the sphere-like cell cluster (in one embodiment the discosphere) or cells isolated from the sphere-like cell cluster.

When the discospheres reach a certain size, they need to be passaged to maintain continued health and viability of the disc stem cell population. Passaging involves collating all cultured discospheres into a tube, washing and treating the cells with enzymes to break cell to cell contacts, and gentle pipetting of the cell pellet to break up clumps and create single cell suspensions enriched in disc stem cells (70-90% disc stem cells and early progenitors). The cells are counted at this time to assess growth. The disc stem cells thus obtained may be analyzed or cryopreserved directly, or converted back into single cell suspensions and replated to continue their expansion in vitro. This cycle can continue indefinitely to expand the disc stem cell population, such that one cell can be expanded into 50 to 400 cells, in one embodiment. The cells may be further expanded by a third passage for cryopreservation, cell and molecular assays or in vitro, and in vivo tissue-engineering applications.

in another embodiment, the present invention provides a method of amplifying an enriched disc stem cell population comprising the steps of: (a) suspending a sphere-like cluster of disc stem cells or an isolated disc stem cell from said sphere-like cell cluster in a medium comprising fetal calf serum (FCS), basic fibroblast growth factor (bFGF), epidermal growth factor (EGF), or a combination thereof and lacking methylcellulose; and (b) distributing the suspension onto ultra-low binding culture plates, thereby amplifying an enriched disc stem cell population.

In another embodiment, the present invention provides a method of amplifying and further enriching an enriched disc stem cell population comprising the steps of: (a) suspending a sphere-like cluster of disc stem cells or an isolated disc stem cell from said sphere-like cell cluster in a medium comprising fetal calf serum (FCS), basic fibroblast growth factor (bFGF), and epidermal growth factor (EGF) and lacking methylcellulose; and (b) distributing the suspension onto ultra-low binding culture plates, wherein said cluster or cell grows into a large aggregate cellular cluster of heterogeneous morphology, thereby amplifying and further enriching an enriched disc stem cell population.

In another embodiment, the present invention provides a method of amplifying and further enriching an enriched disc stem cell population comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (EGF) and lacking methylcellulose; (b) distributing the suspension onto ultra-low binding culture plates; (c) growing said suspension for 8-16 days, wherein said cluster or cell grows into a large aggregate cluster of heterogeneous morphology, thereby amplifying and further enriching an enriched disc stem cell population.

In another embodiment, the present invention provides a method of amplifying and further enriching an enriched disc stem cell population comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (EGF); (b) distributing the suspension onto ultra-low binding culture plates; (c) growing said suspension for 8-16 days, wherein said cluster or cell grows into a large aggregate cluster of heterogeneous morphology, thereby amplifying and further enriching an enriched disc stem cell population.

In one embodiment, the medium as described hereinabove lacks methylcellulose.

In another embodiment, the method described directly hereinabove is a method of producing a disc tissue-derived heterogeneous stem cell population.

In one embodiment, the media comprises DMEM/F12 media. In another embodiment, the media comprises N10 Media. In another embodiment, the media comprises DMEM/F12 and N10 Media.

In one embodiment, the media further comprises putrescine, progesterone, sodium selenite, transferrin, insulin, or a combination thereof. In another embodiment, the media further comprises putrescine, progesterone, sodium selenite, transferrin, and insulin.

In one embodiment, N2 OR N10 media comprises DMEM F12 Media. In one embodiment, N2 or N10 media comprises Sodium Selenite, which in one embodiment is present in the media at a concentration of 30 μM. In another embodiment, the media comprises Sodium Selenite at a concentration of 20-40 μM. In another embodiment, the media comprises Sodium Selenite at a concentration of 10-50 μM. In another embodiment, the media comprises Sodium Selenite at a concentration of 10-100 μM. In another embodiment, the media comprises Sodium Selenite at a concentration of 25-35 μM.

In one embodiment, N2 OR N10 media comprises Insulin, which in one embodiment is present in the media at a concentration of 5 μg/ml. In another embodiment, the media comprising disc stem cells further comprises 1-100 μg/ml insulin. In another embodiment, the media comprising disc stem cells further comprises 1-10 μg/ml insulin. In another embodiment, the media comprising disc stem cells further comprises 1-50 μg/ml insulin. In another embodiment, the media comprising disc stem cells further comprises 5-15 μg/ml insulin. In another embodiment, the media comprising disc stem cells further comprises 8-12 μg/ml insulin.

In one embodiment, N2 OR N10 media comprises Putrescine, which in one embodiment is present in the media at a concentration of 100 μM. In another embodiment, the media comprises Putrescine at a concentration of 1-200 μM. In another embodiment, the media comprises Putrescine at a concentration of 1-500 μM. In another embodiment, the media comprises Putrescine at a concentration of 50-150 μM. In another embodiment, the media comprises Putrescine at a concentration of 100-200 μM. In another embodiment, the media comprises Putrescine at a concentration of 10-100 μM. In another embodiment, the media—comprises Putrescine at a concentration of 75-125 μM.

In one embodiment, N2 OR N10 media comprises Progesterone, which in one embodiment is present in the media at a concentration of 20 μM. In another embodiment, the media comprises Progesterone at a concentration of 10-30 μM. In another embodiment, the media comprises Progesterone at a concentration of 1-50 μM. In another embodiment, the media comprises Progesterone at a concentration of 15-25 μM. In another embodiment, the media comprises Progesterone at a concentration of 10-50 μM. In another embodiment, the media comprises Progesterone at a concentration of 10-100 μM.

In one embodiment, N2 OR N10 media comprises Transferrin, which in one embodiment is present in the media at a concentration of 50 μg/ml. In another embodiment, the media comprising disc stem cells further comprises 1-400 μg/ml transferrin. In another embodiment, the media comprising disc stem cells further comprises 1-100 μg/ml transferrin. In another embodiment, the media comprising disc stem cells further comprises 20-150 μg/ml transferrin. In another embodiment, the media comprising disc stem cells further comprises 25-75 μg/ml transferrin. In another embodiment, the media comprising disc stem cells further comprises 40-60 μg/ml transferrin.

In one embodiment, N10 media further comprises serum, which in one embodiment is fetal calf serum. In another embodiment, the serum is fetal bovine serum.

In one embodiment, said media comprises 10% serum. In one embodiment, said FGF-2 is present in the media at a concentration of 10 ng/ml. In one embodiment, said EGF is present in the media at a concentration of 10 ng/ml. In one embodiment, said suspension is distributed at a density of $1 \times 10^4$ cell/ml. In one embodiment, said suspension reaches confluency after approximately 10 days in culture.

In one embodiment, the method further comprises the step of cryopreserving the large cluster of heterogeneous morphology or cells isolated from the heterogeneous cluster.

In one embodiment, a method of the present invention further comprises the step of producing a single cell suspension from a sphere-like disc stem cell cluster or a heterogeneous cluster using enzymatic digestion prior to the step wherein a single cell is suspended in a medium as described herein.

In one embodiment, a method of the present invention further comprises the step of identifying disc stem cell markers and separating disc stem cells from disc progenitors and/or other cells present. According to this aspect and in one embodiment, a method of the present invention further comprises the step of sorting cells using biomarkers. In one embodiment, FACS is used to sort cells. In another embodiment, magnetic-activated cell sorting (MACS) is used to sort cells, which in one embodiment, is a technique in which cells are sorted using a column with magnetic beads, wherein antibodies that bind the marker on stem cells are incubated with said stem cells, and then the solution is filtered through the column where the antibody-biomarker-cell are picked up by the beads, and the other cells flush through the column, and then the stem cells are eluted. In another embodiment, a reporter gene that is genetically engineered to be regulated by the biomarker's promoter is used to sort cells. In one embodiment, an example of a reporter gene that is genetically engineered to be regulated by the biomarker's promoter is OCT-4-GFP described hereinbelow. In one embodiment, CD133 is used for FAGS and MACS. In one embodiment, OCT-4, CD133, and CK8 promoters are engineered upstream of a reporter gene known in the art for use in the method of cell sorting described hereinabove.

In one embodiment, the methods described hereinabove are combined in a method of producing an enriched and amplified disc cell population.

According to this aspect and in one embodiment, the present invention provides a method of producing an amplified and enriched disc stem cell population comprising the steps of: (a) growing isolated nucleus pulposus cells in a first culture comprising a medium comprising serum and human neonatal foreskin fibroblast (NFF) cell supernatant, and plated on gelatin-coated tissue culture plates to allow attachment and growth as a monolayer; (b) creating a single cell suspension of nucleus pulposus cells from said first culture; (c) growing disc stem cells isolated from said first culture in a second culture comprising a medium comprising methylcellulose, and plating as a suspension on ultra-low binding culture plates, wherein individual disc stem-cells grow into cellular clusters of a spherical shape; (d) isolating a population of disc stem cells from said second culture; and (e) growing disc stem cells or disc stem spheres isolated from said second culture in a third culture comprising a medium lacking methylcellulose, and plating the cells as a suspension on ultra-low binding culture plates, wherein individual disc stem cells form aggregate clusters of heterogeneous morphology; and (f) isolating a population of disc stem cells from said third culture, thereby producing an amplified and enriched disc cell population. In one embodiment, said first culture is attachment culture. In one embodiment, said second culture is discosphere or sphere culture. In one embodiment, said third culture is cluster culture.

In one embodiment, the medium of step (a) comprises NFF supernatant. In one embodiment, the medium of steps (a), (c), and (e) comprise basic fibroblast growth factor (bFGF), epidermal growth factor (EGF), or a combination thereof. In one embodiment, the medium of steps (a), (c), and (e) comprise serum, which in one embodiment, is fetal bovine serum (FBS).

In another embodiment, the present invention provides a method of producing an amplified and enriched disc stem cell population comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a population of nucleus pulposus cells from said first medium; (c) growing said nucleus pulposus cells in a second medium comprising methylcellulose, serum, basic fibroblast growth factor (bFGF), and epidermal growth factor (EGF) on ultra-low binding culture plates to confluency; (d) isolating a population of disc stem cells from said second medium; (e) growing said disc stem cells in suspension in a third medium comprising serum, basic fibroblast growth factor (bFGF), and epidermal growth factor (EGF) and lacking methylcellulose on ultra-low binding culture plates to confluency; and (f) isolating a population of disc stem cells from said third medium, thereby producing an amplified and enriched disc stem cell population.

In another embodiment, the present invention provides a method of producing an amplified and enriched disc stem cell population comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) growing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) growing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, thereby producing an amplified and enriched disc stem cell population.

In one embodiment, cells are grown in suspension in the second medium until they reach maturity, which in one embodiment, comprises the formation of spheres comprised of individual cells that expanded in a clonal manner. In another embodiment, cells are grown in suspension in the second medium until they reach a pre-determined size, or, in another embodiment, an appropriate size. In one embodiment, the pre-determined size is roughly 100 microns to 400 microns in diameter.

In another embodiment, cells are grown in suspension in the third medium until they reach maturity, which in one embodiment, comprises the formation of cell aggregates, cell clusters, or aggregate cell clusters. In one embodiment, said aggregates, clusters, or aggregate clusters are not geometric in shape but are still roughly spherical. In another embodiment, cells are grown in suspension in the third medium until they reach a pre-determined size, or, in another embodiment, an appropriate size. In one embodiment, the pre-determined size is roughly 150 microns to 600 microns in diameter.

In one embodiment, said first medium is attachment culture medium, which, in another embodiment, is called Discotek medium. In one embodiment, said second medium is discosphere or sphere culture medium, which, in another embodiment, is called N5. In one embodiment, said third medium is cluster culture medium, which, in another embodiment, is called N10.

In another embodiment, the present invention provides a method of producing an amplified and enriched disc stem cell population comprising the steps of: (a) suspending isolated nucleus pulposus cells in a medium comprising approximately 15% serum, basic fibroblast growth factor (bFGF), epidermal growth factor (EGF), and human neonatal foreskin fibroblast (NFF) cell supernatant; (b) plating the suspension onto gelatin-coated tissue culture plates wherein said cells grow as an attachment culture as a monolayer; thereby producing an amplified nucleus pulposus cell population, (c) suspending said enriched disc stem cell population in a medium comprising 50% methylcellulose, fetal calf serum (FCS), basic fibroblast growth factor (bFGF), and epidermal growth factor (EGF); (d) distributing the suspension onto ultra-low binding culture plates; wherein an individual disc stem cell grows into a sphere-like cell cluster in a clonal manner, thereby producing an amplified and enriched disc stem cell population, (e) suspending said amplified and enriched disc stem cell population in a medium comprising fetal calf serum (FCS), basic fibroblast growth factor (bFGF), and epidermal growth factor (EGF) and lacking methylcellulose; and (f) distributing the suspension onto ultra-low binding culture plates, wherein said amplified disc stem cell population grows into a large cluster of heterogeneous morphology, thereby producing a further amplified and enriched disc stem cell population.

In another embodiment, the present invention provides a method of producing an amplified and enriched disc stem cell population comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a population of nucleus pulposus cells from said first medium; (c) growing said nucleus pulposus cells in a second medium comprising methylcellulose, serum, basic fibroblast growth factor (bFGF), and epidermal growth factor (FOE) on ultra-low binding culture plates to confluency; (d) isolating a population of disc stem cells from said second medium, thereby producing an amplified disc stem cell population.

In another embodiment, the present invention provides a method of producing an amplified and enriched disc stem cell population comprising the steps of: (a) suspending isolated nucleus pulposus cells in a medium comprising approximately 15% serum, basic fibroblast growth factor (bFGF), epidermal growth factor (EGF), and human neonatal foreskin fibroblast (NFF) cell supernatant; (b) plating the suspension onto gelatin-coated tissue culture plates; thereby producing an amplified nucleus pulposus cell population, (c) suspending said enriched disc stem cell population in a medium comprising >10% methylcellulose, fetal calf serum (FCS), basic fibroblast growth factor (bFGF), and epidermal growth factor (EGF); and (d) distributing the suspension onto ultra-low binding culture plates; wherein an individual disc stem cell grows into a sphere-like cell cluster in a clonal manner, thereby producing an amplified disc stem cell population.

In another embodiment, the present invention provides a method of producing an amplified and enriched disc stem cell population comprising the steps of: (a) growing nucleus pulposus cells as an attached monolayer in a first medium comprising serum, basic fibroblast growth factor (Win, epidermal growth factor (EGF), and human neonatal foreskin fibroblast (NFF) cell supernatant on gelatin-coated tissue culture plates to confluency; (b) isolating a population of nucleus pulposus cells from said first medium; (c) growing said disc stem cells in suspension in a second medium comprising serum, basic fibroblast growth factor (bFGF), and epidermal growth factor (EGF) and lacking methylcellulose on ultra-low binding culture plates to confluency; and (d) isolating a population of disc stem cells from said second medium, thereby producing an amplified disc stem cell population.

In another embodiment, the present-invention provides a method of producing an amplified and enriched disc stem cell population comprising the steps of: (a) suspending isolated nucleus pulposus cells in a medium comprising approximately 15% serum, basic fibroblast growth factor (bFGF), epidermal growth factor (EGF), and human neonatal foreskin fibroblast (NFF) cell supernatant; (b) plating the suspension onto gelatin-coated tissue culture plates; thereby producing an amplified nucleus pulposus cell population, (c) suspending said enriched disc stem cell population in a medium comprising fetal calf serum (FCS), basic fibroblast growth factor (bFGF), and epidermal growth factor (EGF) and lacking methylcellulose; and (d) distributing the suspension onto ultra-low binding culture plates, wherein individual disc stem cells form aggregate clusters, thereby producing an amplified disc stem cell population.

In one embodiment, the methods of the present invention may be used to produce a population of disc stem cells. In another embodiment, the methods of the present in invention may be used to produce a population of non-disc stem cells, which in one embodiment, are adult or somatic stem cells, which in one embodiment, are tissue-specific stem cells. In one embodiment, a tissue-specific stem cell is a stem cell from skin, muscle, intestine, or bone marrow. In another embodiment, a tissue-specific stem cell is a neural stem cell, which in one embodiment is from the subventricular zone, the hippocampus, the cerebral cortex, or spinal cord. In another embodiment, a tissue-specific stem cell is a stem cell from liver, heart, lung, pancreas, articular cartilage, bone, thymus, thyroid, or lymph node.

In one embodiment, an adult stem cell has the ability to self renew in a clonal manner; to divide asymmetrically to give rise to the different cell lineages that are a part of the tissue from which the stem cell was derived; to divide through multiple serial cell passages in vitro and in vivo, or a combination thereof.

In another embodiment, the methods of the present in invention may be used to produce a population of endothelial stem cells, or dental pulp stem cells. In another embodiment, the methods of the present in invention may be used to produce a population of fetal stem cells, embryonic stem cells, or cord blood stem cells. In such a case, a medium for nurturing the particular type of stem cell would be used, as is known in the art together with the methods of the present invention. In another embodiment, the methods of the present in invention may be used to produce a population of lung stem cells, heart stem cells, muscle stem cells, brain stem cells, kidney stem cells, liver stem cells, derma stem cells, fat stem cells, or a combination thereof. In another embodiment, the methods of the present in invention may be used to produce a population of Hematopoietic stem cells, mammary stem cells, mesenchymal stem cells, endothelial stem cells, neural stem cells, olfactory adult stem cells, neural crest stem cells, testicular cells, or a combination thereof.

In another embodiment, the invention provides a disc tissue derived clonal disc stem cell population, and wherein said disc stem cells are mixture of functional disc stem cells and progenitors from two separate germ layers. In one embodiment, the present invention provides intervertebral disc tissue-derived mesodermal nucleus pulposus stem cells and progenitors that can be expanded for additional research, cryopreserved, and/or used directly for therapeutic applications: In another embodiment, the present invention provides intervertebral disc tissue-derived neuroectodermal notochord stem cells and precursors, that can be expanded for additional research, cryopreserved, and used directly for therapeutic applications.

In one embodiment, the stem cell population may be exponentially expanded by cycling through the Discosphere, Cluster Method stages, or both the Discosphere and Cluster Method stages.

In one embodiment, the methods of the present invention amplify and enrich disc stem cells, while in another embodiment, they amplify and enrich disc progenitor cells.

In another embodiment, the present invention provides that plating a heterogeneous population of nucleus pulposus cells in a series of media as described herein comprising serum at low cell density results in isolation of nucleus pulposus stem cells. In another embodiment, the present invention provides that plating a heterogeneous population of nucleus pulposus cells in a series of media as described herein comprising serum at low cell density results in enriching a nucleus pulposus cell population for disc stem cells. In another embodiment, the present invention provides that plating a heterogeneous population of nucleus pulposus cells at low cell density in a series of media as described herein comprising serum, comprising a substance the interferes with cell attachment results in the survival of nucleus pulposus stem cells. In another embodiment, the present invention provides that plating a heterogeneous population of nucleus pulposus cells in a series of media as described herein, wherein one of the media comprises NIT and plating cells on gelatin coated plates at a high cell surface plating density, one comprises methylcellulose and plating at a low cell density on ultra low binding tissue culture plates which interferes with cell attachment and N5 media, one comprises N10 media and plating on ultra low binding tissue culture plates, results in the survival of nucleus pulposus stem cells.

In another embodiment, the supplemented media of the present invention enables only nucleus pulposus stem cells to grow. In another embodiment, the supplemented media of the present invention enable mostly nucleus pulposus stem cells to grow. In another embodiment, the supplemented media of the present invention preferentially encourages the growth of nucleus pulposus stem cells.

In another embodiment, a medium for use in the present invention comprises an antibiotic supplemented to the media. In another embodiment, the antibiotic supplemented to the media is penicillin-streptomycin. In another embodiment, a medium for use in the present invention comprises 1000-10000 U/ml penicillin-streptomycin supplemented to the media. In another embodiment, a medium for use in the present invention comprises 1000-3000 U/ml penicillin-streptomycin supplemented to the media. In another embodiment, a medium for use in the present invention comprises 3000-6000 U/ml penicillin-streptomycin supplemented to the media. In another embodiment, a medium for use in the present invention comprises 6000-10000 U/ml penicillin-streptomycin supplemented to the media. In another embodiment, a medium for use in the present invention comprises 3000-8000 U/ml penicillin-streptomycin supplemented to the media. In another embodiment, a medium for use in the present invention comprises 4000-6000 U/ml penicillin-streptomycin supplemented to the media. In another embodiment, a medium for use in the present invention comprises 5000 U/ml penicillin-streptomycin supplemented to the media.

In another embodiment, the medium for growing disc stem cells, disc progenitor cells, or a combination thereof comprises a serum replacer, which in one embodiment is Invitrogen Knock-Out Serum Replacement, TM-235, CDM-HD, Omni Serum, or other serum replacers known in the art. In another embodiment, the methods of the present invention provide that the medium is free of FBS when growing disc stem cells, nucleus pulposus stem cells, progenitor cells, nucleus pulposus progenitor cells, or a combination thereof.

In another embodiment, a medium for use in the present invention comprises KO serum replacer supplemented to the media. In another embodiment, a medium for use in the present invention comprises 0.5-30% KO serum replacer supplemented to the media. In another embodiment, a medium for use in the present invention comprises 5-30% knockout (KO) serum replacer supplemented to the media. In another embodiment, a medium for use in the present invention comprises 3-5% KO serum replacer supplemented to the media. In another embodiment, a medium for use in the present invention comprises 5-15% KO serum replacer supplemented to the media. In another embodiment, a medium for use in the present invention comprises 15-30% KO serum replacer supplemented to the media. In another embodiment, a medium for use in the present invention comprises 10-20% KO serum replacer supplemented to the media. In another embodiment, a medium for use in the present invention comprises 15-25% KO serum replacer supplemented to the media. In another embodiment, a medium for use in the present invention comprises 20% KO serum replacer supplemented to the media.

In another embodiment, a medium for use in the present invention comprises non-essential amino acids supplemented to the media. In another embodiment, a medium for use in the present invention comprises 0.1-10% non-essential amino acids supplemented to the media. In another embodiment, a medium for use in the present invention comprises 0.1-1% non-essential amino acids supplemented to the media. In another embodiment, a medium for use in the present invention comprises 1-5% non-essential amino acids supplemented to the media. In another embodiment, a medium for use in the present invention comprises 5-10% non-essential amino acids supplemented to the media. In another embodiment, a medium for use in the present invention comprises 15-30% non-essential amino acids supplemented to the media. In another embodiment, a medium for use in the present invention comprises 0.5-1% non-essential amino acids supplemented to the media. In another embodiment, a medium for use in the present invention comprises 0.8-1.2% non-essential amino acids supplemented to the media. In another embodiment, a medium for use in the present invention comprises 1% non-essential amino acids supplemented to the media.

In another embodiment, a medium for use in the present invention comprises L-glutamine supplemented to the media. In another embodiment, a medium for use in the present invention comprises 0.1-10 mM L-glutamine supplemented to the media. In another embodiment, a medium for use in the present invention comprises 0.1-5 mM L-glutamine supplemented to the media. In another embodiment, a medium for use in the present invention comprises 5-10 mM L-glutamine supplemented to the media. In another embodiment, a medium for use in the present invention comprises 5-8 mM L-glutamine supplemented to the media. In another embodiment, a medium for use in the present invention comprises 0.5-2.5 mM L-glutamine supplemented to the media. In another embodiment, a medium for use in the present invention comprises 1.5-3 mM L-glutamine supplemented to the media. In another embodiment, a medium for use in the present invention comprises 0.5-1.5 mM L-glutamine supplemented to the media. In another embodiment, a medium for use in the present invention comprises 0.8-1.2 mM L-glutamine supplemented to the media.

In another embodiment, a medium for use in the present invention comprises beta-mercaptoethanol supplemented to the media. In another embodiment, a medium for use in the present invention comprises 0.01-1 mM beta-mercaptoethanol supplemented to the media. In another embodiment, a medium for use in the present invention comprises 0.01-0.5 mM beta-mercaptoethanol supplemented to the media. In another embodiment, a medium for use in the present invention comprises 0.5-1 mM beta-mercaptoethanol supplemented to the media. In another embodiment, a medium for use in the present invention comprises 0.5-0.8 mM beta-mercaptoethanol supplemented to the media. In another embodiment, a medium for use in the present invention comprises 00.5-0.25 mM beta-mercaptoethanol supplemented to the media. In another embodiment, a medium for use in the present invention comprises 0.15-0.3 mM beta-mercaptoethanol supplemented to the media. In another embodiment, a medium for use in the present invention comprises 0.05-0.15 mM beta-mercaptoethanol supplemented to the media. In another embodiment, a medium for use in the present invention comprises 0.08-0.12 mM beta-mercaptoethanol supplemented to the media.

In another embodiment, the methods of the present invention provide that an enriched nucleus pulposus stem cell population of the present invention comprises at least 60% nucleus pulposus stem cells. In another embodiment, the methods of the present invention provide that an enriched nucleus pulposus stem cell population of the present invention comprises at least 70% nucleus pulposus stem cells. In another embodiment, the methods of the present invention provide that an enriched nucleus pulposus stem cell population of the present invention comprises at least 80% nucleus pulposus stem cells. In another embodiment, the methods of the present invention provide that an enriched nucleus pulposus stem cell population of the present invention comprises at least 85% nucleus pulposus stem cells. In another embodiment, the methods of the present invention provide that an enriched nucleus pulposus stem cell population of the present invention comprises at least 90% nucleus pulposus stem cells. In another embodiment, the methods of the present invention provide that an enriched nucleus pulposus stem cell population of the present invention comprises at least 95% nucleus pulposus stem cells.

In one embodiment, nucleus pulposus cells express genes that help them survive the hostile environment of the disc space, which in one embodiment comprises high pressure, hypoglycemia, catabolic metabolism, acidic pH, low oxygen tension, and dynamic tissue biomechanics including continuous compressive, sheer forces, or a combination thereof. In one embodiment, nucleus pulposus cells express hypoxia induced Factor gene (HIF1a), glucose transporter 1 (GLUM, or a combination thereof. In one embodiment, cells expressing these proteins and other proteins of a similar nature can survive and, in another embodiment, thrive in the disc space. In another embodiment, nucleus pulposus cells express proteoglycan products and intracellular biomechanical cytoskeleton and protein machinery to withstand the constant and significant compressive forces.

In one embodiment, the methods of the present invention provide purified disc stem cells. In one embodiment, "purified" refers to cells that are substantially free from other types of cells. In one embodiment, "substantially free from other types of cells" refers to cells that are at least 80% free from other types of cells, preferably at least 90% free from other types of cells, more preferably at least 95% free from other types of cells, more preferably at least 98% free from other types of cells, more preferably at least 99% free from other types of cells, and most preferably free from other types of cells.

In one embodiment, nucleus pulposus cells comprise inter alia precursor cells. In another embodiment, discospheres and/or clusters of the present invention comprise, inter ilia, precursor cells. In one embodiment, "precursor cells" refers to cells that, when cultured under appropriate conditions, develop into cells that possess the structure of, and function as, nucleus pulposus cells. Precursor cells include, but are not limited to, cells of the inner annulus fibroses and nucleus pulposus.

In one embodiment, "nucleus pulposus cells" refers to cells that possess the structure of, and function as, nucleus pulposus cells. Nucleus pulposus cells occupy the intervertebral disc, are relatively few in number, and are surrounded by a hydrated (water containing) extracellular matrix that contains a high concentration of proteoglycan. The cells display prominent nuclei and secrete proteoglycans. Nucleus pulposus cells are present in the soft central portion of intervertebral discs and are mucoid in texture. Nucleus pulposus cells act as a cushion between the vertebrae by absorbing shock, and facilitate bending and rotation of the vertebral column.

In one embodiment, nucleus pulposus cells comprise DNA, RNA, or proteins that serve as phenotypic markers and that allow nucleus pulposus cells to be distinguished from other types of cells. Nucleus pulposus phenotypic markers include, but are not limited to, hypoxia inducing factor-1 alpha. (HIF-1.alpha.), hypoxia inducing factor-1.beta. (HIF-1.beta.), glucose transporter-1 (GLUT-I), matrix metalloprotease-2 (MMP-2), MMP-9, lactate dehydrogenase-A (LDH-A), thrombospondin-1 (TSP-1), or a combination thereof. In another embodiment, nucleus pulposus phenotypic markers comprise phosphofructokinase-2 (PFK-2), GLUT-3, aggrecan, collagen type II, collagen type XI, Sox-9, or a combination thereof. In another embodiment, nucleus pulposus phenotypic markers comprise CD44 hyaluronan, receptor, beta-1 integrin subunit, endoglin/CD105, phosphorylated ERK, p38, or a combination thereof.

In one embodiment, a marker of a mature disc cell comprises collagen-2 alpha, vimentin, aggrecan, or a combination thereof.

In another embodiment, nucleus pulposus cells may be identified by morphological characteristics of nucleus pulposus cells. In one embodiment, "morphological characteristics" is intended to refer to the form and structure of cells, and includes, but is not limited to, the shape and organization of cells, and the pattern formed by groups of cells.

Notochordal cells can be identified through the recognition of their distinct cellular morphology, the presence of specific biomarkers, and other phenotypic characteristics found in vitro and in vivo. Notochordal cells tend to form clumps or aggregates of cells in most settings in vitro or in vivo. In vivo the number of these clump are typically 5-10 cells scattered in islands throughout the nucleus pulposus tissue. In vitro in cell culture after thorough digestion of the tissue, notochordal cells may be found in isolation and recognized by their morphology as being large vacuolated cells. In established cell culture and stem cell culture, notochordal cells may be aggregates of 5-10 cells up to 150-400 cells. Notochordal cells found in aggregate clumps or clusters typically secrete significant extracellular matrix which is readily detected with light microscopy as a viscous rarefied gel-like coat that surrounds and intercalates these multicelluar structures. The gel like extracellular matrix is further detected in vivo and in vitro and characterized as such through histological stains that detect proteoglycans such as Toluidine and Alician Blue. Notochordal cells can be identified by the expression of specific biomarkers, for example the expression of CK8 and Vimentin, and their coexpression. Finally, especially in stem cell culture, notochordal clusters are atypically resistant to digestion with Trypsin, requiring prolonged incubation times for digestion, and the use of post-digestion techniques of mechanical disruption of intracellular connections or bonding such as trituration.

Nucleus pulposus cells can also be identified, prior to isolation, during culture, and in post-culture assays, through the recognition of phenotypic markers characteristic of nucleus pulposus cells. Phenotypic markers characteristic of nucleus pulposus cells have been ascertained by identifying gene products whose expression is upregulated in response to the biological program present in the nucleus pulposus. While nucleus pulposus cells share some of the characteristics of cartilage cells, they are embedded in a unique anatomical location that influences their biochemical and physiological characteristics. Nucleus pulposus tissue is avascular, and the absence of a vascular system imposes severe restrictions on the availability of oxygen, nutrients, and growth factors to the cells. In addition, the osmotic pressure of the extracellular matrix is high, while the pH is low. To survive these hostile conditions, nucleus pulposus cells have modified their biosynthetic pathways through the expression of a unique set of genes. The increased expression of certain proteins and genes in response to severe oxygen and nutrient restriction provides a molecular profile that can be used to distinguish nucleus pulposus cells from cells of the surrounding tissues.

Precursor cells can be identified using numerous methods familiar to one of ordinary skill in the art. Once identified, and then isolated, precursor cells can be cultured under conditions effective to cause the cells to differentiate into nucleus pulposus cells.

In some embodiments of the invention, precursor cells can be identified by localizing proliferative centers in the disc unit. Proliferative centers can be identified by various methods familiar to the art-skilled, including determination of the pattern of bromodeoxy-uridine (BrdU) incorporation over time into the DNA of cells of different regions of the disc, including the annulus fibrosus, vertebral end plates, and nucleus pulposus.

In one embodiment, a biomarker for a disc stem cell is OCT-4, nestin, CD133, CK8 or a combination thereof. In one embodiment, disc stem cells produced by a method of the present invention express CK8. In one embodiment, disc stem cells produced by a method of the present invention express CD133. In another embodiment, stem cells produced by a method of the present invention comprise activation of the OCT-4 promoter in cells stably transfected with a reporter transgene construct consisting of a full length human OCT-4 promoter with all four regulatory elements, upstream of and directly regulating a green fluorescent protein reporter gene. Activation of the OCT-4 promoter, as described, indicates the expression of OCT-4 and implicates its activity in these stem cells to regulate it target genes (i.e., NOS genes).

In one embodiment, a biomarker for a mature nucleus pulposus cell is Collagen 2, Vimentin, Aggrecan, or a combination thereof. In one embodiment, at least a portion of said stem cell population produced by a method of the present invention is capable of generating mature disc cells that express the appropriate biomarkers, including in one embodiment, Collagen II and Vimentin, after incubation with chondrogenic differentiating media. In another embodiment, at least a portion of said stem cell population produced by a method of the present invention generates mature disc cells that express the appropriate biomarkers, including Collagen II and Vimentin, after incubation with chondrogenic differentiating media. In one embodiment, chondrogenic differentiating media comprises TGF-β1 and TGF-β3 (transforming growth factor beta), IGF (insulin-like growth factor), BMP2, BMP4, and BMP7 (bone morphogenic protein), or a combination thereof. In one embodiment, chondrogenic differentiating media comprises dexamethasone, TGF-β1, TGF-β3, BMP2, BMP4, and BMP7, or a combination thereof.

In one embodiment, "about" is intended to refer to plus or minus 10%.

In one embodiment, the present invention uses a sample as starting material in the methods of the present invention. In one embodiment, the term "sample" refers to biological material. The sample assayed by the present invention is not limited to any particular type. Samples include, as non-limiting examples, single cells, multiple cells, tissues, biological fluids, biological molecules, or supernatants or extracts of any of the foregoing. Examples include tissue removed during resection, blood, urine, lymph tissue, lymph fluid, cerebrospinal fluid, mucous, and stool samples. The sample used will vary based on the assay format, the detection method and the nature of the tissues, cells or extracts to be assayed. Methods for preparing samples are well known in the art and can be readily adapted in order to obtain a sample that is compatible with the method utilized.

In one embodiment, the methods of the present invention further comprise detecting biomarkers of a cell type. In one embodiment, the term "detecting" means to establish, discover, or ascertain evidence of expression of phenotypic markers of nucleus pulposus cells. Methods of detecting gene expression are well known to those of skill in the art. For example, methods of detecting nucleus pulposus marker polynucleotides include, but are not limited of PCR, Northern blotting, Southern blotting, genomic approaches such as microarray, RNA protection, and DNA hybridization (including in situ hybridization). Methods of detecting nucleus pulposus marker polypeptides include, but are not limited to, Western blotting, ELISA, enzyme activity assays, slot blotting, peptide mass fingerprinting, electrophoresis, fluorescent activated cell sorting analysis (FACS), stable transfection of and assay of reporter transgenes, and immunohistochemistry. Other examples of detection methods include, but are not limited to, histologic tissue stains and analysis, radioimmunoassay (RIA), chemiluminescence immunoassay, fluoroimmunoassay, time-resolved fluoroimmunoassay (TR-FIA), or immunochromatographic assay (ICA), all well known by those of skill in the art.

In one embodiment, the term "presence" refers to establishing that the item in question is detected in levels greater than background.

In one embodiment, the phrase "evidence of expression of nucleus pulposus phenotypic markers" refers to any measurable indicia that a nucleus pulposus phenotypic marker is expressed in the sample. Evidence of nucleus pulposus phenotypic marker expression may be gained from methods including, but not limited to, PCR, FISH, ELISA, HIC, FACS, or Western blots.

In one embodiment, the amplified disc stem cells produced using the methods of the present invention are then exposed to differentiation medium in order to produce nucleus pulposus cells. In one embodiment, differentiation medium comprises a medium supplemented with transforming growth factor 133 and 131 (TGF-β1; R&D Systems, MN), dexamethasone, ascorbate 2-phosphate, sodium pyruvate, proline, ITS-plus (Collaborative Biomedical Products, Cambridge, MA), or a combination thereof. In one embodiment, differentiation medium comprises DMEM supplemented with 10 ng/mL TGFβ3 and 131, 100 nmol/L dexamethasone, 50 μg/mL ascorbate 2-phosphate, 100 μg/mL sodium pyruvate, 40 μg/mL proline, and ITS-plus (Collaborative Biomedical Products, Cambridge, MA). In one embodiment, controls for the experiment are disc stem cells maintained media without any differentiating media supplements, or stem cell promoting media.

In one embodiment, the methods of the present invention comprise the steps described herein, in which additional method steps may also be included in the method. In another embodiment, the methods of the present invention consist of the steps described herein, in which additional method steps are not included in the method. In another embodiment, the methods of the present invention consist essentially of the steps described herein, in which additional method steps may also be included in the method but only additional steps that are not essential to practicing the method.

In one embodiment, the present invention provides plating a suspension onto adhesive-coated tissue culture plates. In one embodiment, said adhesive is gelatin. In another embodiment, said adhesive is agar. In another embodiment, said adhesive is a mixture of agar and gelatin. In another embodiment, said adhesive is an extracellular matrix molecule or protein, which in one embodiment is collagen or fibronectin. In another embodiment, said adhesive is poly-D-lysine. In another embodiment, said adhesive is another adhesive known in the art.

In one embodiment, at least a portion of cells express a particular marker. In one embodiment, at least a portion refers to at least 10%. In another embodiment, at least a portion refers to at least 20%. In another embodiment, at least a portion refers to at least 25%. In another embodiment, at least a portion refers to at least 30%. In another embodiment, at least a portion refers to at least 40%. In another embodiment, at least a portion refers to at least 50%. In another embodiment, at least a portion refers to at least 60%. In another embodiment, at least a portion refers to at least 70%. In another embodiment, at least a portion refers to at least 75%. In another embodiment, at least a portion refers to at least 80%. In another embodiment, at least a portion refers to at least 90%. In another embodiment, at least a portion refers to at least 95%.

In another embodiment, the present invention provides an amplified disc stem cell population obtained using any of the methods described hereinabove.

In another embodiment, the present invention provides an amplified nucleus pulposus cell population produced using any of the methods described hereinabove. In another embodiment, the present invention provides an amplified nucleus pulposus cell population produced using a method of amplifying a population of nucleus pulposus cells comprising the steps. of: (a) suspending isolated nucleus pulposus cells in a medium comprising serum, basic fibroblast growth factor (bFGF), epidermal growth factor (EGF), and human neonatal foreskin fibroblast (NFF) cell supernatant; and (b) plating the suspension onto gelatin-coated tissue culture plates, thereby producing an amplified nucleus pulposus cell population. In one embodiment, these amplified nucleus pulposus cells can be used in research and development into the characteristics of mature vs. stem cells. In another embodiment, these amplified nucleus pulposus cells can be seeded with disc stem cells to improve their growth potential and, in one embodiment, the final tissue nature/structure/biology of the disc stem cells.

In another embodiment, the present invention provides an enriched disc stem cell population obtained using a method of producing an enriched disc stem cell population from nucleus pulposus cells comprising the steps of (a) suspending a disc tissue derived clonal stem cell population in a medium comprising >10% methylcellulose, serum, basic fibroblast growth factor (bFGF), and epidermal growth factor (EGF); and (b) distributing the suspension onto ultra-low binding culture plates, wherein an individual disc stem cell grows into a sphere-like cell cluster in a clonal manner, thereby producing an enriched disc stem cell population.

In one embodiment, the serum is fetal calf serum. In one embodiment, said serum is present in said media at 5%.

In another embodiment, the present invention provides a disc tissue derived clonal stem cell population obtained using a method of producing an enriched disc stem cell population from nucleus pulposus cells comprising the steps of (a) suspending a disc tissue derived cell population in a medium comprising >10% methylcellulose, serum, basic fibroblast growth factor (bFGF), and epidermal growth factor (EGF); and (b) distributing the suspension onto ultra-low binding culture plates, wherein individual disc stem cells grow in a clonal manner into multicellular clusters of spherical shapes, thereby producing a disc tissue derived clonal stem cell population.

In another embodiment, the present invention provides a disc tissue derived clonal stem cell population obtained using a method comprising the steps of: (a) suspending a nucleus pulposus cell population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) growing said single cell suspension for 10-20 days, wherein an individual disc stem cell grows into a sphere-like cell cluster in a clonal manner, thereby producing an enriched disc stem cell population.

In one embodiment, a sphere-like cell cluster arises from the discosphere or sphere culture conditions as described hereinabove. In one embodiment, conditions (low cell density, methylcellulose, low attachment plates) lead to conditions where cells are unable to attach to each other or to the plates. In one embodiment, these conditions lead to the survival of only stem cells, which grow in a multicellular structure originating from a single cell so that the progeny are clonally derived.

In one embodiment, the disc tissue derived clonal disc stem cell population may be cryopreserved; or used directly for research, experimental therapeutics, definitive therapeutics, or a combination thereof.

In another embodiment, the present invention provides a disc tissue derived heterogeneous stem cell population obtained using a method of amplifying a disc stem cell population comprising the steps of: (a) suspending a sphere-like cluster of disc stem cells or an isolated disc stem cell from said sphere-like cell cluster in a medium comprising serum, basic fibroblast growth factor (bFGF), and epidermal growth factor (EGF) and lacking methylcellulose; and (b) distributing the suspension onto ultra-low binding culture plates, wherein said cluster or cell grows into a large aggregate cluster of heterogeneous morphology, thereby producing a disc tissue derived heterogeneous stem cell population.

In another embodiment, the present invention provides an amplified disc stem cell population obtained using a method of amplifying a disc stem cell population comprising the steps of: (a) suspending a sphere-like cluster of disc stem cells or an isolated disc stem cell from said sphere-like cell cluster in a medium comprising serum, basic fibroblast growth factor (bFGF), and epidermal growth factor (EGF) and lacking methylcellulose; and (b) distributing the suspension onto ultra-low binding culture plates, wherein said cluster or cell grows into a large aggregate cluster of heterogeneous morphology, thereby producing an amplified disc stem cell population.

In another embodiment, the present invention provides a disc tissue derived heterogeneous stem cell population obtained using a method comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (EGF); (b) distributing the suspension onto ultra-low binding culture plates; (c) growing said suspension for 8-16 days, wherein said cluster or cell grows into a large aggregate cluster of heterogeneous morphology, thereby amplifying and further enriching an enriched disc stem cell population.

In one embodiment, a heterogeneous stem cell population arises from the culture conditions of the cluster culture described hereinabove. In one embodiment, a heterogeneous stem cell population comprises cells from a single cluster, single cells, intermediate aggregates, or a combination thereof. In one embodiment, disc stem cells cultured in suspension in low density in a medium lacking methylcellulose stick to each other and to large clusters, resulting in a heterogeneous population of cells. In one embodiment, the heterogeneous stem cell population comprises clusters comprising a single disc stem cell clonally reproduced in-contact with single stem cells or one or more additional clonally reproduced disc stem cells. In another embodiment, the cell-cell contact induces limited differentiation so that the heterogeneous stem cell population comprises disc stem cells, early progenitor cells, and a small percentage of more mature cells on the edges where most of the cell-cell contact occurs. In one embodiment, cultures of the present invention, and specifically cluster culture, are incubated with gentle agitation, as is known in the art.

In another embodiment, the present invention provides an amplified and enriched disc stem cell population obtained using any of the methods of producing an amplified and enriched disc stem cell population described herein. In one embodiment, the present invention provides an amplified and enriched disc stem cell population obtained using a method of producing an amplified and enriched disc stem cell comprising the steps of: (a) growing attached nucleus pulposus cells in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) growing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) growing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, thereby producing an amplified and enriched disc stem cell population.

In another embodiment, the present invention provides an amplified disc stem cell population obtained using a method of producing an amplified and enriched disc stem cell population comprising the steps of: (a) growing attached nucleus pulposus cells in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a population of nucleus pulposus cells from said first medium; (c) growing said nucleus pulposus cells in a second medium comprising methylcellulose, serum, basic fibroblast growth factor (bFGF), and epidermal growth factor (EGF) on ultra-low binding culture plates to confluency; (d) isolating a population of disc stem cells from said second medium, thereby producing an amplified disc stem cell population.

In another embodiment, the present invention provides an amplified and enriched disc stem cell population obtained using a method of producing an amplified and enriched disc stem cell population comprising the steps of: (a) suspending isolated nucleus pulposus cells in a medium comprising approximately 15% serum, basic fibroblast growth factor (bFGF), epidermal growth factor (EGF), and human neonatal foreskin fibroblast (NFF) cell supernatant; (b) plating the suspension onto gelatin-coated tissue culture plates wherein said cells grow as an attachment culture in a monolayer; thereby producing an amplified nucleus pulposus cell population, (c) suspending said amplified nucleus pulposus cell population in a medium comprising >10% methylcellulose, fetal calf serum (FCS), basic fibroblast growth factor (bFGF), and epidermal growth factor (EGF); and (d) distributing the suspension onto ultra-low binding culture plates; wherein individual disc stem cells form grow into spherical shapes in a clonal manner, thereby producing an amplified and enriched disc stem cell population.

In another embodiment, the present invention provides a method of treating a subject having a herniated disc, comprising the step of administering to said subject an amplified disc stem cell population obtained using any of the methods described hereinabove.

In one embodiment, the present invention provides a method of treating a subject having a herniated disc, comprising the step of administering to said subject an amplified and enriched disc stem cell population obtained using a method comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates wherein said cells grow as an attached monolayer to confluency; (b) isolating a single cell population of nucleus pulposus cells from said first medium; (c) growing said nucleus pulposus cells in suspension in a second medium comprising methylcellulose, serum, basic fibroblast growth factor (bFGF), and epidermal growth factor (EGF) on ultra-low binding culture plates until they grow into spherical shapes; (d) isolating a population of disc stem cells from said second medium; (e) growing said disc stem cells in suspension in a third medium comprising serum, basic fibroblast growth factor (bFGF), and epidermal growth factor (EGF) on ultra-low binding culture plates until at least some of said cells form an aggregate cluster; and (I) isolating a population of disc stem cells from said third medium, wherein said disc stem cells from said third medium are an amplified and enriched disc stem cell population, thereby producing an amplified and enriched disc stem cell population, thereby treating said subject having a herniated disc.

In one embodiment, the present invention provides a method of treating a subject having a herniated disc, comprising the step of administering to said subject an amplified and enriched disc stem cell population obtained using a method comprising the steps of: (a) suspending a nucleus pulposus cell population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) growing said single cell suspension for 10-20 days, wherein an individual disc stem cell grows into a sphere-like cell cluster in a clonal manner, thereby producing an enriched disc stem cell population, thereby treating said subject having a herniated disc.

In one embodiment, the present invention provides a method of treating a subject having a herniated disc, comprising the step of administering to said subject an amplified disc stem cell population obtained using a Method of producing an amplified and enriched disc stem cell population comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (EGF); (b) distributing the suspension onto ultra-low binding culture plates; (c) growing said suspension for 8-16 days, wherein said cluster or cell grows into a large aggregate cluster of heterogeneous morphology, thereby amplifying and further enriching an enriched disc stem cell population, thereby treating said subject having a herniated disc.

In one embodiment, the present invention provides a method of treating damage to or disease of the spinal joint of a subject, comprising the step of administering to said subject an amplified disc stem cell population obtained using a method comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) growing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) growing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, wherein said disc stem cells from said third medium are an amplified and enriched disc stem cell population, thereby producing an amplified and enriched disc stem cell population, thereby treating damage to or disease of the spinal joint of said subject.

In one embodiment, the present invention provides a method of treating damage to or disease of the spinal joint of a subject, comprising the step of administering to said subject an amplified disc stem cell population obtained using a method comprising the steps of: (a) suspending a nucleus pulposus cell. population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) growing said single cell suspension for 10-20 days, wherein an individual disc stem cell grows into a sphere-like cell cluster in a clonal manner, thereby producing an enriched disc stem cell population, thereby treating damage to or disease of the spinal joint of said subject.

In one embodiment, the present invention provides a method of treating damage to or disease of the spinal joint of a subject, comprising the step of administering to said subject an amplified disc stem cell population obtained using a method of producing an amplified and enriched disc stem cell population comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (EGF); (b) distributing the suspension onto ultra-low binding culture plates; (c) growing said suspension for 8-16 days, wherein said cluster or cell grows into a large aggregate cluster of heterogeneous morphology, thereby amplifying and further enriching an enriched disc stem cell population, thereby producing an amplified disc stem cell population, thereby treating damage to or disease of the spinal joint of said subject.

In one embodiment, the present invention provides a method of treating damage to or disease of a joint of a subject, comprising the step of administering to said subject an amplified disc stem cell population obtained using a method comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) growing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) growing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, wherein said disc stem cells from said third medium are an amplified and enriched disc stem cell population, thereby producing an amplified and enriched disc stem cell population, thereby treating damage to or disease of the joint of said subject.

In one embodiment, the present invention provides a method of treating damage to or disease of a joint of a subject, comprising the step of administering to said subject an amplified disc stem cell population obtained using a method comprising the steps of: (a) suspending a nucleus pulposus cell population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) growing said single cell suspension for 10-20 days, wherein an individual disc stem cell grows into a sphere-like cell cluster in a clonal manner, thereby producing an enriched disc stem cell population, thereby treating damage to or disease of the joint of said subject.

In one embodiment, the present invention provides a method of treating damage to or disease of a joint of a subject, comprising the step of administering to said subject an amplified disc stem cell population obtained using a method of producing an amplified and enriched disc stem cell population comprising the steps of: (a) suspending a sphere-like cluster of disc stem cells or an isolated disc stem cell from said sphere-like cell cluster in a medium—comprising 10% serum, basic fibroblast growth factor (bFGF), and epidermal growth factor (EGF); (b) distributing the suspension onto ultra-low binding culture plates; (c) growing said suspension for 8-16 days, wherein said cluster or cell grows into a large aggregate cluster of heterogeneous morphology, thereby amplifying and further enriching an enriched disc stem cell population, thereby treating damage to or disease of the joint of said subject.

In one embodiment, the present invention provides a method of repairing damaged or diseased disc tissue in a subject, comprising the step of administering to said subject an amplified disc stem cell population obtained using a method comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) growing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) growing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, wherein said disc stem cells from said third medium are an amplified and enriched disc stem cell population, thereby producing an amplified and enriched disc stem cell population, thereby repairing damaged or diseased disc tissue in said subject.

In one embodiment, the present invention provides a method of repairing damaged or diseased disc tissue in a subject, comprising the step of administering to said subject an amplified disc stem cell population obtained using a method comprising the steps of: (a) suspending a nucleus pulposus cell population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) growing said single cell suspension for 10-20 days, wherein an individual disc stem cell grows into a sphere-like cell cluster in a clonal manner, thereby producing an enriched disc stem cell population, thereby repairing damaged or diseased disc tissue in said subject.

In one embodiment, the present invention provides a method of repairing damaged or diseased disc tissue in a subject, comprising the step of administering to said subject an amplified disc stem cell population obtained using a method of producing an amplified and enriched disc stem cell population comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (EGF); (b) distributing the suspension onto ultra-low binding culture plates; (c) growing said suspension for 8-16 days, wherein said cluster or cell grows into a large aggregate cluster of heterogeneous morphology, thereby amplifying and further enriching an enriched disc stem cell population, thereby repairing damaged or diseased disc tissue in said subject.

In one embodiment, the present invention provides a method of treating damage to or disease of a joint of a subject, comprising the step of administering to said subject an amplified disc stem cell population obtained using a method comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) growing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) growing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, wherein said disc stem cells from said third medium are an amplified and enriched disc stem cell population, thereby producing an amplified and enriched disc stem cell population, thereby treating damage to or disease of a joint of said subject.

In one embodiment, the present invention provides a method of treating damage to or disease of a joint of a subject, comprising the step of administering to said subject an amplified disc stem cell population obtained using a method comprising the steps of: (a) suspending a nucleus pulposus cell population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) growing said single cell suspension for 10-20 days, wherein an individual disc stem cell grows into a sphere-like cell cluster in a clonal manner, thereby producing an enriched disc stem cell population, thereby treating damage to or disease of a joint of said subject.

In one embodiment, the present invention provides a method of treating damage to or disease of a joint of a subject, comprising the step of administering to said subject an amplified disc stem cell population obtained using a method of producing an amplified and enriched disc stem cell population comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (EGF); (b) distributing the suspension onto ultra-low binding culture plates; (c) growing said suspension for 8-16 days, wherein said cluster or cell grows into a large aggregate cluster of heterogeneous morphology, thereby amplifying and further enriching an enriched disc stem cell population, thereby treating damage to or disease of a joint of said subject.

In one embodiment, the present invention provides a method of preventing, inhibiting, or decreasing the likelihood of damage to or disease of a spinal joint of a subject, comprising the step of administering to said subject an amplified disc stem cell population obtained using a method comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a single cell population of nucleus pulposus cells from said first medium; (c) growing said nucleus pulposus cells in suspension in a second medium comprising methylcellulose, serum, basic fibroblast growth factor (bFGF), and epidermal growth factor (EGF) on ultra-low binding culture plates until at least one of said cells forms a sphere-like cluster; (d) isolating a population of disc stem cells from said second medium; (e) growing said disc stem cells in suspension in a third medium comprising serum, basic fibroblast growth factor (bFGF), and epidermal growth factor (EGF) on ultra-low binding culture plates until at least some of said cells form an aggregate cluster; and (f) isolating a population of disc stem cells from said third medium, wherein said disc stem cells from said third medium are an amplified and enriched disc stem cell population, thereby producing an amplified and enriched disc stem cell population, thereby preventing, inhibiting, or decreasing the likelihood of damage to or disease of the spinal joint of said subject.

In one embodiment, the present invention provides a method of preventing, inhibiting, or decreasing the likelihood of damage to or disease of the spinal joint of a subject, comprising the step of administering to said subject an amplified disc stem cell population obtained using a method comprising the steps of (a) suspending a nucleus pulposus cell population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) growing said single cell suspension for 10-20 days, wherein an individual disc stem cell grows into a sphere-like cell cluster in a clonal manner, thereby producing an enriched disc stem cell population, thereby preventing, inhibiting, or decreasing the likelihood of damage to or disease of the spinal joint of said subject.

In one embodiment, the present invention provides a method of preventing, inhibiting, or decreasing the likelihood of damage to or disease of the spinal joint of a subject, comprising the step of administering to said subject an amplified disc stem cell population obtained using a method of producing an amplified and enriched disc stem cell population comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (EGF); (b) distributing the suspension onto ultra-low binding culture plates; (c) growing said suspension for 8-16 days, wherein said cluster or cell grows into a large aggregate cluster of heterogeneous morphology, thereby amplifying and further enriching an enriched disc stem cell population, thereby preventing, inhibiting, or decreasing the likelihood of damage to or disease of the spinal joint of said subject.

In one embodiment, the present invention provides a method of preventing, inhibiting, or decreasing the likelihood of damage to or disease of a cartilage-containing joint of a subject, comprising the step of administering to said subject an amplified disc stem cell population obtained using a method comprising the steps of: (a) growing nucleus pulposus cells as an attached monolayer in a first medium comprising serum, basic fibroblast growth factor (bFGF), epidermal growth factor (EGF), and human neonatal foreskin fibroblast (NFF) cell supernatant on gelatin-coated tissue culture plates to confluency; (b) isolating a population of nucleus pulposus cells from said first medium; (c) growing said nucleus pulposus cells in a second medium comprising methylcellulose, serum, basic fibroblast growth factor (bFGF), and epidermal growth factor (EGO on ultra-low binding culture plates to confluency; (d) isolating a population of disc stem cells from said second medium; (e) growing said disc stem cells in suspension in a third medium comprising serum, basic fibroblast growth factor (bFGF), and epidermal growth factor (EGF) and lacking methylcellulose on ultra-low binding culture plates to confluency; and (f) isolating a population of disc stem cells from said third medium, wherein said disc stem cells from said third medium are an amplified disc stem cell population, thereby preventing, inhibiting, or decreasing the likelihood of damage to or disease of the cartilage-containing joint of said subject.

In one embodiment, the present invention provides a method of preventing, inhibiting, or decreasing the likelihood of damage to or disease of a cartilage-containing joint of a subject, comprising the step of administering to said subject an amplified disc stem cell population obtained using a method comprising the steps of: (a) suspending a nucleus pulposus cell population comprising disc stem cells as single cells at low density in a medium comprising 50% methylcellulose, 5% serum, basic fibroblast growth factor (bFGF), and epidermal growth factor (EGF); (b) distributing the suspension onto ultra-low binding culture plates; and (c) growing said single cell suspension for 10-20 days, wherein an individual disc stem cell grows into a sphere-like cell cluster in a clonal manner, thereby producing an enriched disc stem cell population, thereby preventing, inhibiting, or decreasing the likelihood of damage to or disease of the cartilage-containing joint of said subject.

In one embodiment, the present invention provides a method of preventing, inhibiting, or decreasing the likelihood of damage to or disease of a cartilage-containing joint of a subject, comprising the step of administering to said subject an amplified disc stem cell population obtained using a method of producing an amplified and enriched disc stem cell population comprising the steps of: (a) suspending a sphere-like cluster of disc stem cells or an isolated disc stem cell from said sphere-like cell cluster in a medium comprising 10% serum, basic fibroblast growth factor (bFGF), and epidermal growth factor (EGF); (b) distributing the suspension onto ultra-low biding culture plates; (c) growing said suspension for 8-16 days, wherein said cluster or cell grows into a large aggregate cluster of heterogeneous morphology, thereby amplifying and further enriching an enriched disc stem cell population, thereby preventing, inhibiting, or decreasing the likelihood of damage to or disease of the cartilage-containing joint of said subject.

In one embodiment, a joint or tissue is diseased, damaged or a combination thereof. Therefore, in one embodiment, a joint is structurally damaged but not diseased, diseased but not structurally damaged, or diseased and damaged, which in one embodiment is due to the destruction of the joint by the disease or because the disease weakens the joints such that typical forces cause structural damage.

In another embodiment, the present invention provides disc stem cells and methods of producing disc stem cells that may be used as part of a regenerative or reconstructive therapy for rebuilding the spinal joint after discectomy. Thus, in one embodiment, the present invention provides a method of rebuilding the spinal joint after discectomy comprising: administering to a subject an amplified disc stem cell population obtained using any of the methods described herein.

In another embodiment, the present invention provides a method of stem cell based therapeutics. In another embodiment, the present invention provides a method of treating degenerative disc disease.

In another embodiment, the present invention provides a method of treating a subject having a herniated disc. In another embodiment, the present invention provides a method of treating a subject having a degenerative disc disease (DDD). In another embodiment, the present invention provides a method of treating a subject having a DDD at one level in the lumbar spine (from L3-S1). In another embodiment, the present invention provides a method of treating a subject having no more than Grade 1 spondylolisthesis. In another embodiment, the present invention provides a method of treating a subject having more than Grade 1 spondylolisthesis. In another embodiment, the present invention provides a method of treating a subject having no more than Grade 1 spondylolisthesis that have had no relief from pain after at least six months of non-surgical treatment.

In another embodiment, the present invention provides disc cells for use as a therapy that when administered to a subject restores disc height. In another embodiment, the present invention provides disc cells for use as a therapy that when administered to a subject reduces pain. In another embodiment, the present invention provides disc cells for use as a therapy that when administered to a subject restores movement at the level where it is implanted.

In one embodiment, the present invention provides methods of treating IDD (intervertebral disc degeneration. In one embodiment, IDD is diagnosed using a combination of clinical criteria and imaging of the spine. In one embodiment, Mill is used to image the vertebrae and disc for evidence of disc bulging or herniation, endplate degradation (Schmorl's nodes), disc narrowing, tears in the annular disc capsule, osteophytes, compression of the neural elements, and changes in tissue signal characteristics.

In one embodiment, the present invention provides methods of treating, inhibiting, or suppressing lower back pain, which in one embodiment, is pain in the lumbar-sacral spine. In another embodiment, the present invention provides methods of treating, inhibiting, or suppressing neck pain. In another embodiment, the present invention provides methods of treating, inhibiting, or suppressing cervical spinal pain.

In one embodiment, the present invention provides methods of treating, inhibiting, or suppressing the degeneration of the lumbar-sacral spine. In another embodiment, the present invention provides methods of treating, inhibiting, or suppressing the degeneration of the cervical spine.

In one embodiment, cells produced using the methods of the present invention may be used along with other compositions to treat the diseases-described herein. Thus, in one embodiment, compositions that enhance the expression of pro-disc genes (or their protein products) such as SOX-9, TGFbeta1, TIMP1, and BMP2 through molecular and gene therapy approaches may be used in conjunction with the cells produced using the methods of the present invention.

In one embodiment, the present invention is directed to compositions and methods for the repair and/or replacement of degenerated or damaged or diseased intervertebral discs through reformation of intervertebral disc tissue. By implanting disc stem cells or differentiated nucleus pulposus cells with a carrier into the intervertebral space of a degenerated disc, the damaged or diseased tissue can effectively be repaired or replaced.

In one embodiment, "treating" refers to either therapeutic treatment or prophylactic or preventative measures, wherein the object is to prevent or lessen the targeted pathologic condition or disorder, as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

Some embodiments of the invention include methods of treating the initial stages of degenerative intervertebral disc disease in a subject, and involve minimally invasive surgical techniques, such as the implantation of a biomaterial scaffold and/or nucleus pulposus cells into the nucleus pulposus space of the subject. Biomaterial scaffolds are described in U.S. Pat. No. 5,964,807, incorporated herein by reference in its entirety.

In one embodiment, disc stem cells or nucleus pulposus cells derived from disc stem cells produced using the methods of the present invention can be used in open/ classical approaches or by closed/minimally invasive approaches to disc treatment. In one embodiment, percutaneous injection through a cannula is used to treat or prevent in situ degenerative disc disease without structural damage. In one embodiment, percutaneous injection is an outpatient treatment.

In one embodiment, disc stem cells are delivered to a subject in need. In another embodiment, disc stem cells and a cell carrier, such as, in one embodiment, Hystem-HP, from Glycosan, Inc., made of synthetic HA, is delivered to a subject in need. In another embodiment, aggrecan, amniotic matrix, etc is delivered with disc stem cells to a subject in need. In another embodiment, growth factors (in one embodiment, FGF-2, TGFB3) are delivered with disc stem cells to a subject in need. In another embodiment; additional supplements are delivered with disc stem cells to a subject in need.

Some embodiments of the invention involve implanting a biomaterial scaffold directly into the nucleus pulposus space with one or more percutaneous injections. In some embodiments of the invention, the biomaterial scaffold comprises biologically active glass, as previously described. In some embodiments of the invention, the scaffold further comprises biologically active molecules. In some embodiments of the invention, the scaffold is combined with one or more pharmaceutically acceptable excipients prior to implantation into the nucleus pulposus space. Pharmaceutically acceptable excipients are familiar to the skilled artisan and include, but are not limited to, buffers, physiological saline, and viscous fluids that harden into a gelatinous composite, such as, for example, self-setting hydrogel and alginate. Implantation of the biomaterial scaffold into the nucleus pulposus space leads to regeneration of nucleus pulposus cells with concomitant restoration of the function of the nucleus pulposus tissue.

In one embodiment of the invention, the methods of the present invention further comprise preparing cells, mixing cells with extracellular matrix, growth factors, or a combination thereof, loading or attaching cells to a cell carrier, injecting the cells and cell carrier into the disc, placing cells into a disc during surgery after the discectomy, or a combination thereof.

Some embodiments of the invention involve implanting nucleus pulposus cells into the nucleus pulposus space of a degenerated disc of a subject by making one or more injections with a needle, which in one embodiment, is a percutaneous injection. Ultrasound or other imaging techniques can be used to guide the needle to the nucleus pulposus space. In some embodiments of the invention, after implantation into the nucleus pulposus space, the nucleus pulposus cells continue to proliferate and expand, thereby regenerating nucleus pulposus tissue and reestablishing the natural function of the degenerated disc.

In another embodiment, administration of disc stem cells, with or without a carrier is via direct access to the, joint, which in one embodiment, is part of a surgical procedure. In one embodiment, the surgical procedure is a conventional open discectomy or microdiscectomy. In one embodiment, the surgical procedure is performed on a subject who had spinal joint disease, which in one embodiment, is structural with involvement of a nerve root and, in one embodiment involves severe pain in an extremity and, optionally back pain. In one embodiment, the surgical procedure would be performed after failure of conservative care. In one embodiment, the surgeon has to damage the joint to get access to the herniated disc (the structural defect). In one embodiment, a portion of the disc is removed leaving a defect in the disc and annulus (discectomy). In one embodiment, the surgeon applies the disc stem cell therapeutic product directly to the disc defect immediately after the discectomy, and then closes the wound.

In some embodiments of the invention, the nucleus pulposus cells are combined with one or more pharmaceutically acceptable excipients, as described above, prior to implantation into the nucleus pulposus space. In some embodiments of the invention, the nucleus pulposus cells are combined with biologically active molecules prior to implantation into the nucleus pulposus space.

In some embodiments of the invention, nucleus pulposus cells are generated by culturing nucleus pulposus cells and/or precursor cells, and the cells are then implanted into the nucleus pulposus space of a degenerated disc of a subject to be treated. In some embodiments of the invention, following cell culture, and prior to implantation into the nucleus pulposus space, contaminating non-nucleus pulposus cells are removed from the exogenously-cultured nucleus pulposus cells using methods familiar to one of ordinary skill in the art. In some embodiments of the invention, the exogenously cultured nucleus pulposus cells are removed from the carrier material upon which they were seeded during culture prior to implantation of the cells into the nucleus pulposus space.

Some embodiments of the invention involve methods of treating the advanced stages of intervertebral disc disease in a subject. Some embodiments of the invention involve implanting nucleus pulposus cells into the nucleus pulposus space as part of a larger substrate, which includes, in some embodiments of the invention, carrier material upon which the cells were seeded during culture.

In accordance with some embodiments of the present invention, the carrier is biodegradable, which means that, after implantation of nucleus pulposus cells into a degenerated disc, the carrier degrades into natural, biocompatible byproducts over time until the carrier is substantially eliminated from the implantation site and, ultimately, the body. In accordance with some embodiments of the present invention, the rate of biodegradation of the carrier is less than or equal to the rate of intervertebral disc tissue formation such that the rate of tissue formation is sufficient to replace the carrier that has biodegraded.

In some aspects of the present invention, the biodegradable carrier is bioactive, which means that the carrier enhances cell function. For instance, bioactive glass granules have been shown to enhance cell growth of typical bone cells. Schepers et al., U.S. Pat. No. 5,204,106. In addition, dense bioactive glass discs have been found to enhance osteoprogenitor cell differentiation beyond the levels of enhanced differentiation elicited by bone morphogenic protein. H. Baldick, et al., Transactions 5th World Biomaterials Conference, Toronto, II-114 (June, 1996).

In some embodiments of the invention, the biodegradable carrier has sufficient mechanical strength to act as a load bearing spacer until intervertebral disc tissue is reformed. In some embodiments, the biodegradable carrier is biocompatible such that it does not elicit an immune or inflammatory response that might result in rejection of the implanted material.

In some embodiments of the invention, the nucleus pulposus space of the degenerated disc to be treated by the methods of the invention is evacuated prior to implantation of the nucleus pulposus stem cells. Preferably, for treatment of advanced stages of intervertebral disc disease, the nucleus pulposus space of the degenerated disc is evacuated prior to implantation of the nucleus pulposus cells.

Evacuation of the degenerated intervertebral disc tissue, and primarily the nucleus pulposus tissue, is performed using known surgical tools with procedures adapted to meet the needs of the present invention. For example, an incision or bore may be made at the lateral edge in the annulus fibrosus and the intervertebral disc tissue is extracted from the nucleus pulposus via, for example, the guillotine cutting approach. The tissue can be extracted using a pituitary puller, a kerrison rongeur, scalpel, bore, or curette. Alternatively, the tissue may be aspirated. In some embodiments, the annulus fibrosus, or significant portions thereof, is left intact. It is preferred in some embodiments of the invention that at least 50% of the annulus fibrosus remains intact. It is more preferred in some embodiments that at least 85% of the annulus fibrosus remains intact.

Where delay occurs between evacuation of nucleus pulposus tissue and implantation of the exogenously cultured nucleus pulposus cells, the evacuated space may be temporarily filled with gel foam or other load bearing spacers known in the art.

In some embodiments of the invention, the previously described methods for treating intervertebral disc disease are used in conjunction with other known, conventional treatments.

The materials, methods and examples presented herein are intended to be illustrative, and are not intended to limit the scope of the invention. All publications, patent applications, patents, and other references mentioned herein are incorporated by reference in their entirety. Unless otherwise defined, all technical and scientific terms are intended to have their art-recognized meanings.

In another embodiment, the present invention provides a kit for amplifying a disc stem cell population comprising a container comprising a cluster medium comprising serum, basic fibroblast growth factor (bFGF), and epidermal growth factor (EGF) and lacking methylcellulose and instructions for the use thereof.

In another embodiment, the present invention provides a kit for producing an enriched disc stem cell population from nucleus pulposus cells comprising a container comprising a discosphere medium comprising methylcellulose, serum, basic fibroblast growth factor (bFGF), and epidermal growth factor (EGF) and instructions for the use thereof.

In another embodiment, the present invention provides a kit for amplifying a population of nucleus pulposus cells comprising a container comprising a Discotek medium comprising serum, basic fibroblast growth factor (bFGF), epidermal growth factor (EGF), and human neonatal foreskin fibroblast (NFF) cell supernatant and instructions for the use thereof.

In another embodiment, the present invention provides a kit for preparing disc tissue comprising a medium for disc preparation comprising PBS supplemented with antibiotics and/or antimycotics, DMEM/F12 medium comprising Collagenase H, Trypsin, and instructions for the use thereof.

It is to be understood that a kit of the present invention may comprise any one or more of the kits described hereinabove and is to be considered a part of the invention.

It is to be understood that a kit of the present invention may comprise a single medium or various combinations thereof. Therefore a kit of the present invention may comprise, for example, a first container comprising a cluster medium and, optionally, a second container comprising a discosphere medium, and, optionally, a third container comprising Discotek medium and, optionally, a fourth container comprising a disc preparation medium. It is to be further understood that each component of a described medium may be provided within a separate container to be mixed in the medium according to the instructions provided at a specified step in the protocol described in the instructions, in one embodiment. In one embodiment, the media is DMEM/F12 and, optionally N10 or N2 media.

In one embodiment, "instructional material," includes a publication, a recording, a diagram, or any other medium of expression which can be used to communicate the usefulness of the compositions of the invention in the kit.

In one embodiment, the instructional material of the kit may, for example, be affixed to a container that contains the composition (e.g., media, media components, and the like) of the invention or be shipped together with a container which contains the composition. Alternatively, the instructional material may be shipped separately from the container with the intention that the recipient uses the instructional material and the composition cooperatively.

In another embodiment, the kit further comprises wash solutions, reagents for marker detection, which in one embodiment, is markers of disc stem cells, which are known in the art.

Other kits, useful for practicing the invention as disclosed herein, are encompassed herein. The above discussed kits are exemplary and other kits as would be readily appreciated by the skilled artisan, based upon the disclosure provided herein, are included in the invention.

In another embodiment, the present invention provides a kit for cultivating disc stem cells, maintaining the pluripotency of disc stem cells; amplifying disc stem cells, or a combination thereof.

In one embodiment, the present invention provides a disc stem cell culture platform that enables isolation, culture, and expansion of disc stem cells from adult disc tissue, as described herein.

In another embodiment, the present invention provides a medium for cultivating and amplifying disc stem cells comprising: DMEM/F12, NFF, serum, FGF, and EGF. In another embodiment, the present invention provides a medium for cultivating and amplifying disc stem cells comprising: 66% DF10, 33% NFF, 14.5% serum, 10 ng/ml FGF, and 10 ng/ml EGF. In one embodiment, this media is referred to herein as Discotek media.

In another embodiment, the present invention provides a disc replacement device comprising nucleus pulposus cells. In another embodiment, the present invention provides an artificial disc comprising nucleus pulposus cells. In another embodiment, the disc replacement device is an intervertebral disc replacement device. Methods for making and using these compositions are known in the art and described in for e.g. ITS 2009/0074835, which is incorporated by reference herein in its entirety.

In another embodiment, an intervertebral disc is located between the concave articular surfaces of the adjacent vertebral body endplates. In another embodiment, the disc replacement device of the present invention permits movements such as flexion, extension, lateral flexion, and rotation. In another embodiment, the disc replacement device of the present invention is used to repair and/or replace injured or damaged or diseased intervertebral discs. In another embodiment, the disc replacement device of the present invention provides a prosthetic disc that combines both stability to support the high loads, of the patient's vertebrae and flexibility to provide the patient with sufficient mobility and proper spinal column load distribution.

In another embodiment, the present invention provides a method of producing an artificial disc, comprising the step of growing discospheres or clusters in a disc scaffold. In another embodiment, the present invention provides a method of producing an intervertebral disc replacement device, comprising the step of growing discospheres or clusters in a disc scaffold. In another embodiment, discospheres or clusters are administered onto a disc scaffold. In another embodiment, discospheres or clusters are administered into a layer comprising collagen in the disc scaffold. In another embodiment, discospheres or clusters are administered onto a layer comprising collagen in the disc scaffold. In another embodiment, discospheres or clusters are injected into a disc scaffold (Example 4). In another embodiment, discospheres or clusters are injected onto a disc scaffold. In another embodiment, discospheres or clusters are injected into a layer comprising collagen in the disc scaffold. In another embodiment, discospheres or clusters are injected onto a layer comprising collagen in the disc scaffold. In another embodiment, the discospheres or clusters of the present invention are applied or injected into or onto the disc scaffold together with a composition of the present invention. In another embodiment, the discospheres or clusters of the present invention are applied or injected into or onto the disc scaffold together with a DMEM/F12 medium supplemented with 10% FCS.

In another embodiment, the present invention provides a method of biologically repairing a disc, comprising the step of growing discospheres or clusters in culture, and resuspending them at the time of surgery in a cell carrier.

In another embodiment, a spinal disc tissue of the present invention comprises matured nucleus pulposus cells derived from disc stem cells of the present invention attached to a disc scaffold of the present invention: n another embodiment, a spinal disc tissue of the present invention comprises fibroblasts and matured nucleus pulposus cells derived from discospheres of the present invention attached to a disc scaffold of the present invention.

In another embodiment, the present invention provides a method of producing an intervertebral disc replacement device, comprising coating the disc scaffold of the present invention with nucleus pulposus cells growth factors. In another embodiment, the present invention provides a method of producing an intervertebral disc replacement device, comprising coating the disc scaffold of the present invention with nucleus pulposus cells adhesion factors. In another embodiment, the present invention provides a method of producing an intervertebral disc replacement device, comprising coating the disc scaffold of the present invention with nucleus pulposus cells differentiation factors.

In another embodiment, the present invention provides a method of producing an intervertebral disc replacement device, comprising placing the disc scaffold of the present invention in a medium comprising nucleus pulposus cells growth factors, adhesion factors, and differentiation factors.

In one embodiment, the nucleus pulposus cells provided by the present invention comprise autograft nucleus pulposus cells, allograft nucleus pulposus cells, or xenograft nucleus pulposus cells.

In another embodiment, the present invention provides that the recipient of the nucleus pulposus cells of the present invention is the donor. In another embodiment, the present invention provides that the recipient of the nucleus pulposus cells of the present invention may function at least in part as a donor. In another embodiment, the present invention provides that the donor of nucleus pulposus cells of the present invention is a single donor. In another embodiment, the present invention provides that multiple donors provide nucleus pulposus cells of the present invention to a single recipient. In another embodiment, the present invention provides that multiple donors provide nucleus pulposus cells of the present invention to multiple recipients. In another embodiment, the present invention provides that fetal sources are used. In another embodiment, the present invention provides that the donor or donors of the nucleus pulposus cells of the present invention is or are preferably having a familial relationship to the recipient in order to minimize or avoid immunosuppression. In another embodiment, the present invention provides that the donor or donors of the nucleus pulposus cells of the present invention is or are preferably having a familial relationship to the recipient in order to minimize or avoid the need for immunosuppressive substances. In another embodiment, the present invention provides guidelines for tissue procurement including surgical techniques of removal, number of hours between death of the donor and tissue procurement, and testing of the donor for infectious disease, are well known to one of skill in the art.

In one embodiment, two decades of direct and indirect evidence in animals and humans provide support that allograft tissue will not be immunorejected in recipients and immunotyping will not be required.

In one embodiment, cell culture behavior is relative to the tissue source, which in one embodiment, refers to the species of the tissue source, the age of the tissue source, the pathobiology of the tissue, or a combination thereof. In one embodiment, the time to confluency for disc tissue from healthy, young subjects and/or from tissue that is more cellular is 3-5 days. In one embodiment, the time to confluency for disc tissue from older animals, from certain species such as bovine, adult porcine, aged human or from degenerated tissue may be longer than 3-5 days.

In one embodiment, a robust culture in a T75 Flask yields around $10 \times 10^6$ cells.

In one embodiment, cells are not passaged back into Attachment culture, because, in one embodiment, each subsequent passage results in a decreased percentage of cells in the stem cell fraction due to differentiation of stem cells during the Attachment culture.

In one embodiment, the phrases fetal calf serum and fetal bovine serum may be used in the methods interchangeably.

In one embodiment, the methods of the present invention provide methods of procuring disc tissue, methods of processing disc tissue, methods of culturing disc cells, and methods of culturing disc stem cells, as were described herein. In another embodiment, the methods of the present invention provide methods of preparing disc stem cells for clinical use, which in one embodiment, comprise combining disc stem cells with growth factors and matrix molecules and re-suspending them in a cell carrier. In another embodiment, the methods of the present invention provide methods of treating, suppressing or inhibiting disc disease or symptoms thereof comprising administering disc stem cells or nucleus pulposus cells prepared using the methods described herein. In one embodiment, administering comprises injected a stem cell composition of the present invention percutaneously under CT or Fluoro guidance into the disc space in the context of nonstructural degenerative disc disease, whether one, two, or several levels. In another embodiment, in the context of structural disc disease requiring a surgery, the stem cell composition is injected through the annular defect into the disc defect left by the surgical discectomy.

Experimental Details Section

Materials and Methods

Preparation of Disc Tissues

A biopsy specimen of human nucleus pulposus was cut in pieces approximately 2-3 mm in size. The pieces were collected into a 50 ml falcon tube containing 30 ml of Phospbate buffered saline (PBS) supplemented with antibiotics/antimycotics. The tube was then centrifuged to pellet the tissue pieces, and PBS was aspirated. The tissue pellet was weighed per protocol. 15 ml of Dulbecco's Modified Eagle Media with F12 (DMEM/F12) medium containing 300 units/mL of Collagenase II solution was added to the tube. The contents of the tube were transferred to a T75 tissue culture flask, which was placed horizontally in a tissue culture incubator to incubate for 24 h. After 24 hours of enzymatic digestion, the contents of the T75 Flask were transferred to a 50 ml falcon tube. At that time, the tissue was completely digested, although floating cellular aggregates resistant to digestion were occasionally found.

The 50 ml falcon tube was centrifuged at 1200 rpm to pellet the cells, and the supernatant aspirated. The pellet was suspended in 2 ml of warm Trypsin. The suspension was incubated at 37° C. for two minutes. The suspension was triturated with a fire polished Pasteur pipette to ensure a true single cell suspension. 0.5 ml of Fetal Bovine Serum was added to stop the action of Trypsin.

A cell count was then performed. Next, the suspension was centrifuged at 1200 rpm to pellet the cells. The supernatant was aspirated and the cell pellet was resuspended in culture media to achieve the desired cell concentration.

Attachment Culture
Human Neonatal Foreskin Fibroblast Conditioned Media (Discotek Media)

Materials

Preparing Human Neonatal Foreskin Fibroblasts (NFF).

Foreskin specimens were cut into approximately 2-3 mm pieces, and the fragments were transferred to a 50 ml plastic tube in 30 ml of PBS supplemented with antibiotic-antimycotic. The tissue pieces were centrifuged at 1000 rpm for 5 min. PBS was aspirated, then 1-3 ml of Collagenase II solution (300 U/ml) in DMEM/F12 medium was added. Tubes were placed in a horizontal position into a shaker incubator (T=37° C.). Tubes were shaken at 100 rpm for 3-24 hours until fragments of tissue were visibly dissociated. Trypsin was added post-incubation, and the cells were incubated for 5 min with or without trituration as needed to completely dissociate the tissue. The resulting cell suspension was filtered through a 0.22 micron nylon mesh into a 50 ml tube, resulting in a single-cell suspension. The cell suspension was centrifuged for 4 min at 400 g at room temperature and the supernatant removed by aspiration. Cells were resuspended in DMEM/F12 medium with 10% fetal bovine serum (FBS).

NFF Supernatant

Human neonatal foreskin fibroblast (NFF) cells were expanded in DF10 media to fill one T150 culture flask to 90% confluency. Next, the supernatant was collected every two clays over 6 days, and filtered through a 0.22 um mesh filter. Supernatant was frozen at −20° C. in 50 ml aliquots. Media can be stored at −20° C. for up to 3 years.

Methods

Attachment Culture.

0.1% Gelatin coated tissue culture plates were prepared. The single cell suspension from the disc tissue preparation protocol was centrifuged at room temperature for 5 min at 1200 rpm. The supernatant was then removed by aspiration. The cells were resuspended in Discotek media (74 ml 1010 media; 6 ml FBS; 40 ml human neonatal foreskin fibroblast (NFF) supernatant (see materials hereinabove); 600 μl Penicillin/Streptomycin; 12 μl of 100 ng/μL epidermal growth factors (EGF), final [c]=10 ng/mL); 12 μl of 100 ng/μL fibroblast growth factor-2 (FGF-2), final [c]=10 ng/mL); total: 120.64 ml) at a volume of 10 ml, at a cell surface density of 50,000 cells/cm$^2$. The cell suspension was plated onto the Gelatin coated tissue culture plates. Media and growth factors were changed every second day.

The cells were passaged when they were 90% confluent by washing the attachment culture twice with PBS, and adding Trypsin. The culture with Trypsin was incubated for 5 minutes at 37° C. DMEM supplemented with serum was added to stop the Trypsin digestion. The contents of the plates were transferred to a 50 ml falcon tube. The contents were triturated to ensure a single cell suspension. A cell count was performed.

Cryopreservation

A portion of the cells were then cryopreserved in aliquots of 1 ml/tube in freezing media (90%, 10% DMSO), at 1-3×10$^6$ cells/ml.

Discosphere Stem Cell Culture Method-1 (Starting with Cryopreserved Attachment Cells)

20 ml of 2% methylcellulose (MC) and 2 mL of FBS were added to two 50 ml Falcon tubes. 10 ml of DF10 medium were added to a 15 ml Falcon tube. 3 M frozen cells/ml were thawed, placed in the tube with media, and mixed by inversion. The cell suspension was centrifuged at 1200 rpm for 5 minutes at 4° C. The supernatant was aspirated. The cell pellet was resuspended in 40 ml of 2×N5 medium, and mixed well. 20 mL of the suspension was added to each of the Falcon tubes. FGF2 and EGF were added to each to a final concentration 10 ng/ml each. Tubes were closed tightly, and the contents were carefully mixed by inversion. The mixture was distributed to 10 cm ultra-low binding culture dishes, 12 ml/dish, and at a concentration of 1×10$^5$/ml. Plates were incubated in the tissue culture incubator for continued culture. EGF/FGF was added at 10 ng/ml every second day. After 12-20 days, well developed discospheres were present, and the culture was ready for passage into suspension culture or for cycling. Cells can be passaged as single cell suspension, or as collected spheres and transferred to the cluster culture.

Discosphere Stem Cell Culture Method-2 (Starting with Attachment Culture)

Supernatant was removed and the plate washed with 2× with PBS. 1 ml Trypsin was added. The plate was placed in an incubator for 5 min at 37° C. Plates were removed and an equal amount of DF10 (to inactivate Trypsin) was added. All cell preparations were transferred to a 50 ml Falcon tube. A Pasteur pipette was used to triturate the cells and break up clusters. A cell count was done. Tubes were centrifuged for 5 min at 1200 rpm at room temperature. The supernatant was removed by aspiration. Cells were resuspended in methyl-cellulose (mix by vortexing) plus 12% fetal calf serum (FCS), diluted with 2×N2 medium to a final concentration of 6% serum—and a final density of $1×10^5$ cells/ml. EGF and FGF2 were added at 10 ng/ml each, and gently mixed. Solution was distributed into ultra-low binding 6-well plates (2 ml/well) covered with anti-adhesive coating, and incubated at 37° C. After two weeks, well developed disco-spheres were present, and the culture was ready for passage into suspension culture, or for cycling. Cells can be passaged as single cell suspension, or as collected spheres and transferred to the cluster culture.

Cluster Cell Culture Method

Contents were collected from 6 well plates and transferred to a 50 ml Falcon tube (1 tube/plate). 10 ml of DMEM media was added to the plate, which was washed carefully to remove remaining spheres. Washes were added to the falcon tubes. This step was repeated a second time. Tubes were centrifuged at 1200 rpm for 5 min at 4° C. to pellet the spheres. The supernatant was aspirated, resuspended in 1 ml of Trypsin, and incubated at 37° C. for 5 min. A Pasteur pipette was used to triturate and break up cell clusters. A cell count was performed. Samples were then centrifuged for 5 min at 1200 rpm at RT, and the supernatant was aspirated. The cells were resuspended in N10 media at a density of $1×10^4$ cells/ml. Disc tissue cell suspension was then plated on ultra low binding plates. EGF and FGF2 were added to a final concentration 10 ηg/ml each, and mixed gently. Media was changed every third day. Mature cluster cells were passaged when they were around 150-300 microns in diameter. Cycling back into this culture system was continued up to three times or until the desired cell number was achieved.

Example 1: Discotek Culture Platform

In one embodiment, the Discotek Culture Platform comprises the steps of (1) preparing a single cell suspension from a disc tissue specimen (FIG. 1, reference numerals 1-3), (2) the Attachment Culture Method (FIG. 1, reference numerals 4-7), (3) the Discosphere Culture Method (reference numerals 8-13), and (4) the Cluster Culture Method (FIG. 1, reference numerals 14-17).

Figure 2:
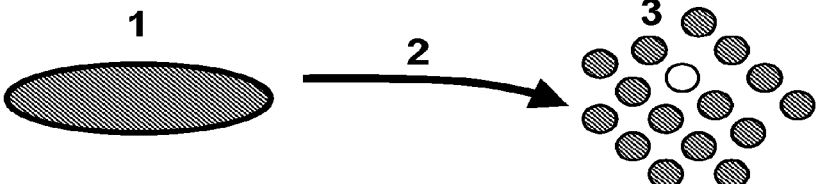
FIG. 2. Schematic of the preparation of a single cell suspension from a disc tissue specimen.

Disc tissue was procured from a human patient during surgery, or from an experimental animal model (FIGS. 1-2, reference number 1). The tissue was processed by dissection and then enzymatically digested overnight for 24 hours at 37° C. in Collagenase II (FIGS. 1-2, reference number 2). The result was a single cell suspension of all cells that comprise the disc tissue that can be plated into the subsequent culture steps (FIGS. 1-2, reference number 3).

The single cell suspension was plated into the attachment culture (reference number 4), in which the plates were coated with gelatin (reference number 5), causing the single cell suspension to attach (reference number 6) as it settles to the culture flask floor and contacts the surface (reference number 7). The cultures then grow efficiently as a monolayer, reaching confluency in 4-7 days when the starting disc tissue material was derived from young healthy disc tissue specimens. All species and even degenerated tissues grow well with this culture method, but the rate of growth varies and is delayed with tissues from older patients or animals, and degenerated tissues, and certain species (i.e., rat, rabbit, neonatal porcine, young healthy human tissue), as compared to specimens derived from humans that are older, degenerated tissues from any species, or certain other species that are more acellular generally speaking (i.e. adult porcine, cow, etc.)

When the cells were confluent, the attachment culture was passaged by preparing a single cell suspension—using enzymatic digestion, and plating the cells in the Discosphere Culture Method (reference numerals 8-11). This was also a step from which to cryopreserve cells for future research studies. The Discosphere culture method has methylcellulose as part of its media, and uses tissue culture plates that were coated so that the surfaces were ultra-low binding. Thus, this was a suspension culture. The cells were plated in low density and because they were in suspension and thus could not attach to each other to the culture vessel, each stem cell grows into a sphere-like cell cluster, in a clonal manner (reference numerals 12-13). Conversely, mature cells and late progenitors cannot grow without contact of other cells or a culture surface, and thus they die via apoptosis. The time it takes for the spheres to become mature in size (about 150-300 microns in diameter) was typically 10-20 days. Tissues that are degenerated, certain species that are accellular, and tissue from older patients or animal models took longer to reach maturity.

When the disc stem cell spheres (Discospheres) from the previously described culture method were mature, they were then passaged in one of two manners. First, to expand the cell population, they were passaged into the Cluster Culture Method by preparing a single cell suspension using enzymatic digestion, and plating the cells in the Cluster Culture Method at a predefined plating density of $1×10^4$. This was an appropriate time to cryopreserve stem cells in a single cell form. The cells were then grown in the Cluster Culture Method in cycles to expand them as needed. The time it typically takes for passaged cells from a single cell suspension to reach maturity as cluster-like cell aggregates, was around 8-16 days. The end product of cycling the Cluster cells was a stem cell product of the culture method, which can be cryopreserved for use at a future date as indicated. The second passaging approach was to transfer the Discospheres to the Cluster Culture directly. The spheres grow into large clusters of heterogeneous morphology. The time for the large clusters to reach maturity was 8-14 days. This was a stem cell product of the culture method, and the large cell clusters can be cryopreserved for future use. Tissues that are degenerated, certain species that are acellular, and tissue from older patients or animal models took longer to reach maturity.

Example 2: Preparation of Single Cell Suspensions

Figure 3:
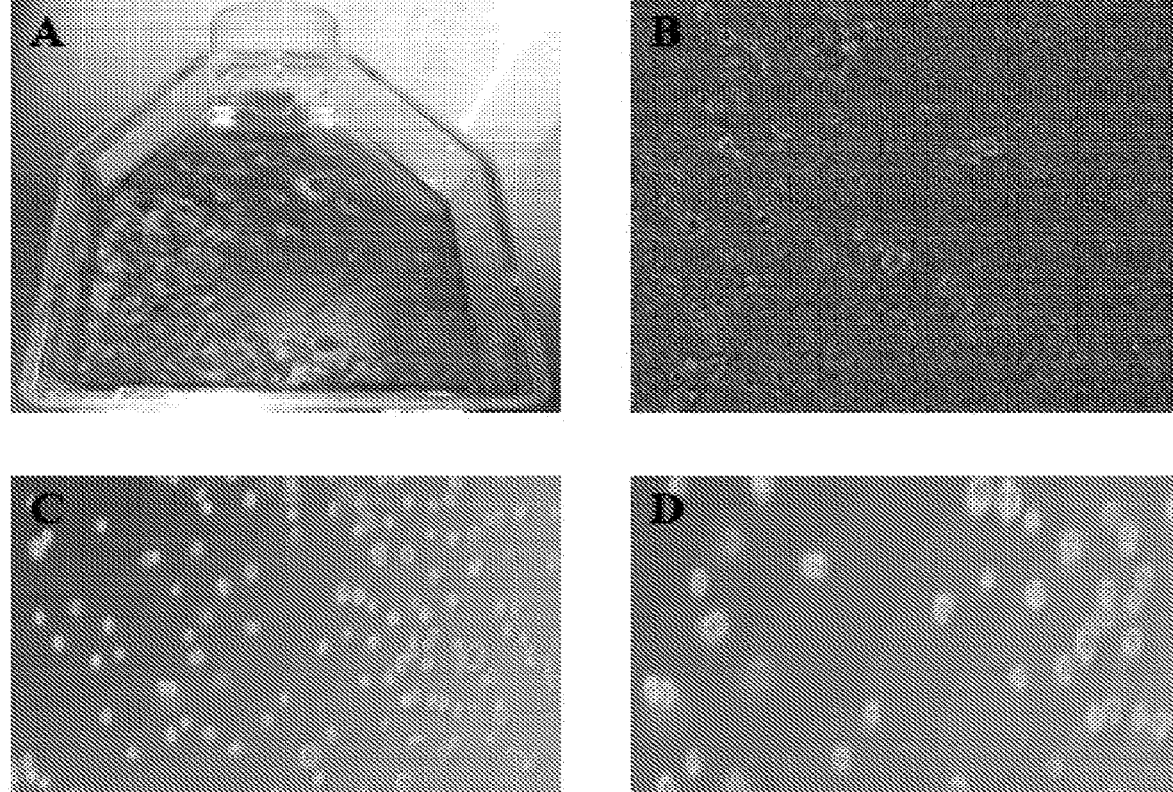
FIG. 3. Preparation of a single cell suspension of human disc tissues prior to plating cells in the culture method. A. Human disc tissues were dissected into smaller pieces, and washed thoroughly of blood and other tissue contaminants. The dissected fragments were placed in media with Collagenase II at 300 units/ml and incubated for 24 hours at 37° C. B. A large amount of debris was present post-digestion that made counting difficult was removed with the washing step. A single cell suspension free of debris was the product of this method shown here at 10× (C.) and 20× (D.) magnification.

Human disc tissues were dissected into smaller pieces, and washed thoroughly of blood and other tissue contaminants (FIG. 3A). The dissected fragments were placed in media with Collagenase II at 300 units/ml and incubated for 24 hours at 37° C. (FIG. 3B). A large amount of debris was present that made counting cells difficult and was removed with the washing step. A cell strainer was not used because of the routine presence of cellular clusters that are potentially notochordal clusters that do not break up without further trypsinization and trituration. It was thought that these cell clusters were a critical source of notochordal cells and that they resist digestion due to their extensive extracellular matrix. A single cell suspension was the product of this method (FIGS. 3C-D). This method does not use Trypsin for prolonged digestion, and does not use mechanical disassociation of tissues, to protect the fragile disc stem cell population. This increases the cellular health of individual stem cells, and results in overall higher yields of stem cells from the tissues. The disc tissue from adult humans and porcine species is very acellular, and the proportion of disc stem cells in a given unit of tissue was quite low. Further, the amount of cells and stem cells in degenerated tissues was even lower. Because a critical cell density (~1000-10,000 disc cells/ml) is required to provide enough stem cells to push a stem cell culture into active growth and expansion, every possible attempt to stabilize, protect, and enhance the stem cell population was taken. The fraction of cells that stem cells represent against the total cell population is not known, but indirect evidence for disc tissue stem cells, and previous adult tissue stem cell models collectively would suggest 0.1-0.001 or 1/1000 to 1/100,000.

Figure 4:
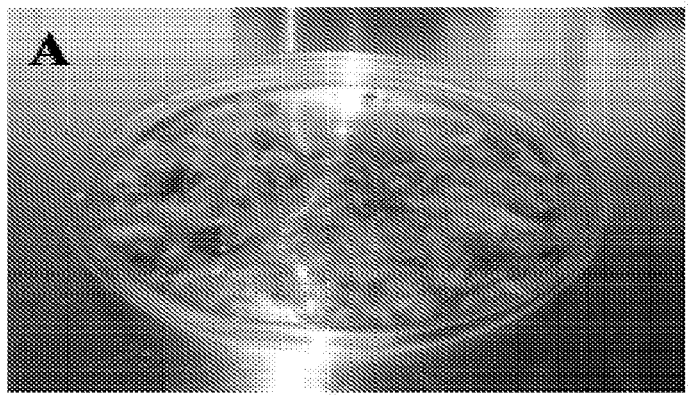
FIG. 4. Preparation of a single cell suspension of porcine disc tissues prior to plating cells in the culture method. A. Photograph of predissected and prewashed disc tissue fragments plated in a 10 cm dish. B. Photograph of predissected and postwashed disc tissue fragments plated in a T75 tissue culture flask for enzymatic digestion overnight for 24 hours at 37° C. C. 20× photomicrograph of post-digested and washed disc tissue cells in single cell suspension.
Figure 4:
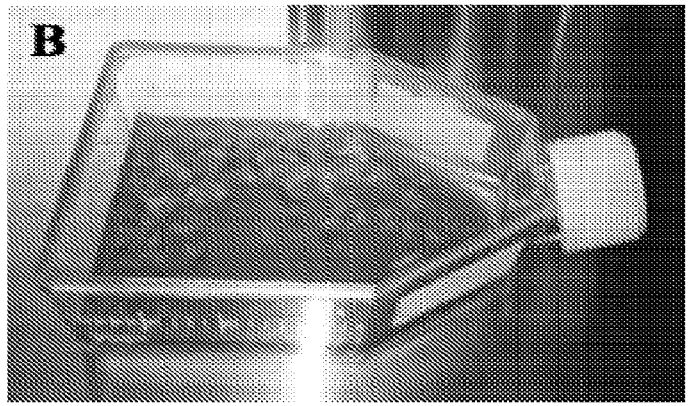
Figure 4:
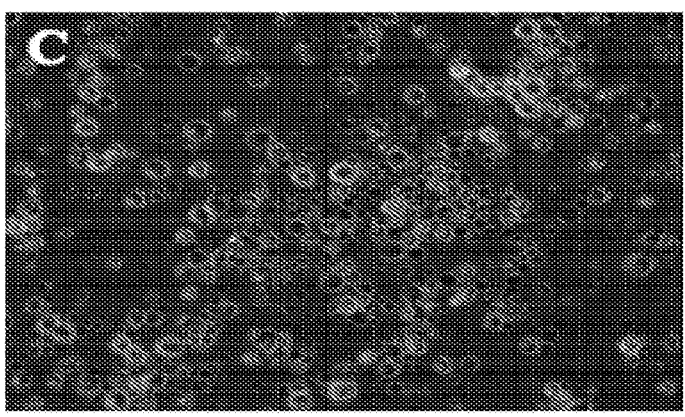

Porcine disc tissues (FIG. 4A) were dissected into smaller pieces, and washed thoroughly of blood and other tissue contaminants (FIG. 4B). The dissected fragments were placed in media with Collagenase at 300 units/ml and incubated for 24 hours at 37° C. A single cell suspension and was the product of this method (FIG. 4C). A cell strainer was not used because of the routine presence of cellular clusters that do not break up without brief trypsinization and trituration. It was thought that these cell clusters were a critical source of notochordal cells and they resist digestion due to their extensive extracellular matrix.

Example 3: Attachment Culture Method

Figure 5:
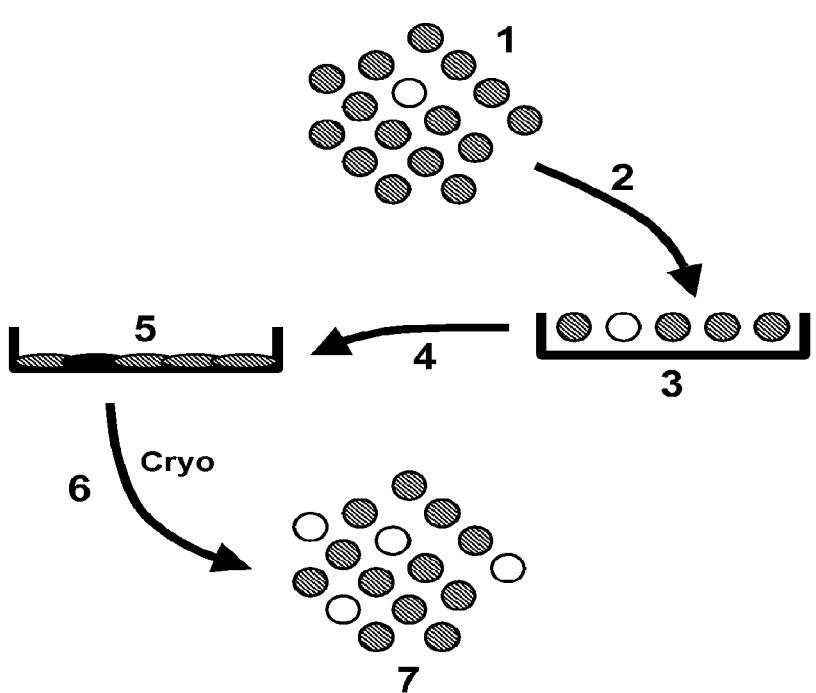
FIG. 5. Schematic of the Attachment Culture Method.

The single cell suspension was plated into the Attachment Culture Method (FIG. 5), in which the plates were coated with gelatin, causing the single cell suspension to attach as it settles to the culture flask floor and contacts the surface (FIGS. 1 and 5, reference numerals 4-5). The cultures then grew efficiently as a monolayer reaching confluency in 4-7 days when the starting disc tissue material was derived from young healthy disc tissue specimens. All species and even degenerated tissues grow well with this culture method, but the rate of growth varies and is delayed with tissues from older patients or animals, and degenerated tissues, and certain species (i.e., rat, rabbit, neonatal porcine, young healthy human tissue), as compared to specimens derived from humans that are older, degenerated tissues from any species, or certain other species that are more acellular generally speaking (i.e., adult porcine, cow, etc.) When the cells were confluent, the attachment culture was passaged by preparing a single cell suspension using enzymatic digestion, and plating the cells using the Discosphere Culture Method (FIGS. 1 and 5, reference numerals 6-7). This was also a step from which to cryopreserve cells for future research studies.

TABLE 1

Key Components of the Attachment Culture Method and Discotek Media.

| COMPONENT | AMOUNT/OTHER |
| --- | --- |
| MEDIA | DMEM/HAMSF12 |

TABLE 1-continued

Key Components of the Attachment Culture Method and Discotek Media.

| COMPONENT | AMOUNT/OTHER |
| --- | --- |
| NFF | 33% |
| SERUM | 14.5% |
| FGF | 10 ng/ml |
| EGF | 10 ng/ml |
| CELL SURFACE | GELATIN |

TABLE 2

Identification of important cell number and growth kinetic parameters from the tissue preparation method and the Attachment Culture Method.

| COMPONENT | Number/Other |
| --- | --- |
| Cell State | ATTACHED |
| Time to Confluency (Healthy Cellular Tissues) | 5-14 days |
| Time to Confluence (Degenerated Acellular Tissues) | 8-21 days |
| Plating Density | $50 \times 10^3/cm^2$ |

Figure 6:
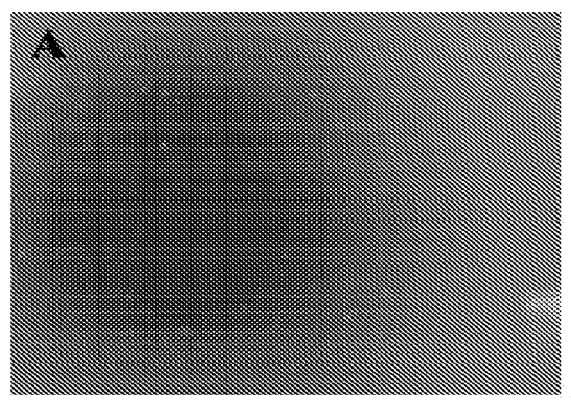
FIG. 6. The Attachment Culture Method at 24 hours postplating showing the initial attachment of porcine disc cells. A.-C. Photomicrographs of disc tissues cells plated from the single cell suspension product of the tissue preparation method. The cells are plated on gelatin-coated surfaces in Discotek media. Photomicrographs of disc cells growing attached and in a monolayer at 4× (A), 10× (B), and 20× (C) magnification are shown.
Figure 6:
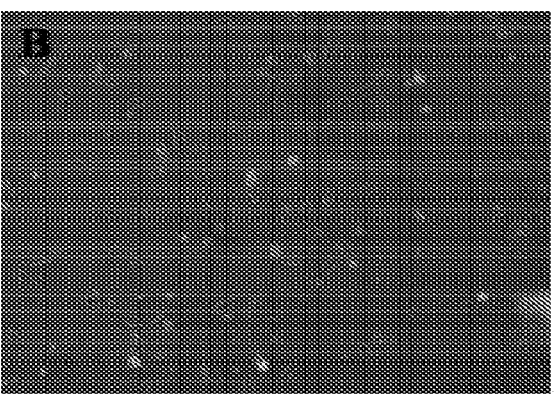
Figure 6:
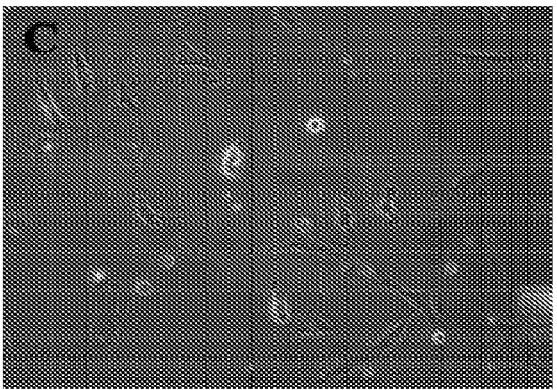
Figure 7:
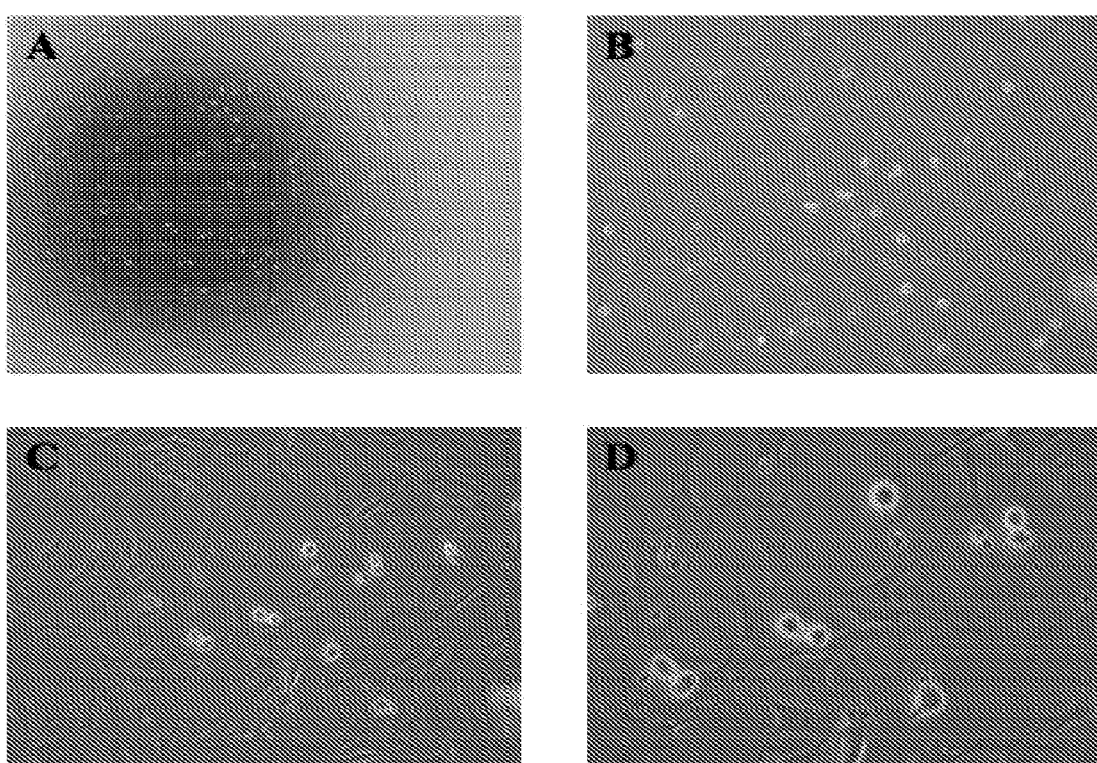
FIG. 7. The Attachment Culture Method at 70% confluency showing the growth and development of porcine disc cells in the culture method. Photomicrographs of disc tissues cells plated from the single cell suspension product of the tissue preparation method on gelatin coated surfaces in Discotek media and allowed to incubate for 3-5 days to reach 70% confluency. Photomicrographs of disc cells growing attached as a monolayer at 4× (A), 10× (B), 20× (C), and 40× (D) magnification are shown.
Figure 8:
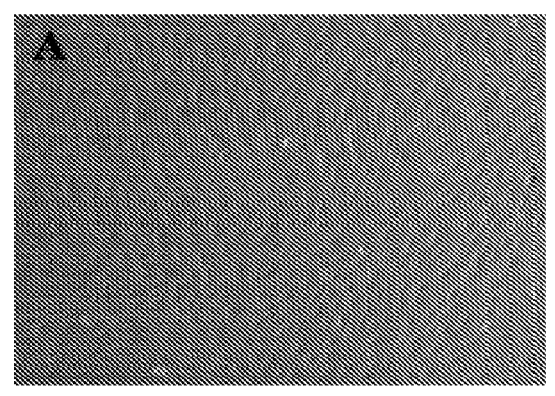
FIG. 8. The Attachment Culture Method at confluency showing the growth and development of porcine disc cells in the culture method. Photomicrographs of disc tissues cells plated from the single cell suspension product of the tissue preparation method on gelatin coated surfaces in Discotek media type 1 and allowed to incubate for 5-7 days to reach confluency. Photomicrographs of disc cells growing attached as a monolayer at 10× (A), 20× (B), and 40× (C) magnification are shown.
Figure 8:
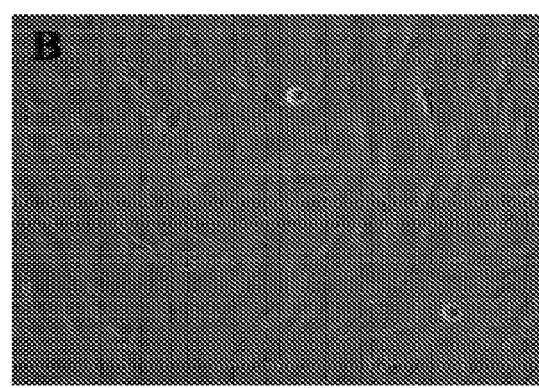
Figure 8:
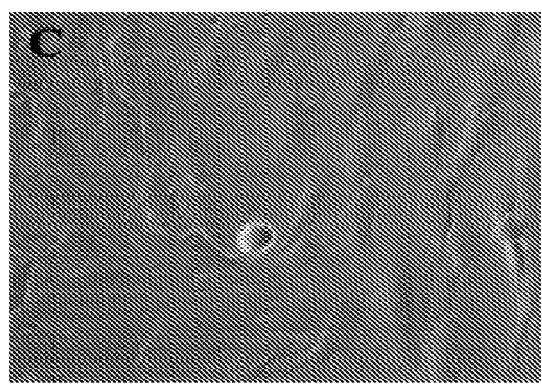
Figure 9:
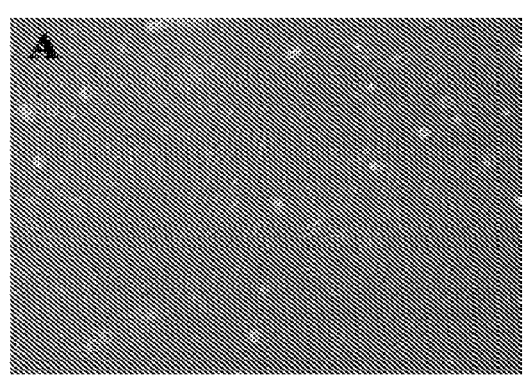
FIG. 9. The Attachment Culture Method at confluency showing the growth and development of human disc cells in the culture method. Photomicrographs of disc tissues cells plated from the single cell suspension product of the tissue preparation method on gelatin coated surfaces in Discotek media and allowed to incubate for 10-12 days to reach confluency. Photomicrographs of disc cells growing attached as a monolayer at 10× (A), 20× (B), and 40× (C) magnification are shown.
Figure 9:
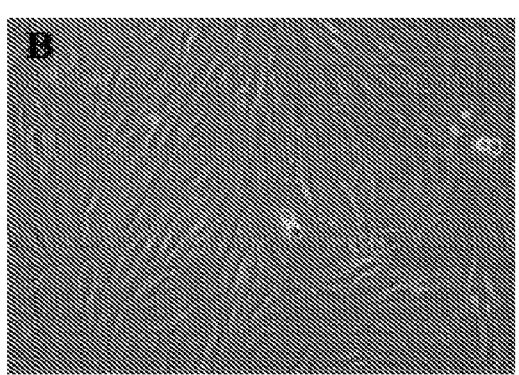
Figure 9:
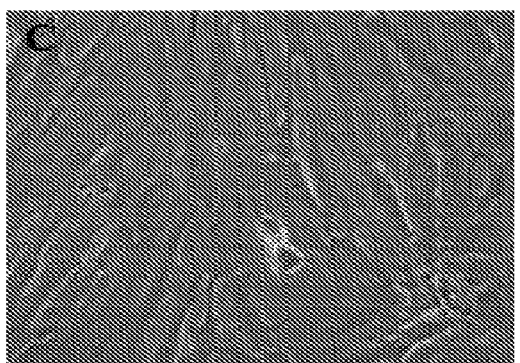

Porcine disc tissue cells plated on gelatin coated surfaces in Discotek media (Table 1) from the single cell suspension product of the tissue preparation method show initial attachment (FIG. 6), reached 70% confluency after a 3-5 day incubation (FIG. 7), and confluency after a 5-7 day incubation (FIG. 8). Human disc cells reached confluency after 10-12 days (FIG. 9). Thus, the rate of growth of the disc cells in this culture method (time to confluency) was typically dependent on the species of the disc tissue, the age of the animal, and the nature of the tissue itself (i.e., healthy vs. the degree to which the disc tissue was degenerated). The cell number and growth kinetic parameters from the tissue preparation method and the Attachment Culture Method are shown in Table 2.

Figure 10:
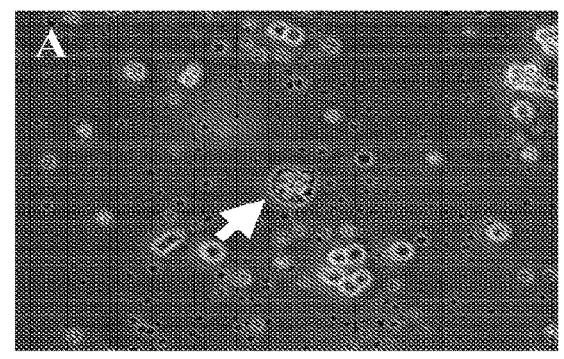
FIG. 10. Identification of notochordal cells in the Attachment Culture Method after plating of the single cell suspension product of tissue preparation. A. and B. 10× photomicrographs of a porcine single cell suspension at the time of plating in the attachment culture before the cells have had a chance to attach (A), and after 24 hours of attachment to gelatin on the plate's floor surface (B). C. 20× photomicrograph of porcine disc cells in the attachment culture on the third day after plating showing the persistence of notochordal cells (marked by a white arrow).
Figure 10:
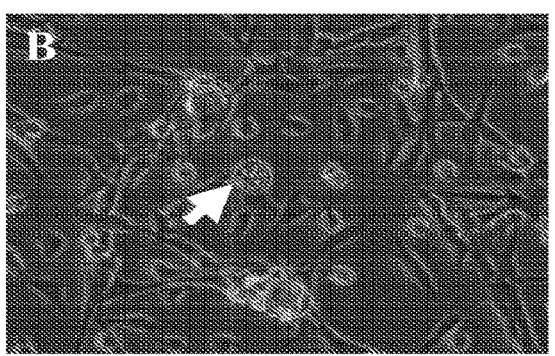
Figure 10:
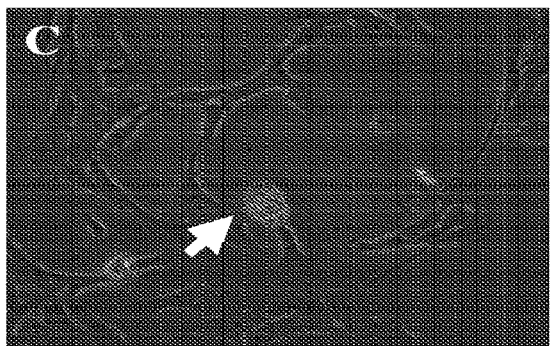

Notochordal cells were identified after plating of the single cell suspension product of tissue preparation using the Attachment Culture Method before and after cell attachment (FIG. 10). Notochordal cells were distinctly recognized because of their atypically large size and vacuolated appearance. All three photomicrographs in FIG. 10 show the predominant cells to be nucleus pulposus cells, but this data demonstrates the presence and persistence of the notochordal cells initially and out to several days in this initial culture method. Additionally, FIGS. 10A, 10B, and 10C demonstrate the presence of several types of cells that were not readily definable.

Example 4: Discosphere Culture Method

Figure 11:
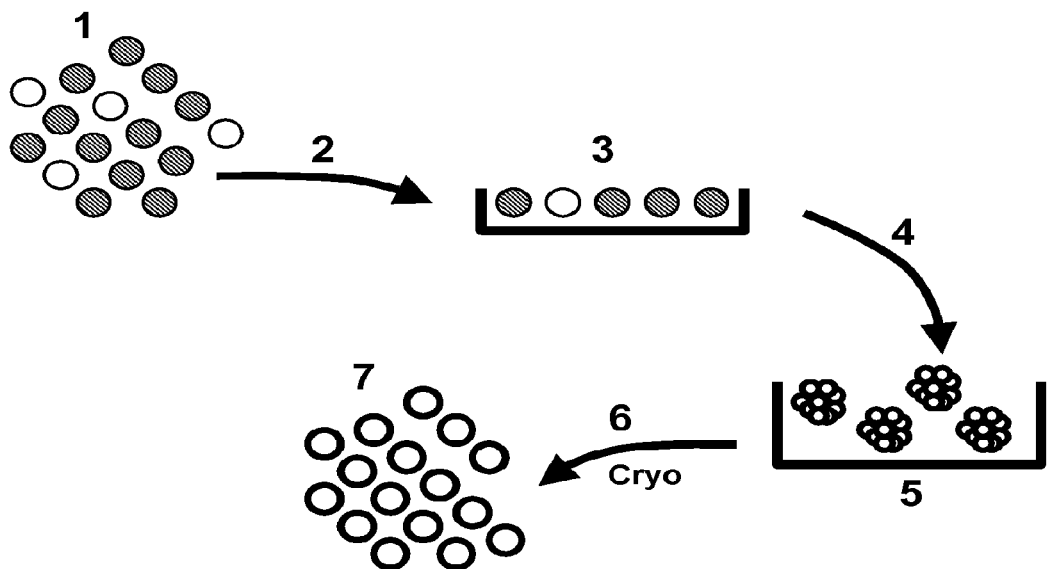
FIG. 11. Schematic of the Discosphere Culture Method.

When the cells were confluent, the attachment culture was passaged by preparing a single cell suspension using enzymatic digestion, and plating the cells in the Discosphere Culture Method (FIG. 11, reference numerals 1-5). This was also a step from which to cryopreserve attachment cells for future research studies. The Discosphere Culture Method uses methylcellulose in its media (Table 3), and uses coated tissue culture plates with ultra-low binding surfaces to create a suspension culture. The cells were plated at low density and because they were in suspension and could not attach to the culture vessel, each cell grew into a sphere-like cell cluster in a clonal manner. The spheres matured in size typically after 10-20 days. The cell number and growth kinetic parameters from the Discosphere Culture Method are presented in Table 4. When the spheres from the Disco-sphere Culture Method were mature, they were then passaged typically by preparing a single cell suspension (FIG. 11, reference numerals 6-7). However, a second method that was used was to transfer the disc stem cell spheres directly to the cluster culture.

TABLE 3

| Key Components of the Discosphere Culture Method and N5 Media. | |
| --- | --- |
| COMPONENT | AMOUNT/OTHER |
| MEDIA | DMEM/F12 |
| METHYLCELLULOSE | 50% |
| SERUM | 5% |
| FGF | 10 ng/ml |
| EGF | 10 ng/ml |
| CELL STATE | SUSPENSION |
| PLATING CELL DENSITY | $1 \times 10^4$ |
| TISSUE CULTURE SURFACE | ULTRA LOW BINDING |

| Protocol for 100 ml of N5 | Concentrations of Reagents: |
| --- | --- |
| 50 ml Methylcellulose | 16.1 µg/ml of Putrescine (100 µM) |
| 45 ml of stock 2X DMEM F12 Media | 62.8 µg/ml of Progesterone (20 µM) |
| 5 ml of Fetal Calf Serum | 5.2 µg/ml of Sodium Selenite (30 µM) |
| 100 µl of stock 1000X Sodium Selenite | 50 µg/ml of Transferrin. |
| 100 µl of stock 1000X Insulin | 5 µg/ml of Insulin |
| 100 µl of stock 1000X Putrescine | |
| 100 µl of stock 1000X Progesterone | |
| 100 µl of stock 1000X Transferrin | |

TABLE 4

| Identification of important cell number and growth kinetic parameters from the Discosphere Culture Method. | |
| --- | --- |
| COMPONENT | Number/Other |
| Cell State | Suspension as Spheres |
| Time to Maturity (Healthy Cellular Tissues) | 10-16 days |
| Time to Maturity (Degenerated Acellular Tissues) | 10-28 days |

Figure 12:
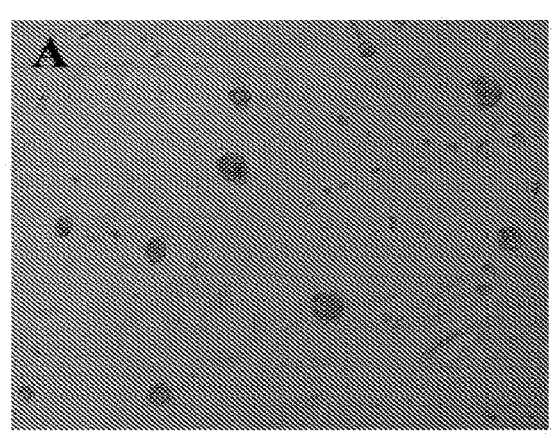
FIG. 12. The Discosphere Culture Method. A. 10× photomicrograph of human stem cells growing as discospheres in the Discosphere Culture Method. B. A 20× photomicrograph of human discospheres growing in the Discosphere Culture Method. C. and D. 40× photomicrographs of a single porcine discosphere growing in the Discosphere Culture Method.
Figure 12:
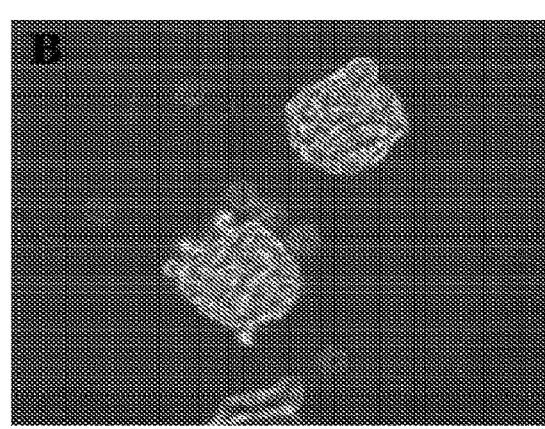
Figure 12:
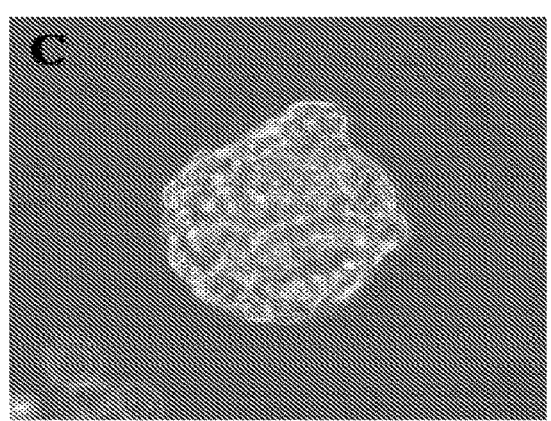
Figure 12:
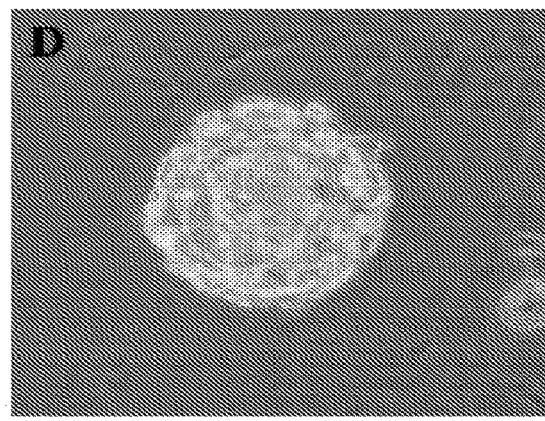

When the cells were confluent, the attachment culture was passaged by preparing a single cell suspension using enzymatic digestion, and plating the cells in the Discosphere Culture Method (FIG. 12). The spheres that developed were created from a single stem cell clonally. As the spheres grew in culture, the outer layers matured somewhat. However, as late progenitors or terminally differentiated stages of development were encountered, the cells entered apoptosis due to the inhospitable culture environment for mature or differentiated cells. Reasons for cell death were attributed to the lack of attachment to a plate surface, and the lack of cell-cell interaction caused by a relative low plating density.

Figure 13:
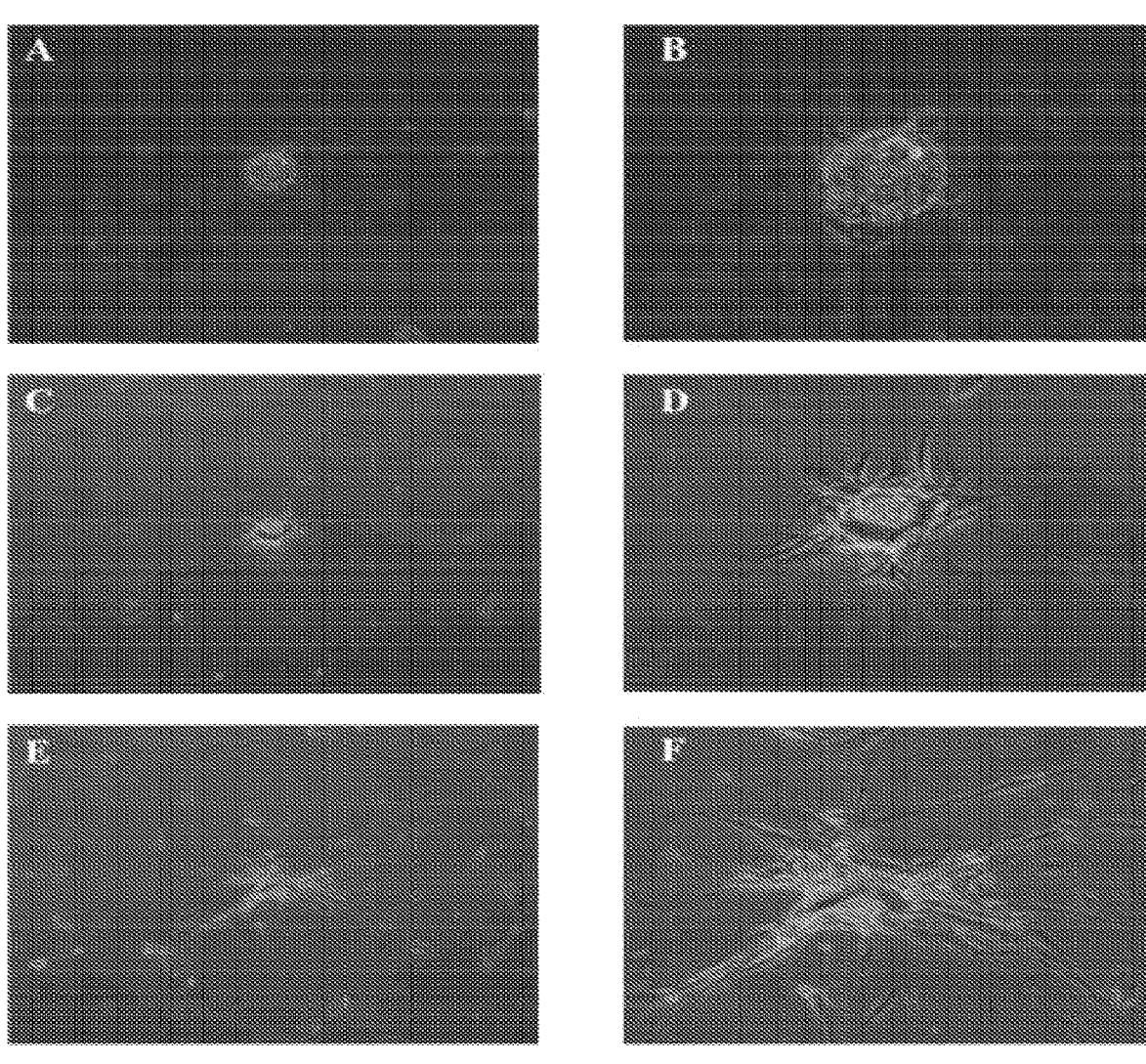
FIG. 13. Tissue engineering with Discospheres derived from the Discosphere culture system. Discospheres are collected from the culture and transferred to gelatin-coated coverslips and allowed to attach. A, C, and E: 20× photomicrographs taken at 24 hours, 48 hours, and 72 hour after first plating the spheres. Figures B, D, and F are enlarged to focus on the attached sphere of figures A, C, and E respectively, to better show cell activity at the tissue-surface interface and closely surrounding areas. Note the significant morphologic changes in the sphere at 72 hours (E and F) and surrounding cells as compared to activity at 24 hours (A and B).

Discospheres were collected from the culture and transferred to gelatin-coated coverslips and allowed to attach. The stem cell spheres gradually settle to the floor surface, and come in contact with the gelatin coating. The spheres attach, flatten, and cells at the sphere boundaries that are in contact with gelatin change in morphology and behavior over time. In particular, differentiation and proliferation occur at the edges of the sphere where it was attached to the coated surface. Beyond these areas, the cells become motile and migrate away from the sphere in all directions (FIG. 13).

Figure 14:
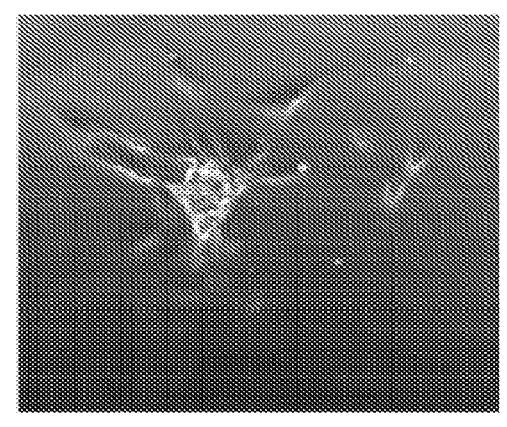
FIG. 14. A second example of 2D tissue engineering with Discospheres attached to a coated culture surface. Photomicrographs taken at 48 hours and 72 hours (shown at 20× magnification), and 96 hours and 120 hours (shown at 10× magnification) after first plating the spheres. This figure demonstrates the morphology of cells as they differentiate into nucleus pulposus cells and migrate from the attached sphere cluster at 48 hours. At 120 hours, the highly motile nature of the cells is apparent as the entire field is filled with migrating cells.
Figure 14:
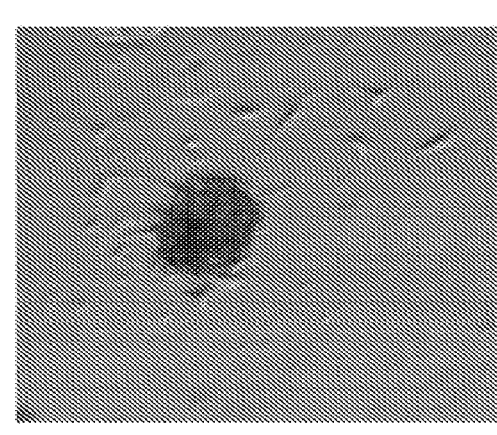
Figure 14:
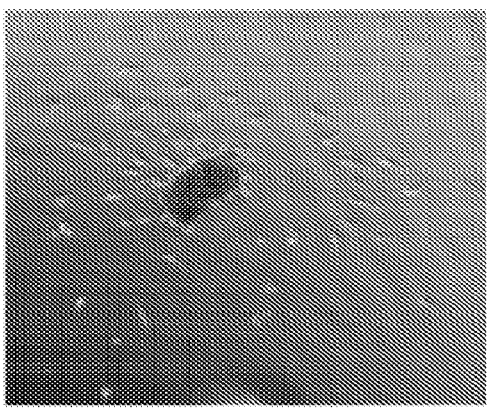
Figure 14:
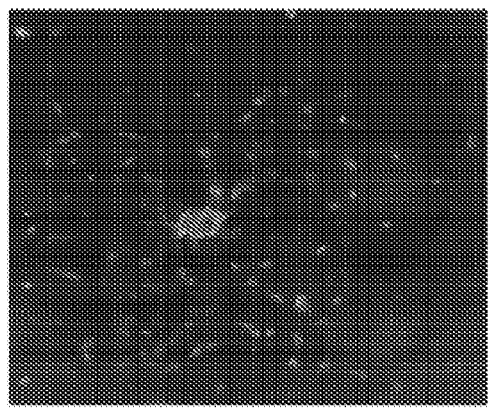

Next, some of the Discospheres in culture were collected and plated on gelatin coated coverslips and allowed to attach and grow and were followed in real time for 3-4 days. (FIG. 14). The stem cell spheres attach to the coated surface, and attachment in the presence of serum combined to cause the stem cell cluster to begin to flatten, and at the same time differentiation and rapid proliferation occurs at the edges of the sphere where it was attached to the coated surface. Proliferation and/or migration away from the sphere and also differentiation of the cells occurred over time.

Figure 15:
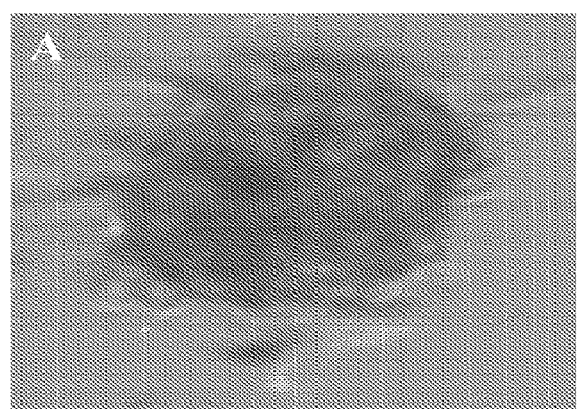
FIG. 15. Analysis of the expression of Vimentin in discospheres attached to gelatin for eight hours. A. 100× light microscopy photomicrograph demonstrating the cellular architecture of the attached disc stem cell sphere from a human patient sample. B. 100× fluorescent confocal photomicrograph demonstrating the immunohistochemical pattern of Vimentin in a sphere derived from a patient. C. 100× fluorescent confocal photomicrograph demonstrating the immunohistochemical expression pattern of Vimentin of the attached sphere from a second patient sample. D. 100× fluorescent confocal photomicrograph demonstrating the immunohistochemical expression pattern of the negative control for nonspecific antigen binding by the antibody.
Figure 15:
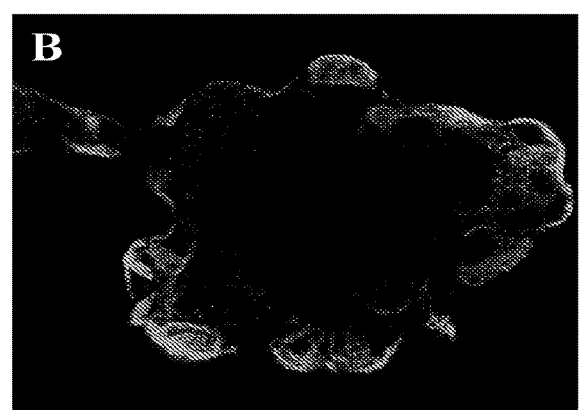
Figure 15:
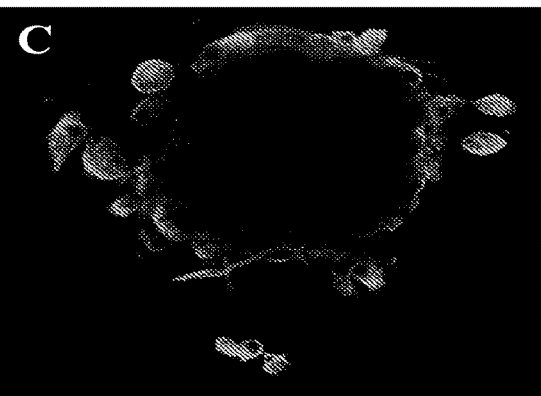
Figure 15:
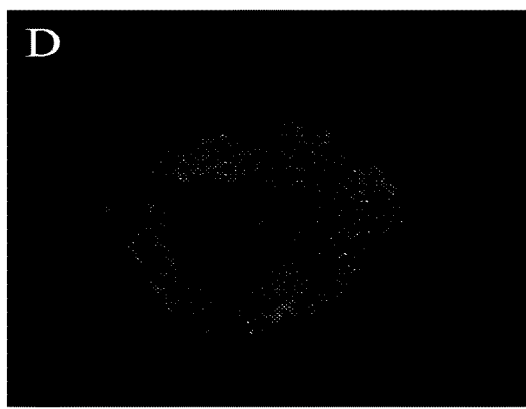
Figure 16:
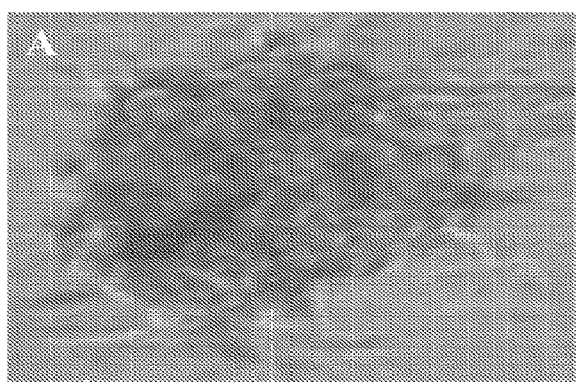
FIG. 16. Analysis of the expression of Cytokeratin 8 (CK8) in discospheres attached to gelatin for eight hours. A. 100× light microscopy photograph demonstrating the cellular architecture of an attached disc stem cell sphere from a human patient sample. B. 100× fluorescent confocal photomicrograph demonstrating the immunohistochemical expression pattern of CK8 in a sphere derived from a patient. C. 100× fluorescent confocal photomicrograph demonstrating the immunohistochemical pattern of CK8 of the attached sphere from a second patient sample. D. 100× fluorescent confocal photomicrograph demonstrating the immunohistochemical expression pattern of the negative control for nonspecific antigen binding by the antibody.
Figure 16:
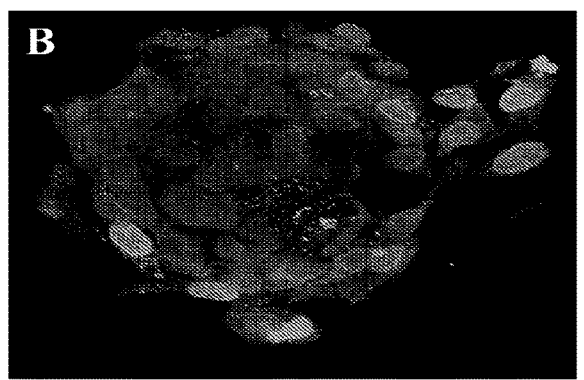
Figure 16:
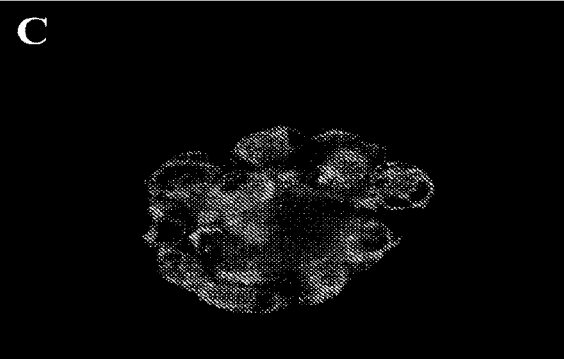
Figure 16:
Figure 17:
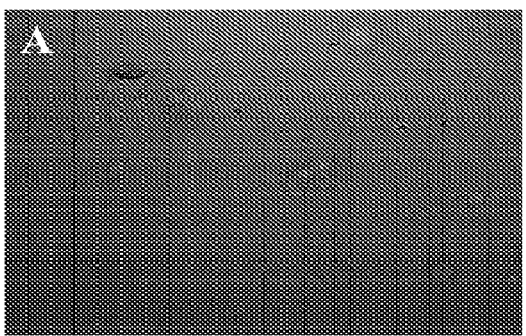
FIG. 17. Analysis of the expression of Cytokeratin 8 (CK8) in disc cells derived from Discosphere sphere culture, and attached to Gelatin for three days. A. 40× light microscopy photograph demonstrating the attached cells on the gelatin-coated surface. B. 40× fluorescent photomicrograph demonstrating the immunohistochemical expression pattern of CK8 in the individual cells shown in A. C. 40× fluorescent photomicrograph demonstrating the staining pattern of DAPI in the individual cells shown in A and B.
Figure 17:
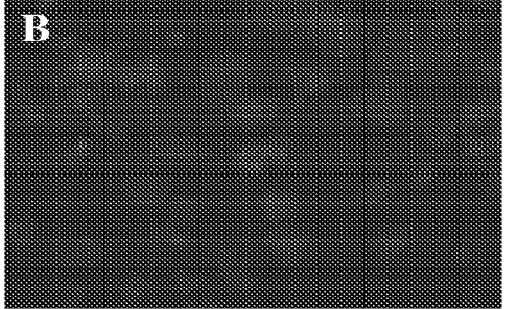
Figure 17:
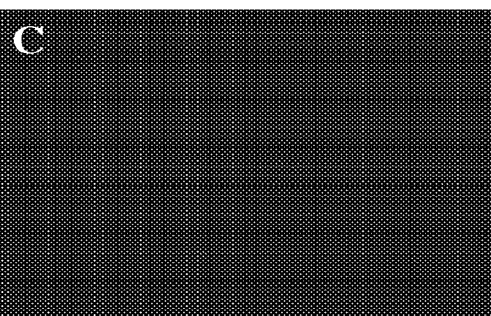

Discospheres were extracted from the Discosphere Culture Method, and plated on gelatin-coated coverslips in media containing 10% serum for approximately eight hours (FIGS. 15-16) or three days (FIG. 17). At eight hours, spheres were in primarily in a state between stemness (except the outer layers), but at the edges of the sphere, cells in contact with the gelatin-coated culture surface were undergoing differentiation. Vimentin was not expressed in the inner portion of the attached sphere where stem cells and early progenitors predominate (FIG. 15). However, as the cells at the sphere edge attached to the gelatin, differentiation began to occur in association with migration and proliferation (see also FIG. 14). Vimentin was upregulated in disc cells as they began to differentiate from stem cells or early progenitors at the outer portion of the Discosphere.

At eight hours, CK8 was expressed in the inner portion of the attached sphere (FIG. 16), and thus was associated with immature, stem-like phenotypy. Additionally, CK8 is a known marker of fetal nucleus pulposus and notochordal cells. Interestingly, the cellular cluster of staining was similar in its morphology and nature to that which was found naturally in fetal disc tissues. In fetal disc tissues, after early development of the spine has occurred through instruction of the paraxial mesoderm by the notochord, notochordal cells persist as clusters or aggregates interspersed with nucleus pulposus cells. In this scenario, the notochordal cells were positive for the expression of CK8, while the interspersed cells that make up the remainder of the disc were negative.

However, at three days, CK8 is expressed at moderate levels in some cells, and weakly or not at all in others (especially cells plated as single cells and not sphere clusters) (FIG. 17). Several cells do not express CK8, indicating that CK8 is likely down regulated in single cells that are attached and likely differentiating. This indicates that differentiation is associated with downregulation of CK-8. Thus, plating the cells as single cells instead of as a cluster, and attaching the cells for a longer period of time, both downregulate CK8.

Example 5: Cluster Culture Method

TABLE 6

Figure 18:
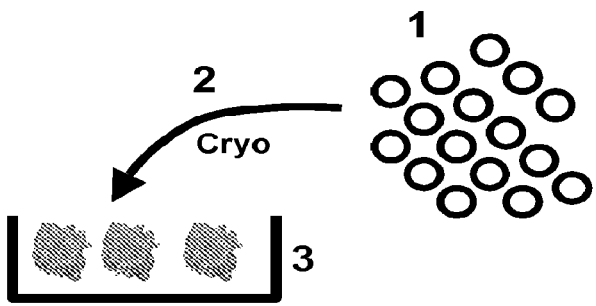
FIG. 18. Schematic of the Cluster Culture Method.

When the spheres from the discosphere culture method were mature, they were then passaged in one of two manners. First, to expand the cell population, they were passaged into the Cluster Culture Method by preparing a single cell suspension using enzymatic digestion, and plating the cells in the Cluster Culture Method at a predefined plating density. This was an appropriate time to cryopreserve stem cells in a single cell form. The cells were then grown in the Cluster Culture Method in cycles to expand them as needed. The time it typically takes for passaged cells from a single cell suspension to reach maturity as cluster like cell aggregates, was around 8-16 days. The end product of cycling the cluster cells was a stem cell product of the culture method, which can be cryopreserved for use at a future date. The second approach to passage from the discosphere culture to the cluster culture was to transfer the disc stem cell spheres to the Cluster Culture directly. The spheres grow into large clusters of heterogeneous morphology, reaching maturity in 8-14 days. This was a stem cell product of the culture method, and the large cell clusters can be cryopreserved for future use as indicated (FIG. 18, reference numerals 1-3).

Figure 19:
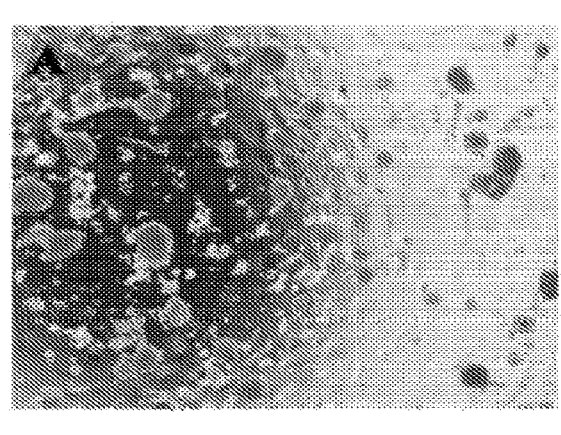
FIG. 19. The Disc Cell Cluster Culture Method. A. 4× photomicrograph of porcine disc clusters growing in the Cluster Culture Method. B. A 20× photomicrograph of porcine disc clusters growing in the Cluster Culture Method. C. A 20× photomicrograph of porcine disc clusters growing in the culture method. D. 40× photomicrographs of a single porcine cluster growing in the Cluster Culture Method.
Figure 19:
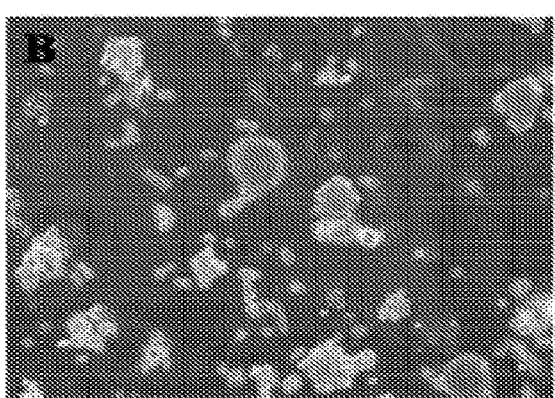
Figure 19:
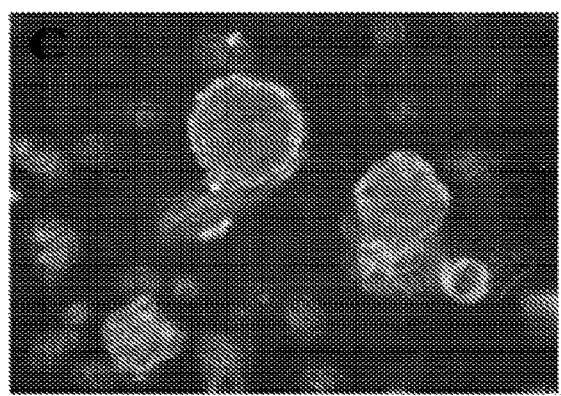
Figure 19:
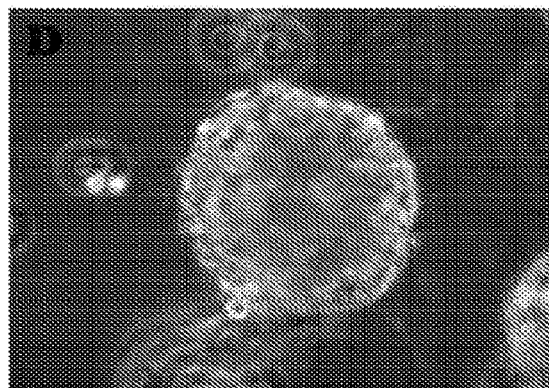

When the cells were confluent, the cluster culture was passaged by preparing a single cell suspension using enzymatic digestion, and the cells were replated into the cluster culture method. The Cluster Culture Method has as part of its media 10% serum, supplemented growth factors (Table 5), and uses tissue culture plates that were coated so that the surfaces were ultra-low binding. Thus, this was a suspension culture. The cells were plated in low density and because they were in suspension, each cell grows into an aggregate-like cell cluster. However, because of the lack of methylcellulose, the cells were free to move through the media and the clusters as well as smaller cells compositions (even single cells) aggregated and grew into large irregular clusters (FIG. 19). Aggregate cell clusters typically matured in size after 8-12 days. Cell number and growth kinetic parameters from the Cluster Culture Method are presented in Table 6. The clusters can be prepared as a single cell suspension and replated back into cluster culture to expand the cell population.

TABLE 6

Identification of important cell number and growth kinetic parameter from the Cluster Culture Method.

| COMPONENT | Number/Other |
|---|---|
| Cell State | Suspension as Aggregate Clusters |
| Time to Maturity (Healthy Cellular Tissues) | 10-16 days |
| Time to Maturity (Degenerated Acellular Tissues) | 10-28 days |

Figure 20:
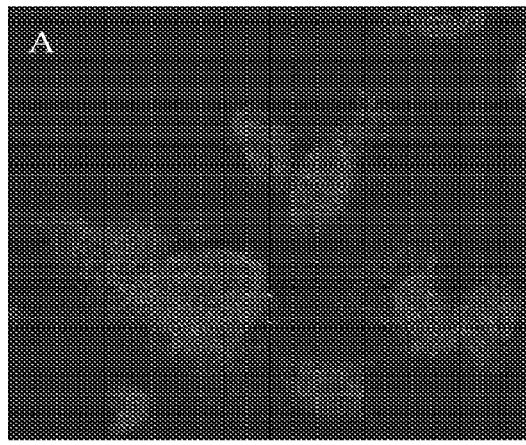
FIG. 20. Analysis of the expression of CD133 in disc cells derived from the Cluster Culture Method and plated on gelatin for five hours. A-C. 100× fluorescent photomicrographs of the expression of CD133 in individual cells.
Figure 20:
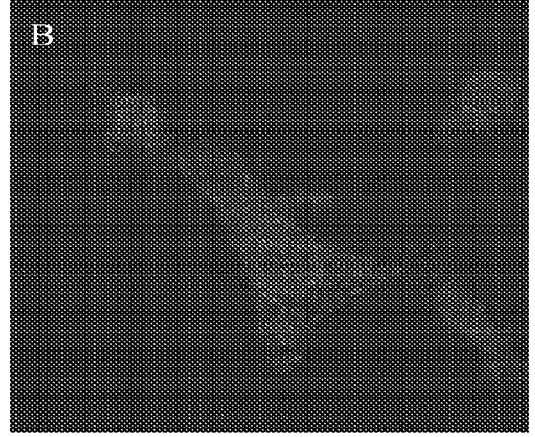
Figure 20:
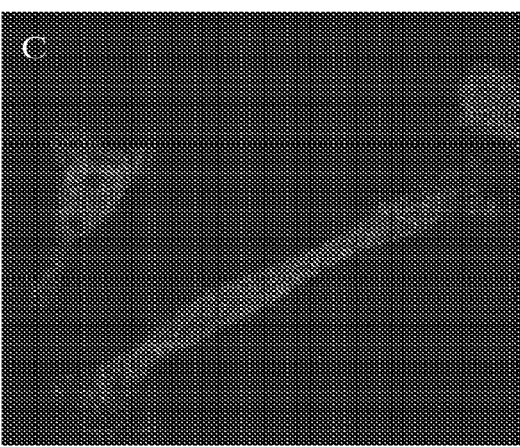

Cell clusters were extracted from the Cell Cluster Culture Method, and prepared as single cell suspensions by enzymatic digestion. The single cells were plated on cover slips coated with gelatin in media containing 1% serum for approximate five hours. CD133 was found to be highly expressed by most cells (FIG. 20) and emphasized the stem-like nature of the cell clusters generated in the Cell Cluster Method.

Figure 21:
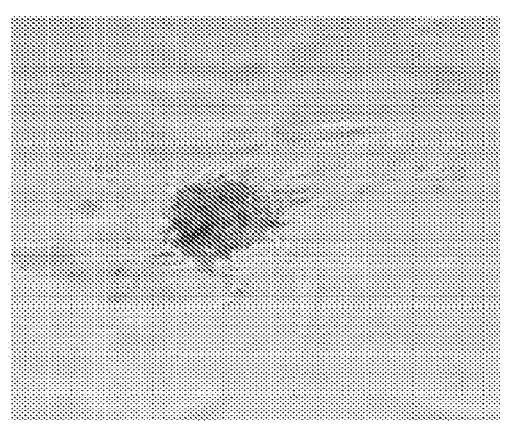
FIG. 21. 2D tissue engineering with Disc Cell Clusters attached to a coated culture surface. 20× photomicrographs taken at 48 hours, 72 hours, 96 hours, and 120 hours after first plating the clusters.
Figure 21:
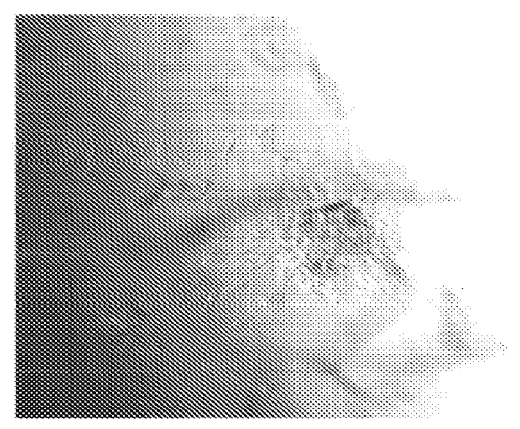
Figure 21:
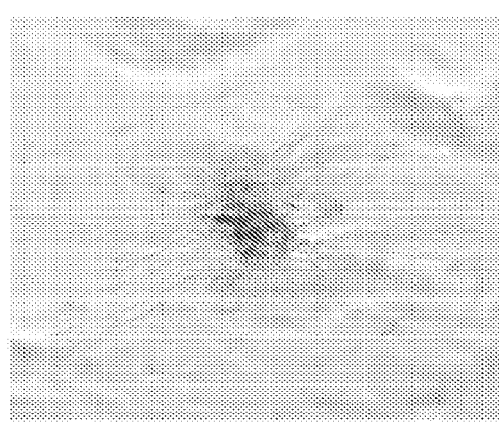
Figure 21:
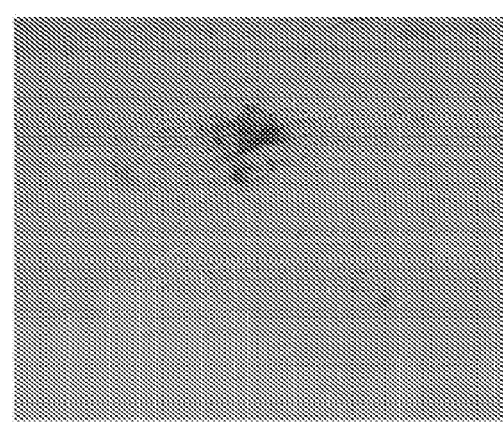

The disc stem cell clusters were collected and plated on gelatin coated coverslips and allowed to attach and grow. The stem cell clusters attach to the coated surface, and attachment plus serum combine to cause the stein cell cluster to begin to flatten, and at the same time differentiation and rapid proliferation occurs at the edges of the sphere where it was attached to the coated surface. Proliferation occurs in concert with migration away from the sphere and also with differentiation of the cells (FIG. 21).

Figure 22:
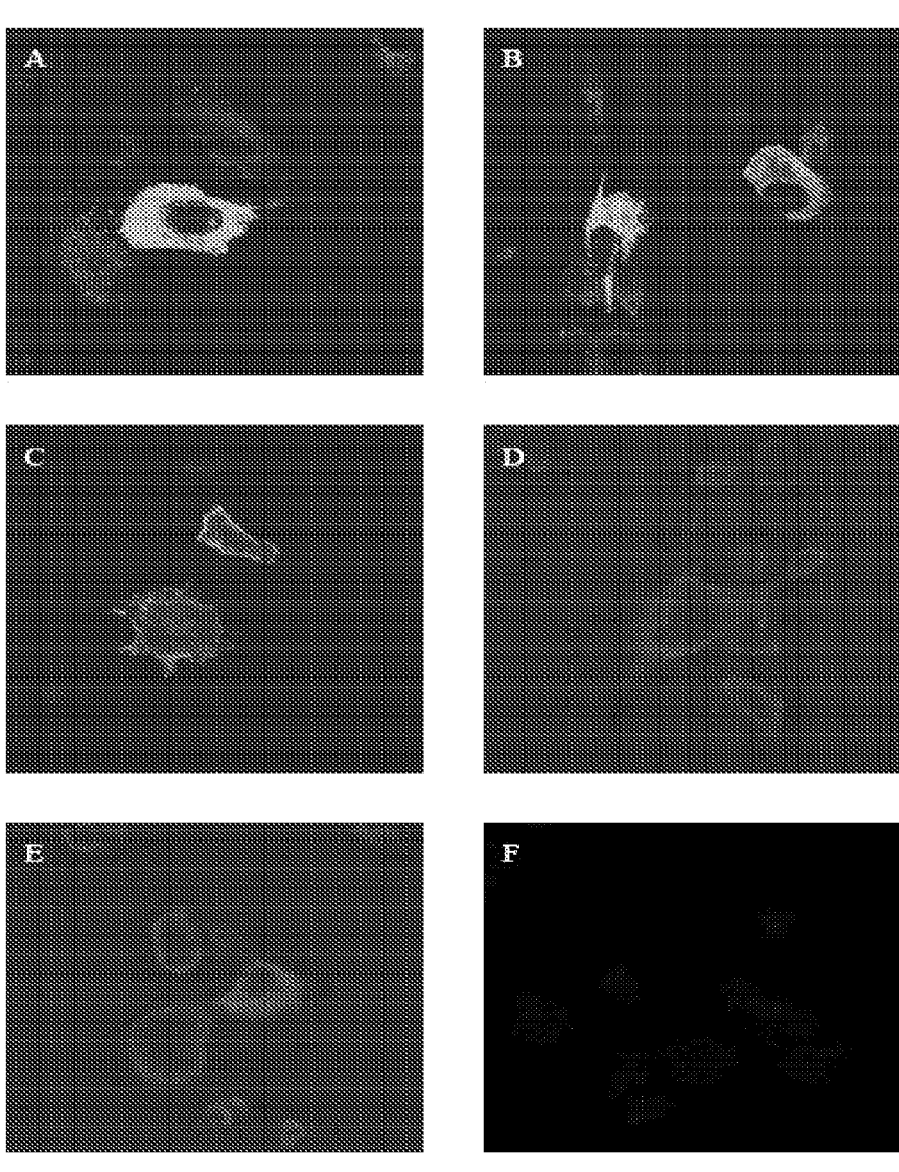
FIG. 22. Analysis of the expression of Collagen-2 alpha and Vimentin in disc cells derived from the Cluster Culture Method and plated in chondrogenic differentiating conditions. A.-C. 100× fluorescent confocal photomicrographs demonstrating the expression pattern of Collagen-2 alpha in single disc cells differentiated from cluster cells of the Cluster Cell Culture Method. D. and E. 100× fluorescent confocal photomicrographs demonstrating the expression pattern of Vimentin in single disc cells differentiated from cluster cells of the Cluster Cell Culture Method. F. 100× fluorescent confocal photomicrograph demonstrating the immunohistochemical expression pattern of the negative control for nonspecific antigen binding by the antibody.

Cell clusters were extracted from the Cell Culture Method, and prepared as single cell suspensions by enzymatic digestion. The single cells were plated on cover slips coated with Gelatin in chondrogenic differentiating media, and allowed to grow for 5 days. Collagen-Healthy (FIG. 22A-C) and Vimentin (FIG. 22D-E) are known markers of mature disc cells, and were expressed in nucleus pulposus cells. The morphology of these differentiated cells in tandem with their expression patterns were consistent with mature disc tissue derived cells.

TABLE 5

Key components of the Cluster Culture Method and N10 Media.

| COMPONENT | AMOUNT/OTHER |
|---|---|
| MEDIA | DMEM/F12 |
| SERUM | 10% |
| FGF | 10 ng/ml |
| EGF | 10 ng/ml |
| CELL STATE | SUSPENSION |
| PLATING CELL DENSITY | $1 \times 10^4$ |
| CELL SURFACE | ULTRA LOW BINDING |

| Protocol for 100 ml of N5 | Concentrations of Reagents: |
|---|---|
| 90 ml of stock 2X DMEM F12 Media | 16.1 µg/ml of Putrescine (100 µM) |
| 10 ml of Fetal Calf Serum | 62.8 µg/ml of Progesterone (20 µM) |
| 100 µl of stock 1000X Sodium Selenite | 5.2 µg/ml of Sodium Selenite (30 µM) |
| 100 µl of stock 1000X Insulin | 50 µg/ml of Transferrin. |
| 100 µl of stock 1000X Putrescine | 5 µg/ml of Insulin |
| 100 µl of stock 1000X Progesterone | |
| 100 µl of stock 1000X Transferrin | |

Figure 23:
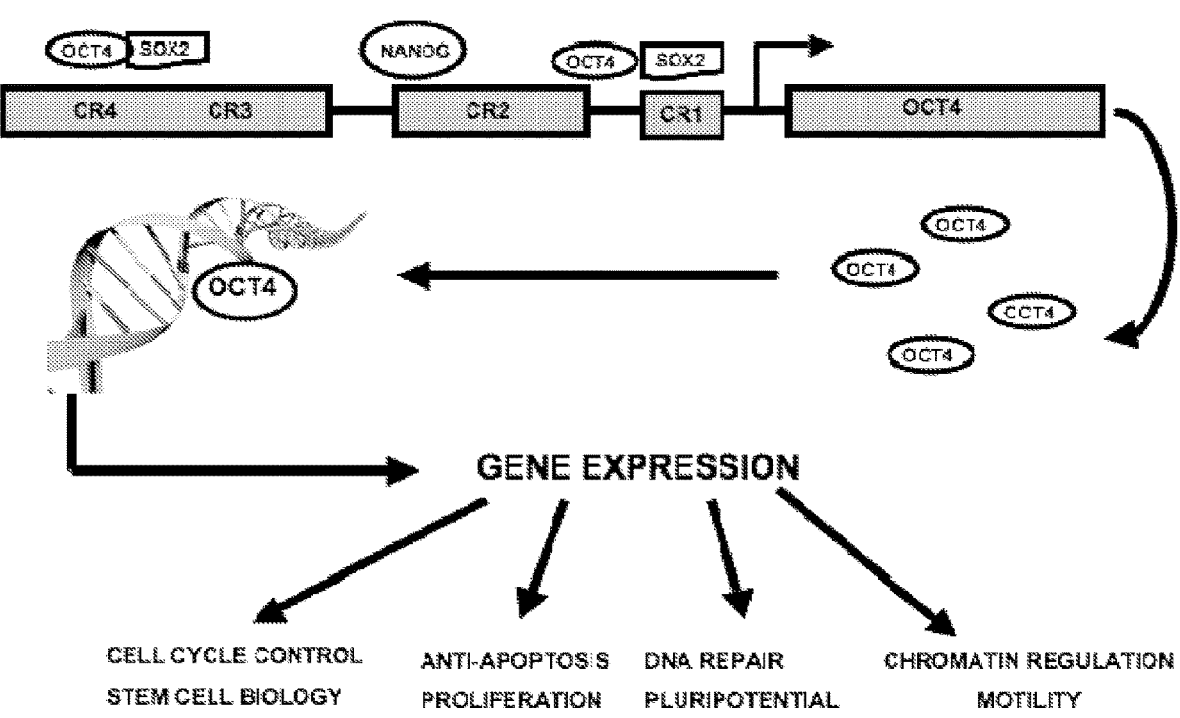
FIG. 23. Schematic of the central role of OCT-4, NANOG, and SOX-2 in embryonic stem cell biology. OCT-4, in concert with NANOG and SOX-2, is a master transcriptional regulator of embryonic stem cell biology. Its presence and activity in a stem cell indicates an early pluripotent stem-like state. These transcription factors regulate stem cell biology such as clonal division and the suppression of differentiation through their target genes, the so-called NOS genes (NANOG, OCT-4, AND SOX-2).
Figure 24:
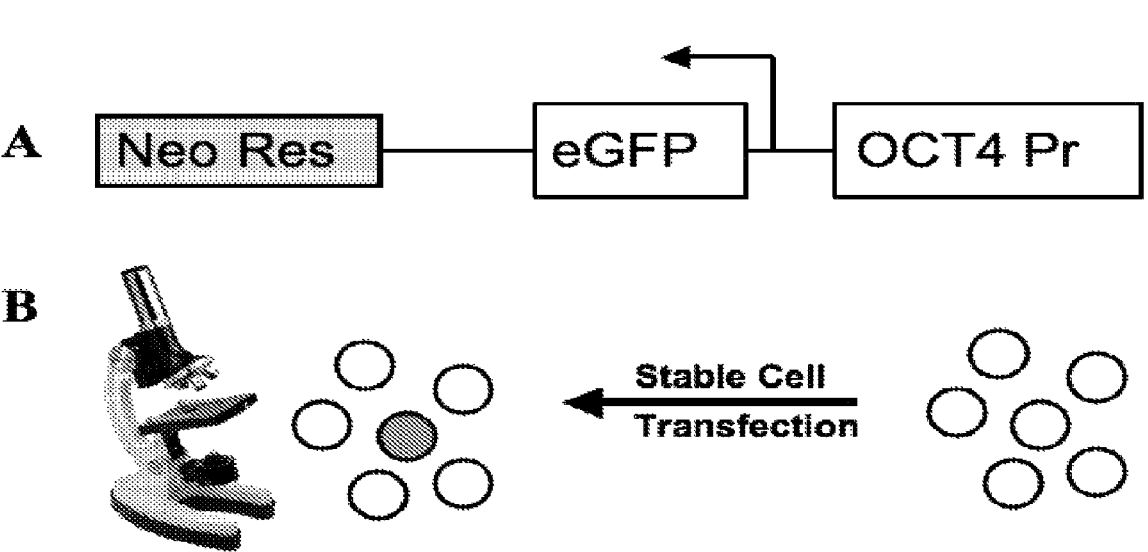
FIG. 24. Experimental design for creating stably transfected pOCT-4-eGFP reporter expressing disc tissue cells. A. Schematic of the pOCT-4-eGFP reporter transgene (the full length OCT-4 promoter with all four response elements cloned upstream of and regulating the expression of green fluorescent protein (GFP). B. Schematic of the experimental design used for identifying and isolating cells that express GFP as driven by the OCT-4 promoter. Briefly, disc stem cells were transfected with the pOCT-4-eGFP transgene. Stable transfectants were selected for their resistance to the antibiotic G418 (via activation of the NEO resistance gene cassette also on the reporter plasmid).
Figure 25:
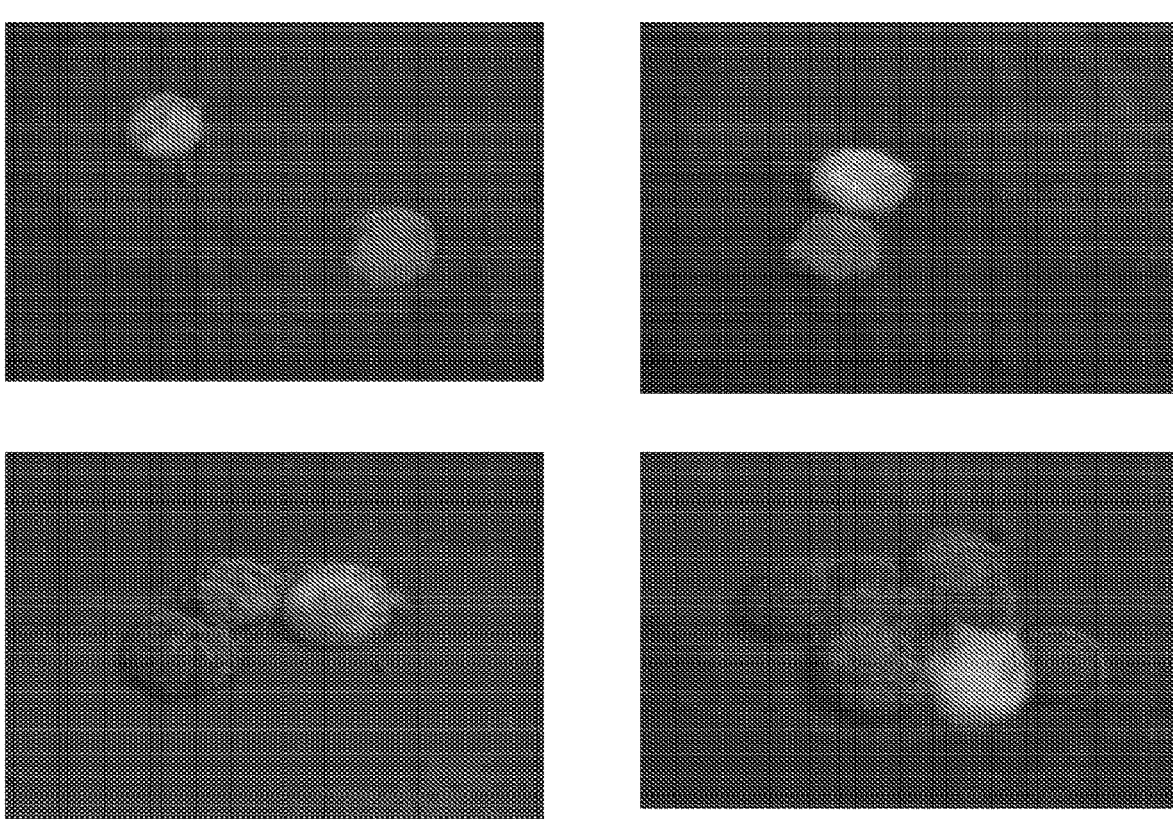
FIG. 25. Demonstration of activation of the OCT-4 promoter-GFP reporter transgene in stably transfected disc tissue stem cells in the sphere culture.

Example 6: Stem Cells Produced by the Discotek
Culture Method Demonstrate a Stem Cell
Phenotype In concert with NANOG and SOX-2, is a master transcriptional regulator of embryonic stem cell biology. Its
presence and activity in a stem cell indicates an early
pluripotent stem-like state. These transcription factors regu-
late stem cell biology and early fetal development. For
example, OCT-4 regulates clonal division and the suppression of differentiation through their target genes, the so
called NOS genes (NANOG, OCT-4, AND SOX-2) (FIG.
23). A pOCT-4-eGFP reporter transgene was constructed in
which all four response elements were cloned upstream of
and regulating the expression of green fluorescent protein
(FIG. 24A). Disc stem cells were transfected with the
pOCT-4-eGFP transgene, and stable transfectants were
selected for their resistance to the antibiotic G418 (via
activation of the NEO resistance gene cassette also on the
reporter plasmid) (FIG. 24B). The OCT-4 promoter-GFP
reporter transgene was activated in stably transfected disc
tissue stem cells in the various cultures described herein-
above, indicating that embryonic transcriptional machinery
was active and influencing the pluripotency and stem-like
behavior of disc tissue stem cells cultured in the Discotek
Platform (for example, the Discosphere culture as shown in
FIG. 25). The mechanism of these effects on stem cell
biology that can regulated by OCT-4 occurs through a
combination of epigenetic modifications of the genome, and
the transcriptional regulation of key target genes important
for embryonic stem cell phenotypy (e.g., NOS genes).

Figure 26:
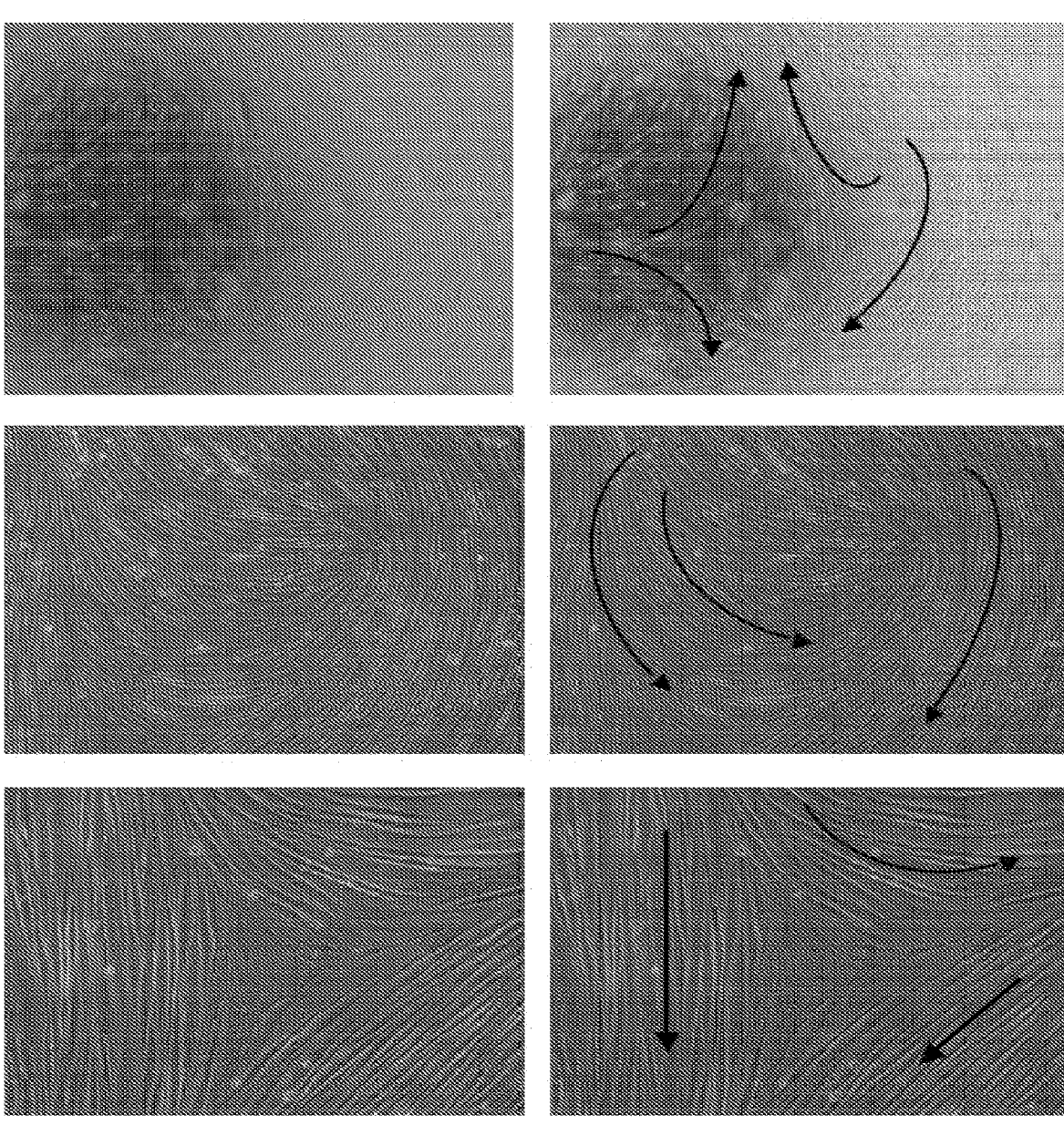
FIG. 26. Organization of Spindle Shaped Nucleus Pulposus Cells in 2D Tissue Engineering Assays. The left panels are light microscopy photographs at 10× (top), 20× (middle), and 40× (bottom) magnifications. The right panels are gray scale mirror images with arrows placed with the flow of disc cells along the surface of the plate.
Figure 27:
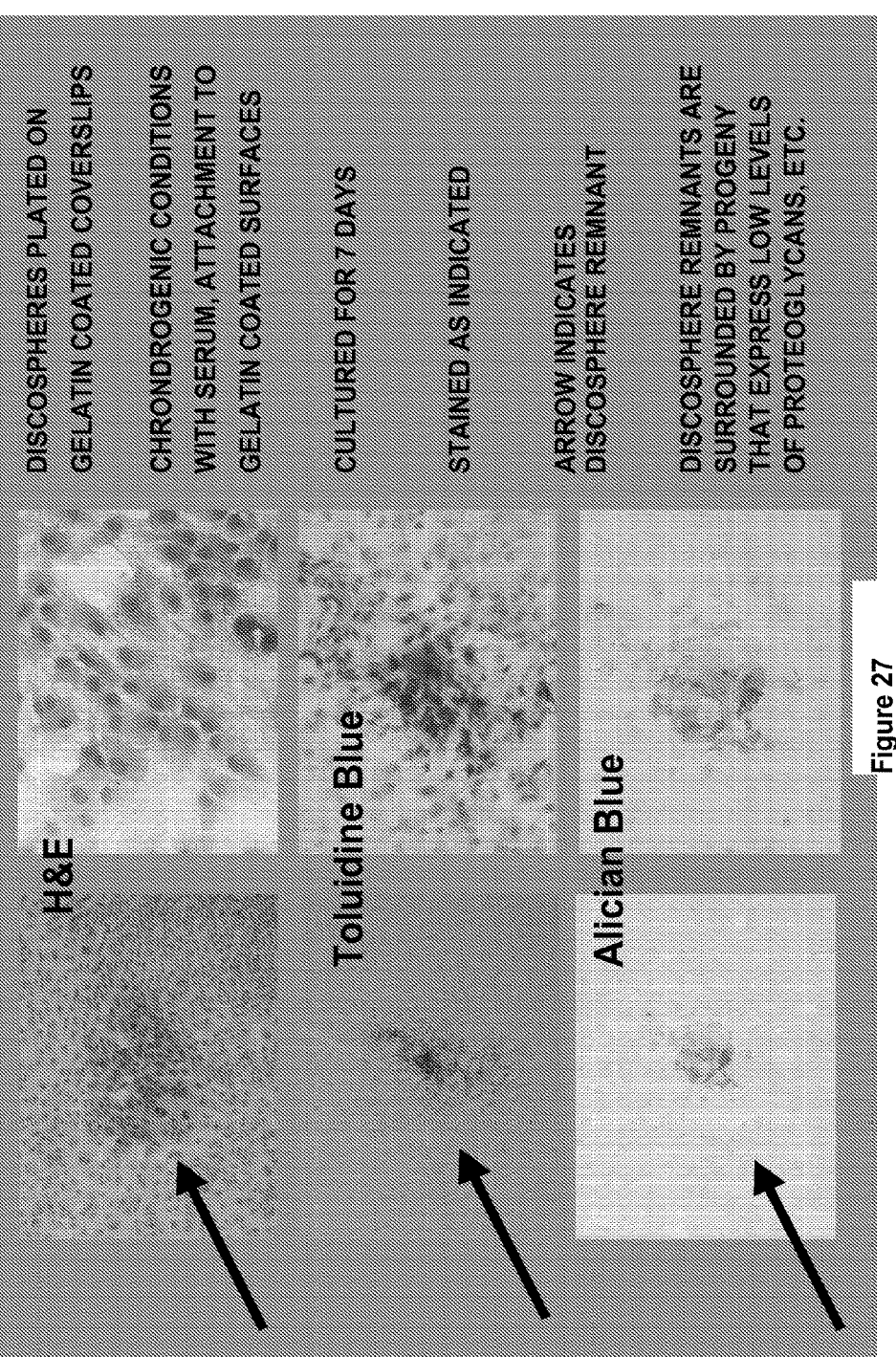
FIG. 27 shows histology and proteoglycan assays of discospheres plated on gelatin coated coverslips. Discosphere remnants are surrounded by progeny that express low levels of proteoglycans.

Disc stem cell spheres, when attached to a matrix coated
surface, grew in a random manner without pattern or orga-
nization. However, if a narrow window of sphere concen-
tration resulting in the achievement of specific inter-sphere
distances, a self organized structure occurred that swirled
around the central attached sphere and formed boundaries
with neighboring cell populations organized in a
similar·manner (FIG. 26). The result was a series of tissue
culture units with definable anatomy made up of organized
nucleus pulposus cells, and presumably organized by the
central stem cell cluster.

In disc cell cultures seeded from disc cell clusters, culture
conditions converted cell growth from nonspecific to highly
organized, and cell growth was contained within a certain
radius around the attached disc stem cell. Additionally, light
microscopy and high magnification microscopy using bire-
fringent polarized light was used to further characterize the
appearance in culture of floating and attached cell fibers with
a helical appearance. Finally, serial passaging and cell
counts from counterstained samples were used to estimate
and characterize the growth potential of nucleus pulposus
cells in extended disc stem cell and disc cell cultures.

As described hereinabove, collagen like structures of
various sizes and conformations were found to spontaneously appear in both disc stem cell and disc cell cultures. The
fibers were elongated and relatively straight structures and a
significant proportion had a helical conformation that could
be observed at very high magnification. Stem cell clusters
and nucleus pulposus cells were found to attach, migrate
along, grow upon, and grow from the fibers. The amount of
fibers observed increased the longer the cells were in culture.
Further, when disc stem cells were plated on ECM coated
surfaces at specific cell surface plating densities, the cell
progeny were found to emanate from them in a very specific,
reproducible, and organized cell pattern or array. These
arrays consisted of cells migrating from and proliferating around the original cluster in a circular manner with one
group of cells layered along another. Finally, these cultures
were passaged several times and the cell yield and surface
area covered was calculated and found to be exponentially
greater than that of the original seeded stem cell clusters.

The natural inclination of adult human disc stem cells to
form fibers, produce progeny that grow in an organized
manner, and give rise to large numbers of nucleus pulposus
cells demonstrates significant potential for stem cell based
tissue engineering to treat degenerative disc disease.

Example 7: Isolation and Characterization of Disc
Stem Cells from Human Adult Disc Tissue Degenerative disc disease (DDD) is a chronic degenera-
tion of disc tissue that occurs with aging, and the underlying
pathologic process for most spinal joint disease. Isolation
and characterization of adult disc stem cells from healthy
disc tissue is a step forward for developing stem cell based
therapeutic approaches to treat DDD. The aim of this study
was to determine whether adult disc stem cells could be
isolated from healthy and degenerated adult human disc
tissue isolated from human patients undergoing disc surgery.
Using the novel disc stem cell culture platform described
hereinabove, disc stem cells were cultured for expansion and
subjected to stem cell assays including clonal growth analy-
sis and differentiation studies. Immunohistochemistry was
used to demonstrate the expression of biomarkers of mature
nucleus pulposus cells. Basic tissue engineering methods
were used to characterize the growth kinetics and the total
cell yield of nucleus pulposus cell cultures derived from disc
stem cells in vitro.

Adult disc stem cells were efficiently and reproducibly
isolated from patient specimens that were relatively healthy
in nature. Disc stem cells grew clonally from single cells
into stem cell clusters that were spherical. Passaging stem
cells as a single cell suspension by replating them in the
same culture system for expansion resulted in a linear
growth rate. When disc stem cells were attached to extra-
cellular matrix coated surfaces in the presence of serum,
they rapidly differentiated into mature nucleus pulposus
cells as verified by morphology, cell biology assays, and the
expression of collagen 2, aggrecan, and vimentin. Addition-
ally, nucleus pulposus cell progeny grew for several pas-
sages and could be expanded exponentially when attached to
a matrix coated culture surface in the presence of chondro-
genic media. 'This report demonstrates the ability to isolate,
culture, and study in vitro adult disc stem cells from healthy
adult disc tissue. Disc stem cells readily give rise to nucleus
pulposus progeny with significant growth potential.

Adult disc stem cells were efficiently and reproducibly
isolated from degenerate patient specimens. Disc stem cells
grew clonally into stem cell clusters. Stem cell and disc cell
growth in culture was assessed and although expansion was
possible, there was significant variability in the results.
Passaging the stem cell clusters as single cell suspensions by
replating them in the same culture system for expansion
resulted in a linear growth rate in some patients but not
others. Disc stem cells, when attached to extracellular matrix
coated surfaces in the presence of serum, rapidly differen-
tiated into mature nucleus pulposus cells in all patient
samples as verified by morphology, cell biology assays, and
the expression of collagen 2, aggrecan, and vimentin. Addi-
tionally, nucleus pulposus cell progeny that grew for several
passages and could be expanded exponentially in 60% of all
patient samples when grown in chondrogenic tissue culture
conditions. We have demonstrated the ability to isolate, culture, and study in vitro adult disc stem cells from degenerated disc tissue. All patient's stem cells demonstrated significant growth potential when cultured in chondrogenic conditions. The observation of intra-patient variability likely relates to a combination of patient age, and disease status. The identification of biomarkers for stem cell viability in degenerated disc tissues from human adult patients is an important step for securing this patient population as a donor source for stem cell based therapeutics.

Example 8: In Vitro Tissue Engineering of Nucleus Pulposus Using Adult Disc Stem Cells Adult disc stem cell potential when combined with tissue engineering principles has significant potential for the treatment of DDD. The aim of this study was to investigate the in vitro tissue engineering potential of adult disc stem cells derived from healthy adult disc tissue. The ability of disc stem cells to generate functional nucleus pulposus cells and fabricate tissue in vitro was assessed.
Study Design:
We successfully isolated disc stem cells from healthy disc tissue for further study. Tissue engineering was used to characterize the rate of cell growth and several cell biology parameters. Novel 3 dimensional (D) tissue engineering models were created to characterize the ability of disc stem cells to grow in scaffolds, fill defects, and secrete extracellular matrix (ECM).

Methods disc stem cells were plated in basic tissue engineering assays and followed over time with light microscopy. The rate of development of progeny from the stem cells was characterized, as well as their ability to migrate, the velocity of motility, differentiation events, and the degree of proliferation. Subsequently, a novel 3 D tissue engineering model was used to determine the ability of adult disc stem cells to fill spatial defects that are seeded with scaffolds allowing cell migration in all directions. The ability of disc stem cells and seeded scaffolds to fabricate tissue and lay down ECM was determined with histologic stains and light microscopy. In both models, histology and immunohistochemistry for disc biomarkers was used to verify and further characterize nucleus pulposus cell progeny.

Results disc stem cells readily attached to ECM coated culture plates. Progenitor-like cells in contact with the coated surface migrated from the outside in, and spread across the available culture area in 96 hours. Migration was followed by proliferation, and the combination resulted in large surface areas surrounding the stem cell cluster being covered with nucleus pulposus cells. Using a 3 D scaffold based tissue engineering assay, disc stem cells were able seed scaffolds effectively, migrate multidirectionally, and proliferate to fill structural defects. Post-culture gross inspection revealed a disc like structure resembling nucleus pulposus. The neoengineered tissue was sectioned and histologic analysis revealed tissue fabrication histology that was moderately cell dense with extensive ECM. Stem cell cluster remnants were easily located. A variation of this model was used to observe in real time the morphology and migration of disc stem cells as they emerged from disc stem cell clusters. We have characterized the ability of disc stem cells to effectively populate tissue engineering assays in a relevant and functional manner.

Example 9: Disc with Endplate Tissue Scaffold Model

The aim of this study was to investigate the potential of human adult disc stem cells to create nucleus pulposus tissue in a denucleated rabbit disc annulus with endplates that serves as an effective 3 dimensional (D) scaffold. Denucleated rabbit annulus with thin bony endplates was prepared and used as a scaffold into which disc stem cells were injected to assess their ability to grow into disc tissue in vitro. Rabbit discs with bony endplates intact were dissected out as units from the lumbar portion of the spine. The discs were treated biochemically and mechanically to denucleate them from any central disc tissue, leaving only the annulus, inner matrix protein scaffolding, and the bony endplates. Disc stem cells were introduced and the disc units were cultured in chondrogenic media in a tissue culture incubator. A dynamic compressive force was applied to the disc unit on a daily basis, twice per day. The tissue engineering experiment was followed for 3 months, and the discs were then sectioned and assayed. Histologic stains for bone, fat, and cartilage were used to characterize the tissue. The expression of the extracellular matrix proteins collagen II and collagen I, and the proliferation marker, K167, were assayed using immunohistochemistry.

Results

Post-culture gross inspection revealed the disc unit had a full body that had physical properties such as tensile strength and resistance to compressive forces. The neoengineered tissue was sectioned and histologic analysis revealed a healthy appearing cartilage like tissue and no evidence of bone or fat formation. Expression of collagen II was significant, and the expression of collagen 1 was minimal, consistent with healthy disc tissue. Importantly, no KI67 expression could be detected, indicating that disc stem cells and their progeny had ceased to proliferate and likely differentiated.

What is claimed is:
1. A method of treating a subject suffering from a degenerative condition of a specific tissue with a tissue specific stem cell, comprising the steps of:
   a. suspending a sphere-like cluster of stem cells or an isolated stem cell from said sphere-like cluster in a medium comprising 6-10% serum, basic fibroblast growth factor (bFGF) and epidermal growth factor (EGF) and lacking methylcellulose, wherein the cluster of stem cells or isolated stem cell are derived from annulus pulposus, nucleus pulposus, transition zone or articular cartilage;
   b. distributing the suspension onto ultra-low binding culture plates;
   c. culturing said suspension for 8-16 days to produce a mature sphere of heterogeneous morphology having a diameter of roughly 100-600 microns, wherein the mature sphere comprises at least one tissue-specific stem cell selected from the group consisting of annulus pulposus, nucleus pulposus, transition zone, or articular cartilage; and
   d. isolating the at least one tissue-specific stem cell; and e. administering the at least one tissue-specific stem cell to said subject at or near articular cartilage, a joint, or an intervertebral disc, thereby treating the subject's degenerative condition.

2. The method of claim 1, wherein the at least one tissue specific stem cell is an articular cartilage stem cell.

3. The method of claim 2, wherein the at least one tissue specific stem cell is an articular cartilage stem cell and the administering is directly to a joint of said subject.

4. The method of claim 3, wherein said joint is a hip joint.

5. The method of claim 3, wherein said joint is a knee joint.

6. The method of claim 3, wherein said joint is a spinal joint.

7. The method of claim 1, wherein the administering is percutaneous or as part of an artificial intervertebral disc.

8. The method of claim 1, wherein said serum is present at a concentration of 10%.

9. The method of claim 1, wherein said bFGF is present at a concentration of 10 ng/ml.

10. The method of claim 1, wherein said EGF is present at a concentration of 10 ng/ml.

11. The method of claim 1, wherein the at least one tissue specific stem cell is selected from an annulus pulposus stem cell, transition zone stem cell, and nucleus pulposus stem cell.

12. The method of claim 11, wherein the administering is as part of an artificial intervertebral disc.

13. The method of claim 12, wherein the at least one tissue specific stem cell is an annulus pulposus stem cell.

14. The method of claim 12, wherein the at least one tissue specific stem cell is a transition zone stem cell.

15. A method of treating a subject suffering from a degenerative condition of a specific tissue with a tissue specific stem cell, comprising the steps of:
  a. suspending a sphere-like cluster of stem cells or an isolated stem cell from said sphere-like cluster in a medium comprising 6-10% serum, basic fibroblast growth factor (bFGF) and epidermal growth factor (EGF) and lacking methylcellulose, wherein the cluster of stem cells or isolated stem cell are derived from annulus pulposus, nucleus pulposus, transition zone, or;

b. distributing the suspension onto ultra-low binding culture plates;
  c. culturing said suspension for 8-16 days to produce a mature sphere of heterogeneous morphology containing approximately 100-500 cells, wherein the mature sphere comprises at least one tissue specific stem cell of annulus pulposus, nucleus pulposus, transition zone, or; and
  d. isolating the at least one tissue specific stem cell; and
  e. administering the at least one stem cell to said subject at or near articular cartilage, a joint, or an intervertebral disc, thereby treating the subject's degenerative condition.

16. The method of claim 15, wherein the at least one tissue specific stem cell is an articular cartilage.

17. The method of claim 16, wherein the at least one tissue specific stem cell is an articular cartilage stem cell and the administering is directly to a joint of said subject.

18. The method of claim 17, wherein said joint is a hip joint.

19. The method of claim 17, wherein said joint is a knee joint.

20. The method of claim 17, wherein said joint is a spinal joint.

21. The method of claim 15, wherein the administering is percutaneous or as part of an artificial intervertebral disc.

22. The method of claim 15, wherein said serum is present at a concentration of 10%.

23. The method of claim 15, wherein said bFGF is present at a concentration of 10 ng/ml.

24. The method of claim 15, wherein said EGF is present at a concentration of 10 ng/ml.

25. The method of claim 15, wherein the at least one tissue specific stem cell is selected from an annulus pulposus stem cell, transition zone stem cell, and nucleus pulposus stem cell.

26. The method of claim 25, wherein the administering is as part of an artificial disc.

27. The method of claim 26, wherein the at least one tissue specific stem cell is an annulus pulposus stem cell.

28. The method of claim 26, wherein the at least one tissue specific stem cell is transition zone stem cell.

* * * * *